United States Patent [19]

Mori et al.

[11] Patent Number: 5,731,455
[45] Date of Patent: Mar. 24, 1998

[54] LIGNAN ANALOGUES, METHODS OF PREPARATION THEREOF AND ANTI-HYPERLIPEMIC AGENTS

[75] Inventors: Sachio Mori, Ashiya; Shozo Takechi, Higashiosaka; Shiro Kida, Osaka; Takuji Mizui, Takarazuka; Teruhisa Ichihashi, Kobe, all of Japan

[73] Assignee: Shionogi & Co., Ltd., Osaka, Japan

[21] Appl. No.: 423,346

[22] Filed: Apr. 18, 1995

Related U.S. Application Data

[62] Division of Ser. No. 301,996, Sep. 7, 1994, which is a division of Ser. No. 78,205, filed as PCT/JP92/01342, Oct. 15, 1992, published as WO93/08155, Apr. 29, 1993, Pat. No. 5,420,333.

[30] Foreign Application Priority Data

Oct. 17, 1991 [JP] Japan ................ 6-298119

[51] Int. Cl.⁶ .................................. C07C 69/66
[52] U.S. Cl. .................................. 560/174
[58] Field of Search ........................ 560/174

[56] References Cited

U.S. PATENT DOCUMENTS

| 4,771,072 | 9/1988 | Iwasaki et al. ............ 514/533 |
| 4,840,951 | 6/1989 | Iwasaki et al. ............ 514/239.5 |

FOREIGN PATENT DOCUMENTS 3-72422  3/1991  Japan .

OTHER PUBLICATIONS

Chem. Abs. 110:38606 (1988).
Broom et al., "A General Route to Substituted Naphthols", J. C. S. Chem. Comm., 1978, pp. 162–164.

*Primary Examiner*—Paul J. Killos
*Attorney, Agent, or Firm*—Wenderoth, Lind & Ponack

[57] ABSTRACT

An anti-hyperlipemic agent which has a potent activity of reducing LDL and VLDL cholesterols, which are thought to be a risk factor for arteriosclerosis among total blood cholesterols, and which is excellent in the antioxidant activity on LDL, is provided. Additionally, a compound and a pharmaceutically acceptable salt thereof are disclosed, which is represented by Formula (I):

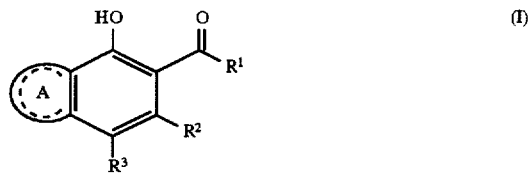

[wherein $R^1$ is a lower alkyl, cycloalkyl, cycloalkyl-lower alkyl, aryl or aralkyl group which is optionally substituted; $R^2$ is a group represented by the formula: —COOR' (wherein R' is a lower alkyl or aralkyl which is optionally substituted), lower alkyl or halogenated lower alkyl; or $R^1$ and $R^2$, together with adjacent carbonyl group, form a cyclohexanone ring represented by the formula:

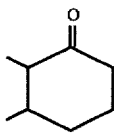

$R^3$ is a phenyl group optionally being substituted, and, ring A is a benzene nucleus which is optionally substituted, or a heterocyclic ring containing S or O optionally being substituted].

1 Claim, No Drawings

LIGNAN ANALOGUES, METHODS OF PREPARATION THEREOF AND ANTI-HYPERLIPEMIC AGENTS

This is a divisional application of Ser. No. 08/301,996 filed Sep. 7, 1994, which is a divisional application of Ser. No. 08/078,205 filed Jun. 17, 1993, now U.S. Pat. No. 5,420,333 which is the national phase of PCT/JP92/01342 filed Oct. 15, 1992 published as WO93/08155, Apr. 29, 1993.

FIELD OF THE INVENTION

The present invention relates to a compound (hereinafter referred as Compound (I) of the present invention) represented by Formula (I):

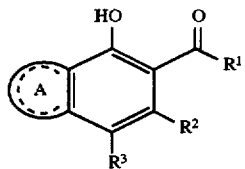

[wherein
$R^1$ is a lower alkyl, cycloalkyl, cycloalkyl-lower alkyl, aryl or aralkyl group which is optionally substituted, $R^2$ is a group represented by the formula: —COOR': (wherein R' is a lower alkyl or aralkyl which is optionally substituted), lower alkyl or halogenated lower alkyl, or, $R^1$ and $R^2$, together with adjacent carbonyl group, form a cyclohexanone ring represented by the formula:

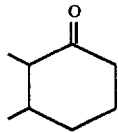

$R^3$ is a phenyl group optionally being substituted, and, ring A is a benzene nucleus which is optionally substituted, or a heterocyclic ring containing S or O optionally being substituted],
and pharmaceutically acceptable salts thereof. The present invention also provides anti-hyperlipemic agents containing these compounds.

PRIOR ART

Hyperlipemia is believed to be one of the major causes of a geriatric disease arteriosclerosis. Among the hyperlipemic diseases, hypercholesterolemia is particularly in close relationship with arteriosclerosis. Cholesterol is present in blood in either one of the forms of very low density lipoprotein (hereinafter referred as VLDL), low density lipoprotein (LDL) and high density lipoprotein (HDL). VLDL and LDL enhance deposition of cholesterol in an arterial wall thereby causing arteriosclerosis, while HDL prevents the deposition and exhibits therapeutic and prophylactic effects against arteriosclerosis, as reported in Annals of Internal Medicine, 90, 85, (1979). Accordingly, an anti-hyperlipemic agent capable of reducing selectively VLDL and LDL cholesterols is desired in the field of treatment and prophylaxis of arteriosclerosis.

Drugs directed to the purpose described above were disclosed, for example, in Japanese Patent Publication Nos. H3-72422, H3-157351, H2-72136 and H1-135766.

PROBLEMS TO BE SOLVED BY THE INVENTION

Among factors causing atherosclerosis which is most significant in arteriosclerotic diseases, the behavior of LDL cholesterol in blood is quite important. Especially, permeation of LDL into arterial walls and incorporation of LDL by macrophages in the wall, and resulting formation of foam cells and accumulation of cholesterols in intima and blood vessel failures are very important. It is believed that oxidized LDLs are exclusively incorporated into macrophages (D. Steinberg, S. Parthasarathy, T. E. Carew, J. C. Khoo and J. L. Witztum, N. Engl. J. Med., 320, 915 (1989)). Thus, an anti-hyperlipemic agent having anti-oxidizing effect on LDLs in addition to the ability of reducing VLDL and LDL cholesterols selectively as mentioned above is desirable. However, no such agents have been reported.

DETAILED DESCRIPTION OF THE INVENTION

It has been found surprisingly that Compounds (i) and pharmaceutically acceptable salts thereof according to the present invention have anti-oxidizing effect on LDLs in addition to the ability of reducing VLDL and LDL cholesterols selectively.

Compounds (I) of the present invention can readily be converted into desirable salts by a known manner.

Pharmaceutically acceptable salts of Compounds (I) include alkaline metal salts such as sodium and potassium salts, alkaline earth metal salts such as calcium and magnesium salts, and quaternary ammonium salts such tetramethylammonium salt. Throughout the specification, the terms have the meanings as described below.

In the definition of group $R^1$ in Formula (I), "a lower alkyl group which is optionally substituted" means a straight or branched $C_1$–$C_6$ alkyl which may have one or more substituents. "A straight or branched $C_1$–$C_6$ alkyl" includes methyl, ethyl, n-propyl, i-propyl, n-butyl, i-butyl, s-butyl, t-butyl, n-pentyl, i-pentyl, neopentyl, s-pentyl, t-pentyl, 1-ethylpropyl, n-hexyl, neohexyl, i-hexyl, s-hexyl and t-hexyl. The substituent may be hydroxyl, halogen atom (F, Cl, Br, I), amino, cyano, nitro, nitroso, hydrazino, hydroxyamino, thiol-and lower alkoxy groups. The lower alkoxy groups include methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy.

"A cycloalkyl which is optionally substituted" means a $C_3$–$C_7$ cycloalkyl group which may have one or more substituents. The $C_3$–$C_7$ cycloalkyl includes cyclopropane, cyclobutane, cyclopentane, cyclohexane and cycloheptane. The substituent may be hydroxyl, halogen atom (F, Cl, Br, I), amino, cyano, nitro, nitroso, hydrazino, hydroxyamino, thiol and lower alkoxy groups, and the lower alkoxy groups include methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy.

"A cycloalyyl-lower alkyl which is optionally substituted" means a lower alkyl defined above which is substituted with a cycloalkyl which may optionally be substituted as defined above, and includes cyclopropylmethyl, cyclobutylpropyl, cyclopentylethyl, cyclohexylpropyl and cyclohexylmethyl.

In the definition of group $R^1$, "an aryl group which is optionally-substituted" means a phenyl or naphthyl which may have one or more substituents. The substituents may be lower alkyl groups listed above, lower alkoxy groups listed above, hydroxyl, halogen atom (F, Cl, Br, I), haloalkyl such as trifluoromethyl, amino, cyano, nitro, nitroso, hydrazino, hydroxyamino and thiol groups.

"An aralkyl group which is optionally substituted" means a lower alkyl defined above which is substituted with an aryl which may optionally be substituted as defined above, and includes benzyl, p-methoxybenzyl, phenetyl phenylpropyl and naphthylmethyl.

In the definition of group $R^2$ in Formula (I), "a group represented by the formula: —COOR' wherein R' is a lower alkyl or aralkyl which is optionally substituted" means a carboxylate ester residue containing an alkyl or aralkyl group which may be substituted.

"A halogenated lower alkyl group" in group $R^2$ means a lower alkyl defined above which is substituted by a halogen atom, such as trifluoromethyl (—$CF_3$), pentafluoroethyl and chloroethyl.

In the definition of group $R^3$, "a phenyl group which is optionally substituted" means a phenyl group optionally having one or more substituents, or a phenyl-containing condensed ring such as 3,4-ethylenedioxyphenyl group represented by the formula:

The substituents may be lower alkyl groups listed above, lower alkoxy groups listed above, hydroxyl, halogen atom (F, Cl, Br, I), amino, cyano, nitro, nitroso, hydrazino, hydroxyamino and thiol groups.

In the definition of ring A, "a benzene nucleus which is optionally substituted" means a benzene nucleus which may have one or more substituents, or a benzene-containing condensed ring represented by the formula:

The substituents may be lower alkyl groups listed above, lower alkoxy groups listed above, hydroxyl, halogen atom (F, Cl, Br, I), amino, cyano, nitro, nitroso, hydrazino, hydroxyamino and thiol groups.

In the definition of ring A, "a heterocyclic ring containing S or O optionally being substituted" means a 5 or 6 membered aromatic heterocyclic ring which may have one or more substituents and which contains one or more of S or O atoms in the ring. Such aromatic heterocyclic ring may include furan and thiophene. The substituents may be ones selected from the group of lower alkyl groups listed above, lower alkoxy groups listed above, hydroxyl, halogen atom (F, Cl, Br, I), amino, cyano, nitro, nitroso, hydrazino, hydroxyamino, thiol and $C_1$-$C_3$ alkylenedioxy groups.

The methods of preparation of the present compounds are described below. Representative methods of preparation of the present compounds and pharmaceutically acceptable salts thereof are as follows.

A) a compound (hereinafter referred as Compound (II)) of Formula (II):

wherein ring A and $R^3$ are defined as above, and a compound (hereinafter referred as Compound (III)) of Formula (III):

$$R^1OC{-}C{\equiv}C{-}R^2 \quad \text{(III)}$$

wherein $R^1$ is defined as above, and $R^2$ is a group represented by the formula —COOR' (wherein R' is a lower alkyl or aralkyl group which is optionally substituted), are subjected to addition reaction; or B) A compound (hereinafter referred as Compound (IV)) of Formula (IV):

wherein $R^2$, $R^3$ and ring A are defined as above, and a compound (hereinafter referred as Compound (V)) of Formula (V):

$$R^1{-}M \quad \text{(V)}$$

[wherein $R^1$ is defined as above, and M is lithium atom or a group of magnesium atom-halogen atom], are subjected to substitution reaction.

The methods of preparation of the present compounds are detailed below. Throughout the specification, all of the ratios of compounds used are represented as molar ratios.
(Method A)

Scheme of steps

[wherein, $R^1$, $R^3$ and ring A are defined as above, and $R^2$ is a carboxylate ester residue containing a lower alkyl or aralkyl group which may be substituted.]

According to the method of Plaumann et al. (H. P. Plaumann, J. G. Smith and R. Rodrigo, J. Chem. Soc. Chem. Commun., 354 (1980)), Compound (II) and Compound (III) are subjected as starting materials to thermal cyclic addition reaction in the presence of an acid catalyst in the presence or absence of a solvent.

Although the ratio of Compound (II) to Compound (III) is not particularly limited, it is usually 1:1.

The solvent useful in the reaction includes aromatic hydrocarbons such as benzene, toluene and xylene, halogenated hydrocarbons such as dichloromethane and chloroform as well as aprotic solvents such as dimethoxyethane, dioxane and tetrahydrofuran.

The acid catalyst useful in the reaction may be any of the catalysts capable of being used in usual thermal cyclic addition reaction and includes inorganic acids such as hydrochloric acid, sulfuric acid and Lewis acid ($BF_3$) as well as organic acids such as trifluoroacetic acid, acetic acid, formic acid and sulfonic acids (e.g. methanesulfonic acid, p-toluenesulfonic acid).

The reaction is usually completed by heating the reactants at a temperature from room temperature to about 150° C., preferably at about 50° C. to about 130° C. for a period more than 10 minutes and up to several hours.

(Method B)

Scheme of steps

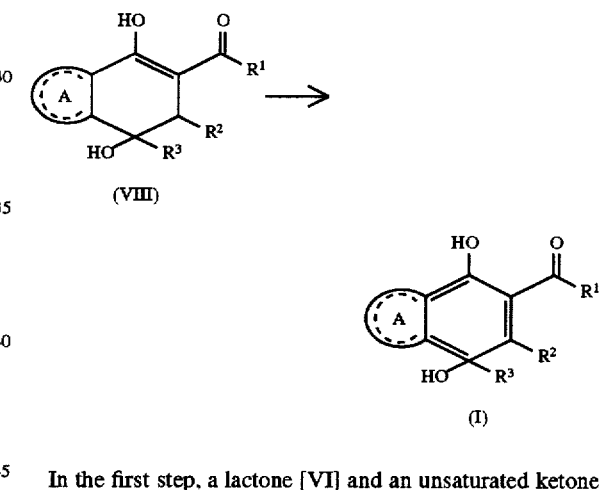

[wherein, $R^1$, $R^3$, ring A and M are defined as above, and $R^2$ is a carboxylate ester residue containing a lower alkyl or aralkyl group which may be substituted.]

Starting materials, Compound (IV) and Compound (V), are subjected to substitution reaction in the atmosphere of an inert gas.

Although the ratio of Compound (V) to compound (IV) is not particularly limited. Compound (V) is usually used at about 1 to about 10 equivalents, preferably at about 3 to about 5 equivalents, relative to Compound (IV).

The reaction solvent includes dichloromethane or a solvent usually employed in Grignard reaction, such as anhydrous ether and a mixture of dichloromethane and tetrahydrofuran.

The inert gas is not particularly limited, but is usually argon or nitrogen gas.

The reaction is usually completed by stirring the reactants at a temperature from about −100° C. to about 100° C., preferably from about −50° C. to about 70° C. for a period from several minutes to several hours.

The compounds of the present invention can be prepared by the methods other than Method A or Method B. Such alternative methods are described below.

(Method C)

Scheme of steps

Step 1

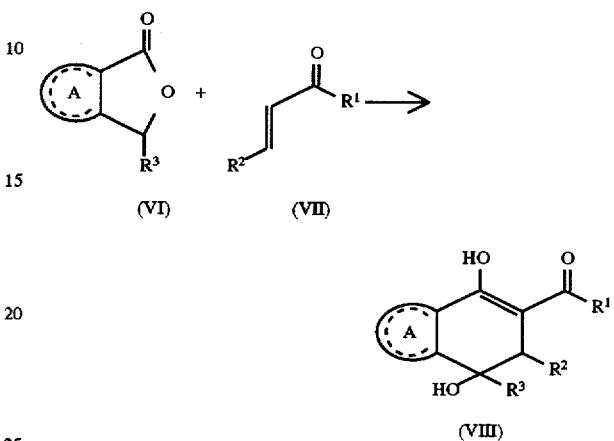

Step 2

In the first step, a lactone [VI] and an unsaturated ketone [VII] are subjected to Michael addition and then intramolecular condensation (in situ) is effected to yield Compound (VIII).

Although the ratio of Compound (VI) to Compound (VII) is not particularly limited, Compound (VII) is used in excess of Compound (VI), preferably in the ratio of 1:1 to 1:2.

The solvent includes ethers such as tetrahydrofuran, diethylether, dimethoxyethane and dioxane, aromatic solvents such as benzene, toluene and xylene, hydrocarbons such as n-hexane, n-pentane and n-heptane, halogenated hydrocarbons such as dichloromethane and dichloroethane, amides such as N,N-dimethylformamide and hexamethylphosphoric triamide, which may be employed independently or in a mixture. Preferable solvents are tetrahydrofuran, dichloromethane, dichloroethane, N,N-dimethylformamide and hexamethylphosphoric triamide.

The bases include dialkyl metal amides such as lithium diisopropylamide, sodium dicyclohexylamide and potassium diethylamide, bis(trialkylsilyl) metal amides such as lithium bis(trimethylsilyl)amide, sodium bis(trimethylsilyl) amides and potassium bis(dimethylphenylsilyl)amide as well as alkoxides such as potassium t-butoxide. A preferable base is lithium bis(trimethylsilyl)amide.

The reaction is usually completed within a period from several minutes to several hours at about −100° C. to about 100° C., preferably at about −80° C. to room temperature.

In the second step, Compound (VIII) is dehydrated by acid treatment to yield Compound (I).

The reaction solvent includes aromatic solvents such as benzene, toluene and xylene as well as halogenated hydrocarbons such as dichloromethane and chloroform.

The acid is, for example, protic acids such as hydrochloric acid, sulfuric acid, trifluoroacetic acid, and sulfonic acids (methanesulfonic acid, p-toluenesulfonic acid) and Lewis acids such as boron trifluoride and titanium tetrachloride, particularly preferred is boron trifluoride. Although the amount employed is not particularly limited, an amount of 1 to 2 equivalents is preferable.

The reaction is usually completed within a period from several minutes to several ten hours at −70° C. to 100° C., preferably at −20° C. to room temperature.

All compounds of the present invention represented by Formula (I) can be prepared by any of Method A and Method B, except for a compound of Formula (I) wherein $R^2$ is a lower alkyl or halogenated lower alkyl, or $R^1$ and $R^2$, together with adjacent carbonyl group, form cyclohexanone ring represented by the formula:

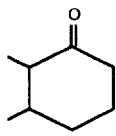

When preparing a compound of Formula (I) wherein $R^2$ is a lower alkyl or halogenated lower alkyl, a two step process as shown below is required:

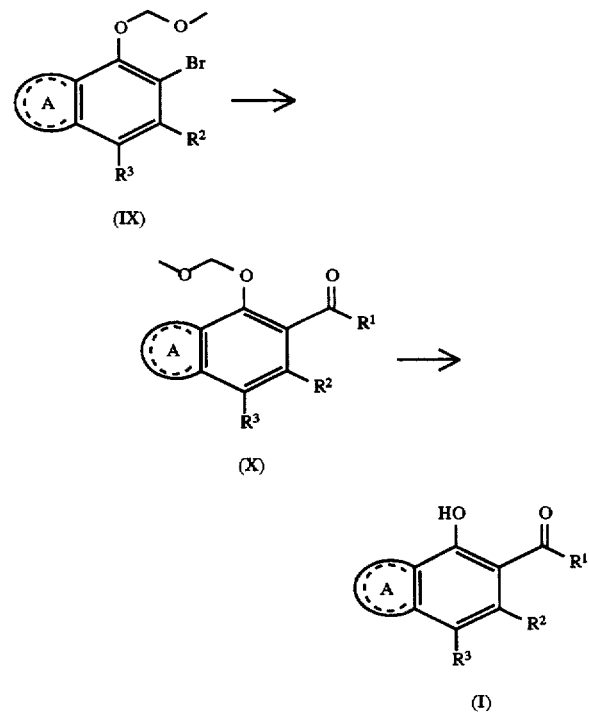

Thus, bromide (IX) which can be formed by a known method is converted into a lithium salt by using alkyl lithium, and then reacted with an acid chloride ($R^1$COCl) to yield Compound (X). Alternatively, the lithium salt can be reacted with an aldehyde ($R^1$CHO) and then oxidized to yield Compound (X). Compound (X) is deprotected to yield Compound (I).

When preparing a compound of Formula (I) wherein $R^1$ and $R^2$, together with adjacent carbonyl group, form cyclohexanone ring represented by the formula:

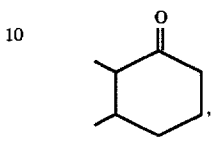

Compound (XV) of the formula:

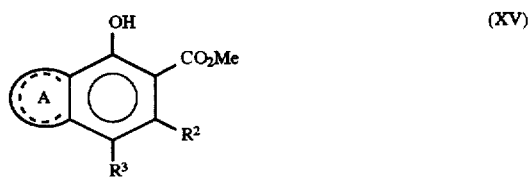

is employed as the starting material and subjected to the procedure described in Example 80 hereinafter.

The methods of preparation of the starting materials useful in the preparation of the compounds of the present invention are described below, but any other methods can also be employed to obtain each of the starting materials.

(Method of preparation of Compound (IX))

Scheme of steps

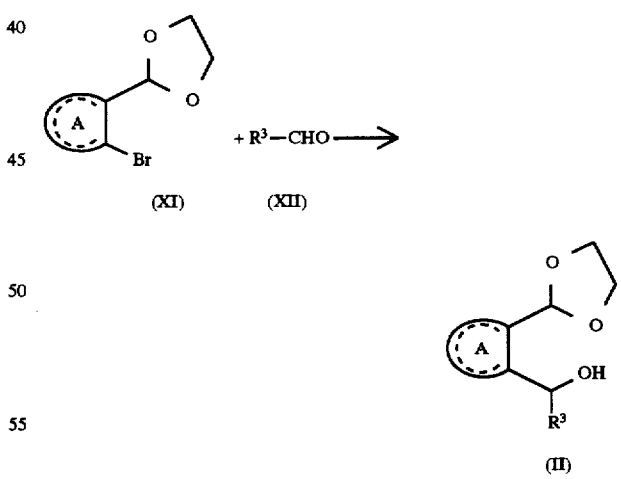

[wherein ring A and $R^3$ are defined as above.]

By reacting Compound (XII), which can be obtained by a known method or which is commercially available, with Compound (XI) synthesized according to the method by Charleton et al. (J. Org. Chem. 51, 3490 (1986)), Compound (II) can be obtained.

(Method of preparation of Compound (III))

Scheme of steps

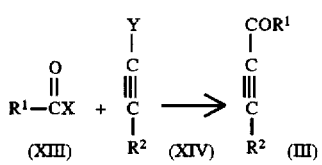

[wherein $R^1$ and $R^2$ are defined as above and X is H or Cl, and Y is Li or Ag.]

By reacting Compound (XIV, Y=Ag), according to the method by Elino et al. (Tetrahedron 38, 1579 (1982)), with Compound (XIII, X=Cl) which can be obtained by a known method, or by reacting Compound (XIV, Y=Li) with Compound (XIII, X=H) followed by oxidation, Compound III) can be obtained.

(Method of preparation of Compound (IV))

Scheme of steps

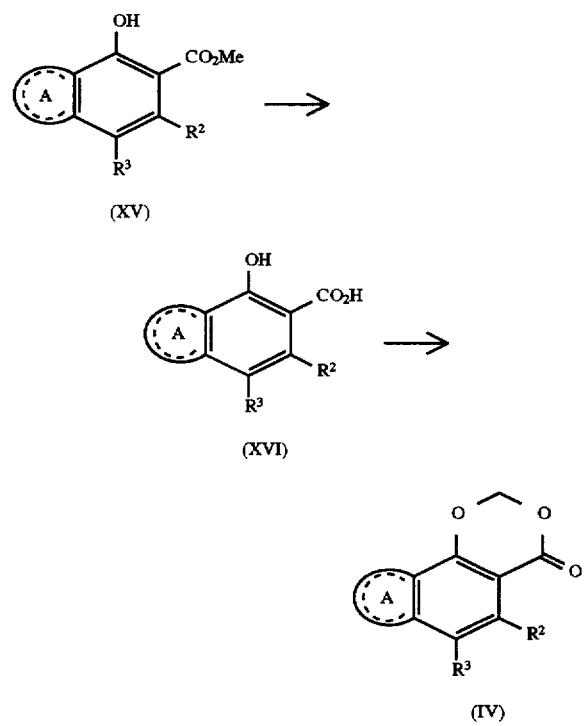

[wherein $R^2$, $R^3$ and ring A are defined as above.]

According to the method by Clark et al. (Tetrahedron Lett., 3361 (1976)), Compound (IV) can be obtained by treating Compound (XVI) which can be obtained by a known method from Compound (XV).

Although Compound (XV) can be obtained according to the method of Plaumann et al. (H. P. Plaumann, J. G. Smith and R. Rodrigo, J. Chem. Soc. Chem. Commun., 354 (1980)) from Compound (II), it can also be synthesized as disclosed in Japanese Patent Publication Nos. H1-250316 and H3-72422.

Starting materials VI and VII used in Method C can be prepared, for example, by the methods employed in Preparations 16 to 26 described below.

Compounds (I) according to the present invention and pharmaceutically acceptable salts thereof are effective as anti-hyperlipemic agents, and can be administered orally or parenterally.

When administered orally, the compounds are formulated into solid dosage forms such as tablet, powder, capsule and granule, with or without incorporating conventional additives such as excipient, binder, diluent and lubricant. The compounds are also formulated into liquid dosage forms such as aqueous or oily suspensions, solution, syrup and elixir. When administered parenterally, the compound can be formulated into a solution for injection.

Although the dose varies depending on the age, body weight, condition and severity of disease of a patient as well as administration route, suitable daily dose in adults ranges from about 0.01 to about 50 mg/kg, more preferably from about 0.1 to about 30 mg/kg.

The present invention is further illustrated by the following Preparations and Examples, which do not intend to limit the present invention in any way.

Preparation 1

Synthesis of methyl 6-ethyl-4-oxo-2-octynote: III-1
Step-1 (Synthesis of ethyl 3-ethyl-2-pentenoate: 2)

To a suspension of 4.46 g of 60% sodium hydride (112 mmol, 1.0 eq) in 150 ml of benzene was added 25.0 g (112 mmol) of diethyl ethoxycarbonylmethylphosphate under nitrogen flow and the mixture was stirred at room temperature for 1 hour. After addition of 12.4 ml of diethylketohe, the mixture was stirred for 11 hours at 60° C. Then, the mixture was diluted with saturated aqueous ammonium chloride and extracted twice with ethyl acetate. The combined extract was washed with water and brine, dried over anhydrous magnesium sulfate, and distilled under reduced pressure to yield 10.1 g of desired compound 2 (57.7%).
bp: 87°–88° C. (25 mmHg)
Step-2 (Synthesis of ethyl 3-ethylpentanoate: 3)

A solution of unsaturated ester 2 obtained above (10.0 g, 64.1 mmol) in 50 ml of ethanol was stirred in the presence of 0.65g of 10% Pd—C at room temperature for 2 hours under hydrogen atomospher. The reaction mixture was filtrated through Celite, and the filter cake was washed with 50 ml of ethanol. The filtrate and the washing were combined to obtain a solution of desired unsaturated ester 3 in ethanol, which was subjected to the next reaction directly as it is.
Step-3 (Synthesis of 3-ethylpentanoic acid: 4)

To the solution of ester 3 in ethanol obtained above was added 20 ml of 20% aqueous sodium hydroxide, and the mixture was stirred at 60° C. for 11 hours. The reaction mixture was concentrated under reduced pressure, and the residue was acidified with 100 ml of 1N hydrochloric acid and extracted twice with ethyl acetate. The combined extract was washed with water and brine, dried over anhydrous magnesium sulfate, and concentrated under reduced pressure to yield 9.50 g of compound 4 as a crude product, which was subjected to the next reaction without purification.
Step-4 (Synthesis of 3-ethylpentanoyl acid chloride: 5)

To a solution of carboxylic acid 4 obtained above in 40 ml of benzene was added 7.0 ml of thionyl chloride (2.0 eq), and the mixture was stirred at 60° C. for 2 hours. Benzene in the reaction mixture was distilled off at atmospheric pressure and then the residue was distilled under reduced pressure to obtain 7.50 g (78.5%) of desired acid chloride 5 as an oil.
bp: 66°–67° C. (25 mmHg)
Step-5 (Synthesis of methyl 6-ethyl-4-oxo-2-octynoate: III-1)

To a solution of acid chloride 5 obtained above (2.65 g, 17.8 mmol) in 50 ml of dichloroethane was added 3.07 g (16.1 mol) of methyl propiolate silver acethylide, and the mixture was heated under reflux for 18 hours. The reaction mixture was allowed to cool to room temperature and filtrated through Celite, and the filtrate was concentrated under reduced pressure. The residue was purified by column chromatography on silica gel (65 g of silica gel; Ethyl acetate:n-hexane=1:49 to 1:33) to obtain 2.24 g (70.8%) of desired compound III-1 as an oil.

$^1$H-NMR: $\delta$(CDCl$_3$) 0.88(6H,t,J=7 Hz) 1.23–1.52(4H,m) 1.83–2.02(1H,m) 2.55(2H,d,J=7 Hz) ppm.

$^{13}$C-NMR: $\delta$(CDCl$_3$) 10.8, 25.9, 37.1, 49.5, 53.5, 77.8, 81.4, 153.1, 186.7 ppm.

Preparation 2

Synthesis of methyl 4-(3,5-di-t-butyl-4-methoxymethoxy)phenyl-4-oxo-2-butynoate: III-2

Step-1 (Synthesis of 3,5-di-t-butyl-4-hydroxybenzaldehyde ethylenedioxyacetal: 7)

To a solution of 100 g (0.427 mol) of 3,5-di-t-butyl-4-hydroxybenzaldehyde (6) in 400 ml of benzene, 35 ml of ethyleneglycol and 1.0 g of p-toluenesulfonic acid were added and the mixture was heated under reflux for 2 days to effect dehydration by using Dean-Stark trap. To the reaction mixture cooled in an ice-bath, was added 1 ml of pyridine and saturated aqueous sodium bicarbonate, and the resulting mixture was extracted twice with ethyl acetate. The combined extract was washed with water and brine, dried over anhydrous magnesium sulfate, and concentrated under reduced pressure to obtain 117 g of desired compound 7 as a crude product, which was subjected to the next reaction without purification.

Step-2 (Synthesis of 3,5-di-t-butyl-4-(methoxymethoxy) benzaldehyde ethylenedioxyacetal: 8)

A solution of crude acetal 7 obtained above in 200 ml of DMF was added dropwise to a suspension of 18.8 g of 60% sodium hydride (0.470 mol, 1.1 eq) in 100 ml of DMF under cooling in an ice-bath. After completion of the addition, stirring was continued for 30 minutes and then 38.9 ml (0.513 mol, 1.2 eq) of chloromethyl methyl ether was added. After additional stirring for 1 hour at the same temperature, aqueous sodium bicarbonate was added to the mixture and DMF was distilled off under reduced pressure. To the residue was added water and the mixture was extracted twice with ethyl acetate. The combined extract was washed with water and brine, and dried over anhydrous magnesium sulfate. After concentration under reduced pressure, the residue was crystallized from n-hexane to obtain 105 g (76.2%) of desired compound 8.

mp: 107°–109° C.

Step-3 (Synthesis of 3,5-di-t-butyl-4-(methoxymethoxy) benzaldehyde: 9)

To a solution of acetal 8 obtained above (10.0 g, 30.1 mmol) in 50 ml of acetone was added 5 ml of 1N hydrochloric acid under cooling in ice-bath, and then the mixture was stirred for 50 minutes while being allowed to warm to room temperature. Saturated aqueous sodium bicarbonate was added to the reaction mixture and the mixture was extracted twice with n-hexane. The combined extract was washed with water and brine, and dried over anhydrous magnesium sulfate. After concentration under reduced pressure, the residue was crystallized from aqueous methanol to obtain 8.12 g (94.0%) of desired compound 9.

mp: 63°–64° C.

$^1$H-NMR: $\delta$(CDCl$_3$) 1.48(18H,s) 3.66(3H,s) 4.94(2H,s) 7.81(2H,s) 9.92(1H,s) ppm.

Step-4 (Synthesis of methyl 4-(3,5-di-t-butyl-4-methoxymethoxy)phenyl-4-hydroxy-2-butynoate: 10)

Under nitrogen flow, 1.78 ml (20.0 mmol) of methyl propiolate was added to a solution of lithium diisopropylamide (prepared from 3.08 ml of diisopropylamine and 14.2 ml of 1.58N n-butyllithium in n-hexane) in 60 ml of THF at −78° C. At the same temperature, the mixture was stirred for 30 minutes, and then a solution of aldehyde 9 (5.56 g, 20.0 mmol) in 20 ml of THF was added thereto dropwise. After completion of the addition, stirring was continued for 30 minutes and then to the reaction mixture was added saturated aqueous ammonium chloride and the mixture was extracted twice with ethyl acetate. The combined extract was washed with water and saturated brine and dried over anhydrous magnesium sulfate. After concentration under reduced pressure, the residue was purified by column chromatography on silica gel (100 g of silica gel; Ethyl acetate:n-hexane=1:10 to 1:3) to obtain 6.16 g (85.1%) of desired compound 10 as an oil, which was subjected to the next step without futher purification.

Step-5 (Synthesis of methyl 4-(3,5-di-t-butyl-4-methoxymethoxy)phenyl-4-oxo-2-butynoate: III-2)

To a solution of alcohol 10 obtained above (6.61 g, 17.0 mmol) in 60 ml of acetone was added dropwise 6.40 ml of 8N Jones reagent under cooling in ice-bath. Stirring was continued for 13 minutes and then 2.0 ml of isopropyl alcohol was added. The mixture was allowed to warm to room temperature while being stirred for additional 20 minutes. After concentration under reduced pressure, the residue was diluted with water and extracted twice with ether. The combined extract was washed with water and brine, dried over anhydrous magnesium sulfate, and concentrated under reduced pressure to obtain 5.91 g of desired compound III-2 as a crude oily product, which was subjected to the next step without purification.

$^1$H-NMR: $\delta$(CDCl$_3$) 1.47(18H,s) 3.66(3H,s) 3.90(3H,s) 4.94(2H,s) 8.05(2H,s) ppm.

Preparation 3

Synthesis of 2-(3,4-dimethoxy-α-hydroxybenzyl)-3,4,5-trimethoxybenzaldehyde ethylenedioxyacetal: II-1

Step-1 (Synthesis of 2-bromo-3,4,5-trimethoxybenzaldehyde ethylenedioxyacetal: XI-1)

The reaction was conducted in a procedure similar to that of step-1 in Preparation 2 using 2.25 g (30.0 mmol) of 2-bromo-3,4,5-trimethoxybenzaldehyde (11) as a starting material, to obtain 9.60 g of desired compound XI-1 as a crude oily product.

$^1$H-NMR: $\delta$(CDCl$_3$) 3.89(3H,s) 3.90(6H,s) 4.05–4.22 (4H,m) 6.05(1H,s) 7.01(1H,s) ppm.

Step-2

To a solution of 9.60 g of the crude acetal XI-1 obtained above in 120 ml of THF, 21.3 ml (33.0 mmol) 1.55N n-butyllithium in n-hexane was added dropwise at −78° C. under nitrogen flow. At the same temperature, the mixture was stirred for 30 minutes, and then 4.98 g (30.0 mmol) of 3,4-dimethoxybenzaldehyde was added thereto and the mixture was stirred for 30 minutes. Saturated aqueous ammonium chloride was added to the reaction mixture, which was then extracted twice with ethylacetate. The combined extract was washed with water and brine, dried over anhydrous magnesium sulfate, and concentrated under reduced pressure to obtain 12.8 g of desired compound II-1 as a crude oily product, which was subjected to the next reaction without purification.

Preparation 4

Synthesis of 2-(3,5-di-t-butyl-4-methoxymethoxy-α-hydroxybenzyl]-3,4,5-trimethoxybenzaldehyde ethylenedioxyacetal: II-2

Step-1

The reaction was conducted in a procedure similar to that of step-2 in Preparation 3 using acetal XI-1 (Preparation 3, Step-1) and 3,5-di-t-butyl-4-(methoxymethoxy) benzaldehyde 9 (Preparation 2, Step-3) as starting materials, to obtain desired compound (II-2) as a crude oily product, which was subjected to the next reaction without purification.

Preparation 5

Synthesis of 2-(3,4,5-trimethoxy-α-hydroxybenzyl)-3,4,5-trimethoxybenzaldehyde ethylenedioxyacetal: II-3

Step-1

The reaction was conducted in a procedure similar to that of step-2 in Preparation 3 using acetal XI-1 (Preparation 3, Step-1) and 3,4,5-trimethoxybenzaldehyde as starting materials, to obtain desired compound (II-3) as a crude oily product, which was subjected to the next step without purification.

Preparation 6

Synthesis of 2-(3,4-dimethoxy-α-hydroxybenzyl)-4,5-methylenedioxybenzaldehyde ethylenedioxyacetal: II-4

Step-1 (Synthesis of 2-bromo-4,5-methylenedioxybenzaldehyde ethylenedioxyacetal: XI-2)

The reaction was conducted in a procedure similar to that of Step-1 in Preparation 2, using 2-bromo-4,5-methylenedioxybenzaldehyde as a starting material, to obtain desired compound XI-2 as crude crystals.

$^1$H-NMR: $\delta(CDCl_3)$ 3.98–4.20(4H,m) 5.98(2H,s) 6.01(1H,s) 7.00(1H,s) 7.07(1H,s) ppm.

Step-2

The reaction was conducted in a procedure similar to that of Step-2 in Preparation 3 using acetal XI-2 obtained above and 3,4-dimethoxybenzaldehyde as starting materials, to obtain desired compound II-4 as a crude oily product.

$^1$H-NMR: $\delta(CD_3OD)$ 3.77(3H,s) 3.80(3H,s) 3.90–4.17 (4H,m) 5.91(1H,d,J=1.2 Hz) 5.93(1H,d,J=1.2 Hz) 5.97(1H, s) 6.13(1H,s) 6.85(1H,s) 6.87(1H,s) 6.88(1H,s) 6.98(1H,s) 7.02(1H,s) ppm.

Preparation 7

Synthesis of 6-(3,4-dimethoxyphenyl)-5-methoxycarbonyl-7,8,9-trimethoxy-4H-naphtho[1,2-d][1,3]dioxin-4-one: IV-1

Step-1 (Synthesis of 2,3-bis(methoxycarbonyl)-1-(3,4-dimethoxyphenyl)-4-methoxymethoxy-6,7,8-trimethoxynaphthalene: 12-1)

To a solution of 32.3 g (66.5 mmol) of 2,3-bis (methoxycarbonyl)-1-(3,4-dimethoxyphenyl)-4-hydroxy-6,7,8-trimethoxynaphthalene (XV-1) which was prepared according to the method of Japanese Patent Publication (Kokai) No. H1-250316 and 23.2 ml (133 mmol, 2.0 eq) of diisopropylethylamine in 200 ml of methylene chloride, was added 9.09 ml (120 mmol, 1.8 eq) of chloromethyl methyl ether under cooling in an ice-bath, and the mixture was allowed to warm to room temperature while being stirred for 1.5 hours. To the reaction mixture was added ice and 50 ml of 1N hydrochloric acid, and the resulting mixture was extracted with methylene chloride. The extract was washed with water, dried over anhydrous magnesium sulfate, and concentrated under reduced pressure to obtain 35.8 g of desired compound 12-1 as crude crystals, which was subjected to the next reaction without purification.

Step-2 (1-(3,4-Dimethoxyphenyl)-2-methoxycarbonyl-4-methoxymethoxy-6,7,8-trimethoxy-3-naphthoic acid: 13-1)

Aqueous potassium hydroxide (prepared from 22.4 g (399 mmol, 6.0 eq) of potassium hydroxide and 40 ml of water) was added to a solution of 35.8 g (66.5 mmol) of the crude compound 12-1 obtained above in 30 ml of dioxane and 40 ml of methanol, and the mixture was stirred for 3 days at room temperature. To the reaction mixture was added water and 50 ml of concentrated hydrochloric acid, and the resulting mixture was extracted with ethyl acetate. The extract was washed with water and brine, dried over anhydrous magnesium sulfate, and concentrated under reduced pressure to obtain 36.0 g of desired carboxylic acid 13-1 as crude crystals, which was used in the next reaction without purification.

$^1$H-NMR: $\delta(CDCl_3)$ 3.28(3H,s) 3.50(3H,s) 3.71(3H,s) 3.84(3H,s) 3.90(3H,s) 3.93(3H,s) 4.03(3H,s) 5.28(2H,s) 6.53(1H,br.s) 6.84(3H,br.s) 7.53(1H,s) ppm.

Step-3 (1-(3,4-Dimethoxyphenyl)-4-hydroxy-2-methoxycarbonyl-6,7,8-trimethoxy-3-naphthoic acid: XVI-1)

To a solution of 36.0 g (66.5 mmol) of the crude compound 13-1 obtained above and 15.0 g (99.8 mmol, 1.5 eq) of sodium iodide in 200 ml of acetonitrile, 12.7 ml (99.8 mmol, 1.5 eq) of chlorotrimethytsilane was added under ice-cooling and the mixture was stirred for 35 minutes. The reaction mixture was diluted with water and extracted with ethyl acetate. The extract was washed with water, aqueous sodium thiosulfate and brine, dried over anhydrous magnesium sulfate, and concentrated under reduced pressure. The residue was crystallized from THF-methanol to obtain 22.4 g of desired compound XVI-1 (71.4%, through 3 steps from compound XV-1).

mp: 194°–196° C.

$^1$H-NMR: $\delta(CDCl_3)$ 3.27(3H,s) 3.48(3H,s) 3.85(3H,s) 3.90,(3H,s) 3.93(3H,s) 4.03(3H,s) 6.34(1H,br.s) 6.85(3H, br.s) 7.67(1H,s) 12.24(1H,br.s) ppm.

Step-4 (Synthesis of IV-1)

To a solution of compound XVI-1 obtained above (25.0 g, 53.0 mmol) in 175 ml of DMF was added 24.2 g (150 mmol, 3.0 eq) of cesium fluoride and 21.3 g of methylene iodide (79.5 mmol, 1.5 eq) under nitrogen flow, and the mixture was stirred for 4 hours at 120° C. Ice and water were added to the reaction mixture, and the resulting mixture was extracted with ethyl acetate. The extract was washed with water, aqueous sodium thiosulfate and brine, dried over anhydrous magnesium sulfate, and concentrated under reduced pressure. The residue was crystallized from ethyl acetate-n-hexane to obtain 19.9 g (77.6%) of desired compound (IV-1).

mp: 178°–179° C.

$^1$H-NMR: $\delta(CDCl_3)$ 3.28(3H,s) 3.60(3H,s) 3.85(3H,s) 3.91(3H,s) 3.93(3H,s) 4.03(3H,s) 5.87(2H,s) 6.85(3H,br.s) 7.40(1H,s) ppm.

Preparation 8

Synthesis of 5-methoxycarbonyl-7,8,9-trimethoxy-6-(3,4,5-trimethoxyphenyl)-4H-naphtho[1,2-d][1,3]dioxin-4-one: IV-3

Step-1 (2,3-Bis(methoxycarbonyl)-4-hydroxy-6,7,8-trimethoxy-1-(3,4,5-trimethoxyphenyl)naphthalene: XV-3)

According to the method described by H. P. Plaumann, J. G. Smith and R. Rodorigo (J. Chem. Soc. Chem. Commun., 354, (1980)), 27.0 ml (220 mmol) of dimethyl acetylenedicarboxylate and 95 mg of p-toluenesulfonic acid were added to a solution of 96.0 g (200 mmol) of the crude compound II-3 (Preparation 5) in 1 liter of benzene, and the mixture was heated under reflux for 1 hour and 20 minutes. The mixture was cooled in an ice-bath and the resulting precipitates were collected by filtration and recrystallized from methanol to obtain 52.8 g (51.1%, through 3 steps from compound 11) of desired naphthalene XV-3.

mp: 165°–167° C.

$^1$H-NMR: δ(CDCl$_3$) 3.32(3H,s) 3.51(3H,s) 3.82(6H,s) 3.90(6H,s) 3.93(3H,s) 4.04(3H,s) 6.52(2H,s) 7.66(1H,s) 12.42(1H,s) ppm.

Step-2 (2,3-Bis(methoxycarbonyl)-4-methoxymethoxy-6,7,8-trimethoxy-1-(3,4,5-trimethoxyphenyl)naphthalene: 12-3)

The reaction was conducted in a procedure similar to that of Step-2 in preparation 2 using naphthalene XV-3 obtained above (20.6 g, 40.0 mmol) as a starting material, to obtain 25.6 g of desired compound 12-3 as a crude product, which was used in the next reaction without purification.

$^1$H-NMR: δ(CDCl$_3$) 3.33(3H,s) 3.50(3H,s) 3.68(3H,s) 3.82(6H,s) 3.90(9H,s) 4.03(3H,s) 5.23(2H,s) 6.53(2H,s) 7.56(1H,s) ppm Step-3 (2-Methoxycarbonyl-4-methoxymethoxy-6,7,8-trimethoxy-1-(3,4,5-trimethoxyphenyl)-3-naphthoic acid: 13-3)

The reaction was conducted in a procedure similar to that of Step-2 in preparation 7 using 25.7 g (40.0 mmol) of the crude compound 12-3 obtained above (Step-2) as a starting material, to obtain 23.3 g of desired compound 13-3 as a crude product, which was used in the next reaction without purification.

$^1$H-NMR: δ(CDCl$_3$) 3.34(3H,s) 3.52(3H,s) 3.71(3H,s) 3.82(6H,s) 3.91(6H,s) 4.04(3H,s) 5.28(2H,s) 6.53(2H,s) 7.51(1H,s) ppm.

Step-4 (4-Hydroxy-2-methoxycarbonyl-6,7,8-trimethoxy-1-(3,4,5-trimethoxyphenyl)-3-naphthoic acid: XVI-3)

The reaction was conducted in a procedure similar to that of Step-3 in preparation 7 using 23.3 g (40.0 mmol) of the crude compound 13-3 obtained above (Step-3) as a starting material, to obtain 19.4 g (96.4%, through 3 steps from Compound XV-3) of desired compound XVI-3 as crystals.

mp: 167°–171° C. (ether)

$^1$H-NMR: δ(CDCl$_3$) 3.33(3H,s) 3.51(3H,s) 3.82(6H,s) 3.91(6H,s) 4.04(3H,s) 6.53(2H,s) 7.66(1H,s) 12.35(1H,s) ppm.

Step-5 (Synthesis of IV-3)

The reaction was conducted in a procedure similar to that of Step-4 in Preparation 7 using 19.4 g (38.6 mmol) of compound XVI-3 (Step-4) as a starting material, to obtain 13.9 g (70.1%) of crystalline compound IV-3.

mp: 225°–228° C. (acetone)

$^1$H-NMR: δ(CDCl$_3$) 3.34(3H,s) 3.62(3H,s) 3.82(6H,s) 3.91(3H,s) 3.92(3H,s) 4.04(3H,s) 5.87(2H,s) 6.53(2H,s) 7.40(1H,s) ppm.

Preparation 9

Synthesis of 6-(3,4-dimethoxyphenyl)-5-methoxycarbonyl-8,9-methylenedioxy-4H-naphtho[1,2-d][1,3]dioxin-4-one: IV-4

Step-1 (Synthesis of 2,3-bis(methoxycarbonyl)-1-(3,4-dimethoxyphenyl)-4-hydroxy-6,7-methylenedioxynaphthalene: XV-4)

The reaction was conducted in a procedure similar to that of Step-1 in Preparation 8 using 16.7 g (36.3 mmol) off compound II-4 (Preparation 6) as a starting material, to obtain 14.1 g (69.2%) of desired compound XV-4 as crystals.

mp: 168°–170° C. (methanol)

$^1$H-NMR: δ(CDCl$_3$) 3.56(3H,s) 3.85(3H,s) 3 93(3H,s) 3.95(3H,s) 6.06(2H,s) 6.74–6.97(4H,m) 7.75(1H,s) 12.23 (1H,s) ppm.

Step-2 (Synthesis of 2,3-bis(methoxycarbonyl)-1-(3,4-dimethoxyphenyl)-4-methoxymethoxy-6,7-methylenedioxynaphthalene: 12-4)

The reaction was conducted in a procedure similar to that of Step-2 in Preparation 2 using 4.40 g (10.0 mmol) of naphthalene XV-4 obtained above (Step-1) as a starting material, to obtain 5.02 g of desired compound 12-4 as crude crystals, which was used in the next reaction without purification.

$^1$H-NMR: δ(CDCl$_3$) 3.55(3H,s) 3.65(3H,s) 3.85(3H,s) 3.91(3H,s) 3.95(3H,s) 5.21(2H,s) 6.07(2H,s) 6.78–6.98(4H, m) 7.61(1H,s) ppm.

Step-3 (1-(3,4-Dimethoxyphenyl)-2-methoxycarbonyl-4-methoxymethoxy-6,7-methylenedioxy-3-naphthoic acid: 13-4)

The reaction was conducted in a procedure similar to that of Step-2 in Preparation 7 using 5.02 g (10.0 mmol) of the crude compound 12-4 (Step-2) as a starting material, to obtain 4.65 g of desired compound 13-4 as crude crystals, which was used in the next reaction without purification.

Step-4 (1-(3,4-Dimethoxyphenyl)-4-hydroxy-2-methoxycarbonyl-6,7-methylenedioxy-3-naphthoic acid: XVI-4)

The reaction was conducted in a procedure similar to that of Step-3 in Preparation 7 using 4.65 g (10.0 mmol) of the crude compound 13-4 (Step-3) as a starting material, to obtain 3.48 g (81.8%, through 3 steps from compound XV-4) of desired compound XVI-4 as crystals.

mp: 187°–192° C. (ethter)

$^1$H-NMR: δ(CDCl$_3$+CD$_3$OD) 3.55(3H,s) 3.85(3H,s) 3.95 (3H,s) 6.06(2H,s) 6.76(1H,s) 6.80–6.98(3H,m) 7.74(1H,s) ppm.

Step-5 (Synthesis of IV-4)

The reaction was conducted in a procedure similar to that of Step-4 in Preparation 7 using 4.51 g (10.6 mmol) of compound XVI-4 (Step-4) as a starting material to obtain 3.38 g (72.8%) of compound IV-4 as crystals.

mp: 272°–275° C. (acetone)

$^1$H-NMR: δ(CDCl$_3$) 3.67(3H,s) 3.86(3H,s) 3.95(3H,s) 5.86(2H,s) 6.11(2H,s) 6.82–7.00(4H,m) 7.52(1H,s) ppm.

Preparation 10

Synthesis of 6-(3,4-dimethoxyphenyl)-5-methoxycarbonyl-4H-[1]benzothieno[4,5-d][1,3]dioxin-4-one: IV-5

Step-1 (5,6-Bis(methoxycarbonyl)-7-(3,4-dimethoxyphenyl)-4-(methoxymethoxy)benzo[b]thiophene: 12-5)

The reaction was conducted in a procedure similar to that of Step-2 in Preparation 2 using 4.71 g (11.7 mmol) of 5,6-bis(methoxycarbonyl)-4-hydroxy-7-(3,4-dimethoxyphenyl)benzo[b]thiophene (XV-5) which was obtained according to the method described in Japanese Patent Publication (Kokai) No. H3-72422 as a starting material, to obtain 5.90 g of desired compound 12-5 as a crude product, which was used in the next reacion without purification.

$^1$H-NMR: δ(CDCl$_3$) 3.61(3H,s) 3.65(3H,s) 3.87(3H,s) 3.92(3H,s) 3.95(3H,s) 5.26(2H,s) 6.91–7.06(3H,m) 7.56 (1H,d,J=5.6 Hz) 7.61(1H,d,J=5.6 Hz) ppm.

Step-2 (7-(3,4-Dimethoxyphenyl)-6-methoxycarbonyl-4-(methoxymethoxy)benzo[b]thiophen-5-carboxylic acid: 13-5)

The reaction was conducted in a procedure similar to that of Step-2 in Preparation 7 using 5.90 g (11.7 mmol) of the crude compound 12-5 (Step-1) as a starting material, to obtain 5.16 g of desired compound 13-5 as a crude product, which was used in the next reaction without purification.

¹H-NMR: δ(CDCl₃) 3.65(3H,s) 3.68(3H,s) 3.88(3H,s) 3.95(3H,s) 5.34(2H,s) 6.95–7.07(3H,m) 7.60(2H,s) ppm.

Step-3 (7-(3,4-Dimethoxyphenyl)-4-hydroxy-6-(methoxycarbonyl)benzo[b]thiophen-5-carboxylic acid: XVI-5)

The reaction was conducted in a procedure similar to that of Step-3 in Prepration 7 using 5.16 g (11.7 mmol) of the crude compound 13-5 (Step-2) as a starting material, to obtain 2.72 g (59.8%, through 3 steps from compound XV-5) of desired compound XVI-5 as crystals.

mp: 180°–186° C. (methanol)

¹H-NMR: δ(CDCl₃+CD₃OD) 3.63(3H,s) 3.87(3H,s) 3.95 (3H,s) 6.90–7.10(3H,m) 7.44(1H,d,J=5.6 Hz) 7.68(1H,d,J= 5.6 Hz) ppm.

Step-4 (Synthesis of IV-5)

The reaction was conducted in a procedure similar to that of Step-4 in Preparation 7 using 2.72 g (7.01 mmol) of compound XVI-5 (Step-3) as a starting material, to obtain 2.35 g (83.8%) of compound IV-5 as crystals.

mp: 215°–216° C. (methanol)

¹H-NMR: δ(CDCl₃) 3.74(3H,s) 3.88(3H,s) 3.95(3H,s) 5.85(2H,s) 6.93–7.10(3H,m) 7.59(2H,s) ppm.

Example 1

Synthesis of 1-(3,4-dimethoxyphenyl)-3-(3-ethyl-1-oxopentyl)-4-hydroxy-2-methoxycarbonyl-6,7,8-trimethoxynaphthalene: Compound I-1

(Method A):

To a solution of 2.23 g (11.4 mmol) of acetylene III-1 (Preparation 1) and 4.63 g (11.4 mmol) of compound II-1 (Preparation 3) in 100 ml of benzene was added 13 mg of p-toluenesulfonic acid, and the mixture was heated under reflux for 1 hour. The reaction mixture was concentrated under reduced pressure. The residue was purified by medium pressure column chromatography on silica gel (500 g of silica gel; ethyl acetate:methylene chloride=1:20), which was followed by crystallization from diisopropyl ether to give 1.84 g (29.8%) of desired compound I-1.

(Method B):

Under argon atmosphere, 43.0 ml of 0.70M (2-ethyl) butylmagnesium bromide in THF (30.1 mmol, 3.01 eq) was added dropwise over 10 minutes to a solution of 4.84 g (10.0 mmol) of compound IV-1 (Preparation 7) in 150 ml of methylene chloride under cooling in an ice-bath, and the mixture was stirred at the same temperature for 30 minutes. The reaction mixture was quenched with saturated aqueous ammonium chloride and extracted with methylene chloride. The extract was dried over anhydrous magnesium sulfate and gel (150 g of silica gel; ethyl acetate:n-hexane=1:2), concentrated under reduced pressure. The residue was purified by medium pressure column chromatography on silica which was followed by crystallization from ethyl acetate-n-hexane to give 3.40 g (57.1%) of desired compound I-1. The physical properties of compound I-1 thus obtained were same as those of the compound obtained by Method A.

Examples 2–10

Example 2:

3-Acetyl-1-(3,4-dimethoxyphenyl)-4-hydroxy-2-methoxycarbonyl-6,7,8-trimethoxynaphthalene The reaction was conducted in a procedure similar to that of Method B in Example 1 using methylmagnesium bromide, to obtain the title compound.

Example 3:

1-(3,4-Dimethoxyphenyl)-4-hydroxy-2-methoxycarbonyl-3-(2-methyl-1-oxopropyl)-6,7,8-trimethoxynaphthalene The reaction was conducted in a procedure similar to that of Method B in Example 1 using isopropylmagnesium bromide, to obtain the title compound.

Example 4:

1-(3,4-Dimethoxyphenyl)-3-(2-ethyl-1-oxobutyl)-4-hydroxy-2-methoxycarbonyl-6,7,8-trimethoxynaphthalene The reaction was conducted in a procedure similar to that of Method B in Example 1 using 1-ethylpropylmagnesium bromide, to obtain the title compound.

Example 5:

3-Cyclohexanoyl-1-(3,4-dimethoxyphenyl)-4-hydroxy-2-methoxycarbonyl-6,7,8-trimethoxynaphthalene The reaction was conducted in a procedure similar to that of Method B in Example 1 using cyclohexylmagnesium bromide, to obtain the title compound.

Example 6:

3-Benzoyl-1-(3,4-dimethoxyphenyl)-4-hydroxy-2-methoxycarbonyl-6,7,8-trimethoxynaphthalene The reaction was conducted in a procedure similar to that of Method B in Example 1 using phenylmagnesium bromide, to obtain the title compound.

Example 7:

3-(2-Cyclohexyl-1-oxoethyl)-1-(3,4-dimethoxyphenyl)-4-hydroxy-2-methoxycarbonyl-6,7,8-trimethoxynaphthalene The reaction was conducted in a procedure similar to that of Method B in Example 1 using cyclohexylmexhylmagnesium bromide, to obtain the title compound.

Example 8:

1-(3,4-Dimethoxyphenyl)-4-hydroxy-2-methoxycarbonyl-3-(2-phenyl-1-oxoethyl)-6,7,8-trimethoxynaphthalene The reaction was conducted in a procedure similar to that of Method B in Example 1 using benzylmagnesium bromide, to obtain the title compound.

Example 9:

1-(3,4-Dimethoxyphenyl)-4-hydroxy-2-methoxycarbonyl-3-[2-(4-methoxyphenyl)-1-oxoethyl]-6,7,8-trimethoxynaphthalene The reaction was conducted in a procedure similar to that of Method B in Example 1 using 4-methoxyphenylmethylmagnesium bromide, to obtain the title compound.

Example 10:

3-[(3,5-Diisopropyl-4-hydroxy)benzoyl]-1-(3,4-dimethoxyphenyl)-4-hydroxy-2-methoxycarbonyl-6,7,8-trimethoxynaphthalene The reaction was conducted in a procedure similar to that of Method B in Example 1 using 3,5-diisopropyl-4-(methoxymethoxy)phenylmagnesium bromide, which was followed by deprotection of methoxymethyl ether to obtain the title compound.

Table 1 shows the structures of the compounds of Examples described above, and Table 2 and Table 3 show the physical properties thereof.

TABLE 1

[Structure: naphthalene with HO, MeO, MeO, MeO substituents, C(O)R¹, CO₂Me, and 3,4-dimethoxyphenyl group]

| Example No. | R¹ |
|---|---|
| 1 | —CH₂CHEt₂ |
| 2 | —Me |
| 3 | —CHMe₂ |
| 4 | —CHEt₂ |
| 5 | 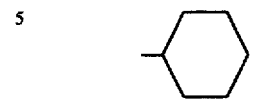 |
| 6 | 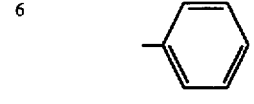 |
| 7 | 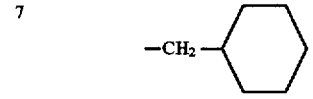 |

TABLE 1-continued

[Structure: naphthalene with HO, MeO, MeO, MeO substituents, C(O)R¹, CO₂Me, and 3,4-dimethoxyphenyl group]

| Example No. | R¹ |
|---|---|
| 8 | 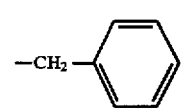 |
| 9 | 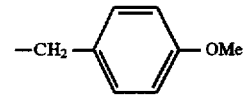 |
| 10 | 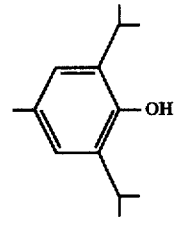 |

TABLE 2

| Example No. | mp (°C.) | ¹H—NMR δ (CDCl₃) ppm | I R ν max (cm⁻¹) |
|---|---|---|---|
| 1 | 129–130 (isopropyl ether) | 0.83 (6H, t, J = 7 Hz) 1.20–1.42 (4H, m) 1.96–2.12 (1H, m) 2.73 (2H, d, J = 6 Hz) 3.25 (3H, s) 3.44 (3H.s) 3.86 (3H, s) 3.89 (3H, s) 3.93 (3H, s) 4.04 (3H, s) 6.78–6.90 (3H, m) 7.73 (1H, s) 14.38 (1H, s) | (CHCl₃) 2968, 1729, 1606, 1576, 1514, 1489, 1464, 1412, 1139, 1064, 1028 |
| 2 | 151–152 (ethyl acetate-isopropyl ether) | 2.55 (3H, s) 3.25 (3H, s) 3.46 (3H, s) 3.86 (3H, s) 3.90 (3H, s) 3.93 (3H, s) 4.03 (3H, s) 6.8–6.85 (3H, m) 7.7 3 (1H, s) 14.70 (1H, s) | (nujol) 1725, 1605, 1574, 1513, 1412, 1220, 1128, 1024, 840 |
| 3 | 106–107 (isopropyl ether-n-hexane) | 1.15 (3H, d, J = 7 Hz) 1.16 (3H, d, J = 7 Hz) 3.09–3.20 (1H, m) 3.24 (3H, s) 3.43 (3H, s) 3.86 (3H, 5) 3.89 (3H, s) 3.93 (3H, s) 4.03 (3H, s) 6.79–6.90 (3H, m) 7.71 (1H, s) 13.76 (1H, s) | (nujol) 1724, 1604, 1579, 1510, 1410, 1195, 1133, 1104, 1024, 988, 959, 843 |
| 4 | 98–99 (isopropyl ether-petroleum ether) | 0.82 (3H, t, J = 8 Hz) 0.83 (3H, t, J = 8 Hz) 1.42–1.60 (2H, m) 1.64–1.81 (2H, m) 2.78–2.90 (1H, m) 3.24 (3H, s) 3.42 (3H, s) 3.86 (3H, 2) 3.89 (3H, s) 3.93 (3H, s) 4.03 (3H, s) 6.81–6.87 (3H, m) 7.72 (1H, s) 14.18 (1H, s) | (nujol) 1714, 1606, 1580, 1516, 1489, 1410, 1240, 1199, 1138, 1061, 1027 |
| 5 | 150–151 (isopropyl ether) | 1.15–1.90 (10H, m) 2.70–2.90 (1H, m) 3.24 (3H, s) 3.44 (3H, s) 3.86 (3H, s) 3.89 (3H, s) 3.93 (3H, s) 4.03 (3H, s) 6.81–6.87 (3H, m) 7.71 (1H, s) 13.99 (1H, s) | (nujol) 1714, 1606, 1582, 1516, 1489, 1410, 1240, 1197, 1142, 1107, 1063, 1027, 1004 |

TABLE 3

| Example No. | mp (°C.) | $^1$H—NMR δ (CDCl$_3$) ppm | I R ν max (cm$^{-1}$) |
|---|---|---|---|
| 6 | 139~140 (ethyl acetate-isopropyl ether) | 2.71 (3H, s) 3.24 (3H, s) 3.83 (3H, s) 3.89 (3H, s) 3.91 (3H, s) 4.06 (3H, s) 6.78~6.83 (3H, m) 7.34~7.68 (5H, m)7.41 (1H, s) 12.44 (1H, s) | (nujol) 1727, 1598, 1573, 1509, 1486, 1409, 1213, 1125, 1049, 1022 |
| 7 | 119~120 (ethyl acetate-isopropyl ether) | 0.81~1.40 (4H, m) 1.55~1.68 (6H, m) 1.85~2.10 (1H, m) 2.67 (2H, d, J = 7 Hz) 3.25 (3H, s) 3.44 (3H, s) 3.86 (3H, s) 3.89 (3H, s) 3.93 (3H, s) 4.03 (3H, s) 6.80~6.88 (3H, m) 7.73 (1H, s) 14.41 (1H, s) | (nujol) 1721, 1614, 1600, 1568, 1515, 1484, 1405, 1241, 1134, 1022, 982, 917 |
| 8 | 171~173 (dichloromethane-isopropyl ether) | 3.26 (3H, s) 3.46 (3H, s) 3.88 (3H, s) 3.90 (3H, s) 3.94 (3H, s) 4.02 (3H, s) 4.17 (2H, s) 6.83~6.90 (3H, m) 7.2 0~7.40 (5H, m) 7.72 (1H, s) 14.24 (1H, s) | (nujol) 1720, 1618, 1601, 1581, 1515, 1490 1413, 1240, 1197, 1141, 1102, 1060, 1023 |
| 9 | 85~87 (ethyl acetate-ether) | 3.26 (3H, s) 3.46 (3H, s) 3.80 (3H, s) 3.87 (3H, s) 3.90 (3H, s) 3.94 (3H, s) 4.02 (3H, s) 4.11 (2H, s) 6.80~6.9 3 (5H, m) 7.11 (2H, d, J = 8 Hz) 7.72 (1H, s) 14.25 (1H, s) | (nujol) 1739, 1716, 1610, 1581, 1514, 1489, 1413, 1247, 4198, 1133, 1103, 1060 , 1022 |
| 10 | 114~115 (ethyl acetate-ether) | 1.24 (6H, d, J = 7 Hz) 1.26 (6H, d, J = 7 Hz) 2.79 (3H, s) 3.06~3.20 (2H, s) 3.26 (3H, s) 3.82 (3H, s) 3.89 (3H, s) 3.90 (3H, s) 3.9 (3H, s) 4.06 (3H, s) 5.26 (1H, br. s) 6.72~6.81 (2H, m) 6.86 (1H, d, J = 1.5 Hz) 7.40 (2H, s) 7.72 (1H, s) 11.87 (1H, s) | (nujol) 3442, 1742 1713, 1581, 1202, 1133, 1055, 1026 |

Example 11

Synthesis of 3-(3-ethyl-1-oxopentyl)-4-hydroxy-2-methoxycarbonyl-6,7,8-trimethoxy-1-(3,4,5-trimethoxyphenyl)naphthalene The reaction was conducted in a procedure similar to that of Method B in Example 1 using compound of Formula IV-3 (Preparation 8), to obtain the title compound.

Example 12

Synthesis of 1-(3,5-di-t-butyl-4-hydroxy)phenyl-3-(3-ethyl-1-oxopentyl)-4-hydroxy-2-methoxycarbonyl-6,7,8-trimethoxynaphthalene Step-1 (1-(3,5-Di-t-butyl-4-methoxymethoxy)phenyl-3-(3-ethyl-1-oxopentyl)-4-hydroxy-2-methoxycarbonyl-6,7,8-trimethoxynaphthalene: 14)

The reaction similar to that of Method A in Example 1 was conducted using 4.11 g (20.9 mmol) of acetylene III-1 (Preparation 1) and 11.9 g (22.8 mmol) of compound II-2 (Preparation 4), to obtain 11.0 g (80.7%) of a mixture of desired compound 14 and structural isomer 15 thereof, which was subjected to the next step without separation.

Step-2

The reaction similar to that of Step-3 in Preparation 7 was conducted using 11.0 g (16.8 mmol) of the mixture of compound 14 and compound 15 (Step-1) to obtain 4.50 g (35.3%) of desired compound as crystals.

Example 13

Synthesis of 3-(3,5-di-t-butyl-4-hydroxy)benzoyl-1-(3,5-di-t-butyl-4-hydroxy)phenyl-4-hydroxy-2-methoxycarbonyl-6,7,8-trimethoxynaphthalene Step-1 (3-(3,5-Di-t-butyl-4-methoxymethoxy)benzoyl-1-(3, 5-di-t-butyl-4-methoxymethoxy)phenyl-4-hydroxy-2-methoxycarbonyl-6,7,8-trimethoxynaphthalene: 16)

The reaction similar to that of Method A in Example 1 was conducted using 5.91 g (16.4 mmol) of acetylene III-2 (Preparation 2) and 9.84 g (19.0 mmol, 1.16 eq) of compound II-2 (Preparation 4) to obtain 1.71 g (12.8%) of desired compound 16 as an oil.

$^1$H-NMR: δ(CDCl$_3$) 1.40(18H,s) 1.41(18H,s) 2.69(3H,s) 3.14(3H,s) 3.64(3H,s) 3.65(3H,s) 3.91(3H,s) 4.06(3H,s) 4.86(2H,s) 4.87(2H,s) 7.09(2H,s) 7.54(2H,s) 7.72(1H,s) 12.10(1H,s) ppm.

Step-2

The reaction similar to that of Step-3 in Preparation 7 was conducted using 1.71 g (2.09 mmol) of compound 16 (Step-1) to obtain 1.02 g (66.8%) of desired compound as crystals.

Example 14

Synthesis of 1-(3,4-dimethoxyphenyl)-3-(3-ethyl-1-oxopentyl)-4-hydroxy-2-methoxycarbonyl-6,7-methylenedioxynaphthalene The reaction similar to that of Method A in Example 1 was conducted using 21.6 g (1.10 mmol) of acetylene III-1 (Preparation 1) and 360 mg (1.00 mmol) of compound II-4 (Preparation 6) to obtain 116 mg (23.5%) of desired compound as crystals.

The reaction similar to that of Method B in Example 1 was conducted using compound IV-4 (Preparation 9) to obtain desired compound, which was identical to that obtained in Method A.

Example 15

7-(3,4-Dimethoxyphenyl)-5-(3-ethyl-1-oxopentyl)-4-hydroxy-6-(methoxycarbonyl)benzo[b]thiophene The reaction similar to that of Method B in Example 1 was conducted using compound IV-5 (Preparation 10) to obtain desired compound.

Table 4 shows the structures of the compounds of Examples described above, and Table 5 shows the physical properties therof.

TABLE 4

(I) Structure: A ring fused with benzene bearing HO, C(O)R¹, CO₂Me, and R³ substituents.

| Example No. | R¹ | R³ | A ring |
|---|---|---|---|
| 11 | —CH₂CHEt₂ | 2,6-dimethoxy-4-methylphenyl (OMe, OMe, OMe substituted) | MeO, MeO, MeO substituted benzene |
| 12 | —CH₂CHEt₂ | 3,5-di-tert-butyl-4-hydroxyphenyl | |
| 13 | 3,5-di-tert-butyl-4-hydroxyphenyl | | |
| 14 | —CH₂CHEt₂ | 3,4-dimethoxyphenyl | methylenedioxybenzene |
| 15 | —CH₂CHEt₂ | 3,4-dimethoxyphenyl | thiophene |

TABLE 5

| Example No. | mp (°C.) | ¹H—NMR δ (CDCl₃) ppm | IR ν max (cm⁻¹) |
|---|---|---|---|
| 11 | 99–1.02 (ether-n-pentane) | 0.83 (6H, t, J = 7 Hz) 1.20–1.42 (4H, m) 1.98–2.13 (1H, nr) 2, 73 (2H, d, J = 6 Hz) 3.31 (3H, s) 3.47 (3H, s) 3.83 (6 H, s) 3.90 (6H, s) 4.04 (3H, s) 6.53 (2H, s) 7.73 (1H, s) 14.40 (1H, s) | (CHCl₃) 2960, 2940, 1725, 1600, 1583, 1487, 1460, 1432, 1401, 1379, 1126, 1070 |
| 12 | 119–120 (methanol-water) | 0.83 (6H, t, J = 7 Hz) 1.20–1.40 (4H, m) 1.44 (18H, s) 1, 98–2.13 (1H, m) 2.74 (2H, d, J = 6 Hz) 3.13 (3H, s) 3.34 ( 3H, s) 3.89 (3H, s) 4.03 (3H, s) 5.14 (1H, s) 7.04 (2H, s ) 7.72 (1H, s) 14.41 (1H, s) | (CHCl₃) 3604, 2968, 4721, 1606, 1574, 1489, 1464, 1435, 1413, 1380, 1071 |
| 13 | 267–274 (dichloromethane-methanol-water) | 1.40 (18H, s) 1.41 (18H, s) 2.70 (3H, s) 3.16 (3H, s) 3, 92 (3H, s) 4.05 (3H, s) 5.07 (1H, s) 5.65 (1H, s) 6.72 (2 H, s) 7.52 (2H, s) 7.71 (1H, s) 12.01 (1H, s) | (CHCl₃) 3658, 2968, 1742, 1711, 1607, 1587, 1490, 1464, 1435, 1414 1375, 1069 |
| 14 | 124–126 (ether-n-pentane) | 0.83 (6H, t, J = 7 Hz) 1.20–1.42 (4H, m) 1.96–2.16 (1H, m) 2.73 (2H, d, J = 7 Hz) 3.51 (3H, s) 3.86 (3H, 5) 3.96 (3 H, s) 6.06 (2H, s), 6.72–6..98 (4H, m) 7.81 (1H, s) 14.17 (1H, s) | (CHCl₃) 2975, 1730, 1623, 1610, 1586, 1517, 1463, 1176, 1142, 1043, 1028, 945 |

TABLE 5-continued

| Example No. | mp (°C.) | $^1$H—NMR δ (CDCl$_3$) ppm | I R ν max (cm$^{-1}$) |
|---|---|---|---|
| 15 | 84–86 (ether-n-pentane) | 0.83 (6H, t, J = 7 Hz) 1.20–1.42 (4H, m) 1.97–2.15 (1H, m) 2.74 (2H, d, J = 7 Hz) 3.59 (3H, s) 3.88 (3H, s) 3.95 (3 H, s) 6.92–6.99 (3H, m) 7.45 (1H, d, J = 6 Hz) 7.72 (1H, d J = 6 Hz) 13.34 (1H, s) | (CHCl$_3$) 2960, 1728, 1625, 1586, 1513, 1462, 1435, 1416, 1174.1139, 1091, 1077, 1042, 1023 |

Examples 16 to 30

Example 16:

1-(3,4-Dimethoxyphenyl)-4-hydroxy-2-methoxycarbonyl-3-(1-oxopropyl)-6,7,8-trimethoxynaphthalene By the reaction of Method B in Example 1 except for using ethyl magnesium bromide, the title compound was obtained from compound IV-1.

Example 17:

1-(3,4-Dimethoxyphenyl)-4-hydroxy-2-methoxycarbonyl-3-(2-methylbenzoyl)-6,7,8-trimethoxynaphthalene By the reaction of Method B in Example 1 except for using 2-methylphenylmagnesium bromide, the title compound was obtained from compound IV-1.

Example 18:

1-(3,4-Dimethoxyphenyl)-4-hydroxy-2-methoxycarbonyl-3-(3-methylbenzoyl)-6,7,8-trimethoxynaphthalene By the reaction of Method B in Example 1 except for using 3-methylphenylmagnesium bromide, the title compound was obtained from compound IV-1.

Example 19:

1-(3,4-Dimethoxyphenyl)-4-hydroxy-2-methoxycarbonyl-3-(4-methylbenzoyl)-6,7,8-trimethoxynaphthalene By the reaction of Method B in Example 1 except for using 4-methylphenylmagnesium bromide, the title compound was obtained from compound IV-1.

Example 20:

1-(3,4-Dimethoxyphenyl)-4-hydroxy-3-(2-methoxybenzoyl)-2-methoxycarbonyl-6,7,8-trimethoxynaphthalene By the reaction of in Method B in Example 1 except for using 2-methoxyphenylmagnesium bromide, the title compound was obtained from compound IV-1.

Example 21:

1-(3,4-Dimethoxyphenyl)-4-hydroxy-3-(3-methoxybenzoyl)-2-methoxycarbonyl-6,7,8-trimethoxynaphthalene By the reaction of Method B in Example 1 except for using 3-methoxyphenylmagnesium bromide, the title compound was obtained from compound IV-1.

Example 22:

1-(3,4-Dimethoxyphenyl)-4-hydroxy-3-(4-methoxybenzoyl)-2-methoxycarbonyl-6,7,8-trimethoxynaphthalene By the reaction of Method B in Example 1 except for using 4-methoxyphenylmagnesium bromide, the title compound was obtained from compound IV-1.

Example 23:

3-(4-Chlorobenzoyl)-1-(3,4-dimethoxyphenyl)-4-hydroxy-2-methoxycarbonyl-6,7,8-trimethoxynaphthalene By the reaction of Method B in Example 1 except for using 4-chlorophenylmagnesium bromide, the title compound was obtained from compound IV-1.

Example 24:

3-(3,4-Dimethoxybenzoyl)-1-(3,4-dimethoxyphenyl)-4-hydroxy-2-methoxycarbonyl-6,7,8-trimethoxynaohthalene By the reaction of Method B in Example 1 except for using 3,4-dimethoxyphenylmagnesium bromide, the title compound was obtained from compound IV-1.

Example 25:

1-(3,4-Dimethoxyphenyl)-4-hydroxy-2-methoxycarbonyl-3-(2-naphthoyl)-6,7,8-trimethoxynaphthalene By the reaction of Method B in Example 1 except for using 2-naphthylmagnesium bromide, the title compound was obtained from compound IV-1.

Example 26:

1-(3,4-Dimethoxyphenyl)-3-(4-fluorobenzoyl)-4-hydroxy-2-methoxycarbonyl-6,7,8-trimethoxynaphthalene By the reaction of Method B in Example 1 except for using 4-fluorophenylmagnesium bromide, the title compound was obtained from compound IV-1.

Example 27:

3-(2,4-Difluorobenzoyl)-1-(3,4-dimethoxyphenyl)-4-hydroxyl-2-methoxycarbonyl-6,7,8-trimethoxynaphthalene By the reaction of Method B in Example 1 except for using 2,4-difluorophenylmagnesium bromide, the title compound was obtained from compound IV-1.

Example 28:

1-(3,4-Dimethoxyphenyl)-4-hydroxy-2-methoxycarbonyl-3-[4-(trifluoromethyl)benzoyl]-6,7,8-trimethoxynaphthalene By the reaction of Method B in Example 1 except for using 4-(trifluoromethyl)phenylmagnesium bromide, the title compound was obtained from compound IV-1.

Example 29:

1-(3,4-Dimethoxyphenyl)-4-hydroxy-2-methoxycarbonyl-3-[4-(1-propyl)benzoyl]-6,7,8-trimethoxynaphthalene By the reaction of Method B in Example 1 except for using 4-(n-propyl)phenylmagnesium bromide, the title compound was obtained from compound IV-1.

Example 30:

3-[4-(t-Butyl)benzoyl]-1-(3,4-dimethoxyphenyl)-4-hydroxy-2-methoxycarbonyl-6,7,8-trimethoxynaphthalene By the reaction of Method B in Example 1 except for using 4-(t-butyl)phenylmagnesium bromide, the title compound was obtained from compound IV-1.

Table 6 shows the structures of the compounds of Examples described above, and Tables 7, 8 and 9 show the physical properties thereof.

TABLE 6

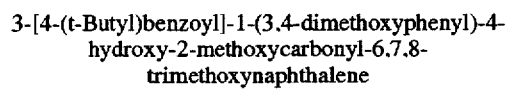

| Example No. | |
|---|---|
| 16 | R=Et |
| 17 | R = o-tolyl (Me) |
| 18 | R = m-tolyl (Me) |
| 19 | R = p-tolyl (Me) |
| 20 | R = 2-MeO-phenyl |
| 21 | R = 3-MeO-phenyl |
| 22 | R = 4-MeO-phenyl |

TABLE 6-continued

| Example No. | |
|---|---|
| 23 | R = 4-Cl-phenyl |
| 24 | R = 3,4-(OMe)$_2$-phenyl |
| 25 | R = 2-naphthyl |
| 26 | R = 4-F-phenyl |
| 27 | R = 2,4-F$_2$-phenyl |
| 28 | R = 4-CF$_3$-phenyl |
| 29 | R = 4-Pr$^n$-phenyl |
| 30 | R = 4-t-Bu-phenyl |
| 31 | R=—CF$_2$F$_5$ |

TABLE 7

| Exam. No. | mp (°C.) | ¹H—NMR δ (CDCl₃) ppm | I R ν max (cm⁻¹) |
|---|---|---|---|
| 16 | 145~146 (ethyl acetate-isopropyl-ether) | 1.18 (3H, t, J = 7.2 Hz) 2.81~2.91 (2H, m) 2.25 (3H, s) 3.45 (3H, s) 3.86 (3H, s) 3.89 (31H, s) 3.93 (3H, s) 4.03 (3H, s) 6.80~6.85 (3H, m) 7.74 (1H, s) (1H, s) | (nujol) 1730, 1604, 1577, 1202, 1117, 1023 14.60 |
| 17 | 159~160 (methylene chloride-isopropyl ether) | 2.40 (3H, s) 2.65 (3H, s) 3.23 (3H, s) 3.81 (3H, s) 3.87 (3H, s) 3.91 (3H, s) 4.06 (3H, s) 6.77 (3H, br. s) 7.08~7.35 (4H, m) 7.77 (1H, s) 13.57 (1H, s) | (CHCl₃) 1740, 1712, 1604, 1583, 1514, 1489, 1462, 1411, 1138, 1056 |
| 18 | 125~126 (methylene chloride-isopropyl ether) | 2.36 (3h, s) 2.72 (3H, s) 3.23 (3H, s) 3.83 (3H, s) 3.89 (3H, s) 3.91 (3H, s) 4.06 (3H, s) 6.77~6.84 (3H, m) 7.25~7.47 (4H, m) 7.74 (1H, s) 12.47 (1H, s) | (CHCl₃) 1739, 1713, 1601, 1583, 1514, 1488, 1462, 1411, 1130, 1057, 1027 |
| 19 | 165~167 (methylene chloride-isopropyl ethyl) | 2.37 (3H, s) 2.76 (3H, s) 3.24 (3H, s) 3.83 (3H, s) 3.89 (3H, s) 3.91 (3H, s) 4.06 (3H, s) 6.78~6.86 (3H, m) 7.20 (2H, d, J = 8.0 Hz) 7.55 (2H, d, J = 8.0 Hz) 7.73 (1H, s) 12.26 (1H, s) | (CHCl₃) 1739, 1713, 1605, 1585, 1514, 1489, 1464, 1411, 1131, 1056 |
| 20 | 183~184 (methylene chloride-isopropyl ether) | 2.70 (3H, s) 3.23 (3H, s) 3.78 (3H, s) 3.80 (3H, s) 3.87 (3H, s) 3.91 (3H, s) 4.06 (3H, s) 6.76 (3H, br. s) 6.84~7.00 (2H, m) 7.27~7.43 (2H, m) 7.78 (1H, s) 13.68 (1H, s) | (CHCl₃) 1738, 1714, 1601, 1582, 1514, 1490, 1463, 1412, 1135, 1058 |

TABLE 8

| Exam. No. | mp (°C.) | ¹H—NMR δ (CDCl₃) ppm | I R ν max (CHCl₃) cm⁻¹ |
|---|---|---|---|
| 21 | 119~121 (isopropyl ether) | 2.77 (3H, s) 3.24 (3H, s) 3.83 (6H, s) 3.89 (3H, s) 3.91 (3H, s) 4.06 (3H, s) 6.77~6.85 (3H, m) 7.00~7.07 (1H, m) 7.16~7.34 (3H, m) 7.74 (1H, s) 12.41 (1H, s) | 1738, 1711, 1598, 1581, 1511, 1487, 1460, 1410, 1130, 1055 |
| 22 | 151~152 (methylene chloride-isopropyl ether) | 2.83 (3H, s) 3.24 (3H, s) 3.83 (6H, s) 3.89 (3H, s) 3.90 (3H, s) 3.91 (3H, s) 4.05 (3H, s) 6.80~6.93 (5H, m) 7.66 (2H, d, J = 6.9 Hz) 7.71 (1H, s) 11.97 (1H, s) | 1738, 1713, 1600, 1510, 1461, 1412, 1168, 1055, 1028 |
| 23 | 165~166 (methylene chloride-isopropyl ether) | 2.79 (3H, s) 3.24 (3H, s) 3.8.3 (3H, s) 3.90 (3H, s) 3.92 (3H, s) 4.06 (3H, s) 6.78~6.86 (3H, m) 7.38 (2H, d, J = 8.8 Hz) 7.58 (2H, d, J = 8.8 Hz) 7.73 (1H, s) 12.30 (1H, s) | 1739, 1712, 1602, 1583, 1512, 1489, 1462, 1411, 1131, 1090, 1056 |
| 24 | 146~148 (methylene chloride-isopropyl ether) | 2.85 (3H, s) 3.24 (3H, s) 3.83 (3H, s) 3.90 (3H, s) 3.91 (6H, s) 3.93 (3H, s) 4.06 (3H, s) 6.78~6.88 (4H, m) 7.24~7.33 (2H, m) 7.72 (1H, s) 11.87 (1H, s) | 1738, 1714, 1597, 1583, 1513, 1463, 1414, 1140, 1059, 1025 |
| 25 | 151~152 (methylene chloride-isopropyl ether) | 2.40 (3H, s) 3.25 (3H, s) 3.82 (3H, s) 3.86 (3H, s) 3.93 (3H, s) 4.07 (3.H, s) 6.74~6.88 (3H, m) 7.46~7.61 (2H, m) 7.77~7.93 (5H, m) 8.04 (1H, br. s) 12.49 (1H, s) | 1738, 1712, 1605, 1584, 1513, 1488, 1461, 1411, 1131, 1054 |

TABLE 9

| Exam. No. | mp (°C.) | ¹H—NMR δ (CDCl₃) ppm | I R ν max (CHCl₃) cm⁻¹ |
|---|---|---|---|
| 26 | 151~153 (methylene chloride- | 2.79 (3H, s), 3.24 (3H, s), 3.83 (3H, s), 3.89 (3H, s) 3.91 (3H, s), 4.06 (3H, s), 6.78~6.85 (3H, m), 7.07 (2H, t, J = 8.6 Hz), 7.63~7.72 (2H, m), 7.73 (1H, s), 12.20 (1H, s) | 1738, 1712, 1600, 1585, 1510, 1488, 1462, 1435, 1410, 1371, 1230, 1155, 1131, 1056, 1028, 848 |
| 27 | 159~161 (methylene chloride-methanol) | 2.84 (3H, s), 3.23 (3H, s), 3.82 (3H, s), 3.89 (3H, s), 3.91 (3H, s), 4.06 (3H, s), 6.76~6.95 (5H, m), 7.37 ~7.50 (1H, m), 7.76 (1H, s), 13.01 (1H, s) | 1736, 1713, 1608, 1585, 1512, 1488, 1463, 1434, 1413, 1235, 1131, 1056, 1027, 970, 853 |
| 28 | 108~110 (methylene chloride-methanol) | 2.69 (3H, s), 3.24 (3H, s), 3.83 (3H, s), 3.89 (3H, s), 3.92 (3H, s), 4.07 (3H, s), 6.76~6.84 (3H, m), 7.62 ~7.73 (4H, m), 7.76 (1H, s), 12.57 (1H, s) | 1737, 1711, 1605, 1580, 1511, 1488, 1461, 1433, 1410, 1373, 1323, 1171, 1135, 1064, 1017 |
| 29 | 125~126 (isopropyl ether) | 0.91 (3H, t, J = 7.2 Hz), 1.53~1.72 (2H, m), 2.60 (2H, t, J = 7.4 Hz), 2.74 (3H, s), 3.23 (3H, s), 3.83 (3H, s) 3.89 (3H, s), 3.91 (3H, s), 4.06 (3H, s), 6.78~6.85 (3H, m), 7.19 (2H, J = 8.0 Hz), 7.56 (2H, d, J = 8.0 Hz), 7.73 (1H, s), 12.30 (1H, s) | 2950, 1739, 1714, 1605, 1584, 1514, 1489, 1464, 1435, 1413, 1373, 1132, 1057 |

TABLE 9-continued

| Exam. No. | mp (°C.) | $^1$H—NMR δ (CDCl$_3$) ppm | I R ν max (CHCl$_3$) cm$^{-1}$ |
|---|---|---|---|
| 30 | 156–157 (isopropyl ether) | 1.30 (9H, s), 2.70 (3H, s), 3.23 (3H, s), 3.83 (3H, s), 3.89 (3H, s), 3.9 (3H, s), 4.06 (3H, s), 6.82 (3H, s) 7.41 (2H, d, J = 8.2 Hz), 7.58 (2H, d, J = 8.2 Hz), 7.74 (1H, s), 12.42 (1H, s) | 2965, 1739, 1714, 1607, 1586, 1515, 1490, 1465, 1436, 1411, 1374, 1133, 1058, 1029 |
| 31 | 213–215 (methylene chloride-methanol) | 3.23 (3H, s), 3.4 (3 (3H, s), 3.87 (3H, s), 3.89 (3H, s) 3.93 (3H, s), 4.04 (3H, s), 6.70–6.88, (3H, m), 7.67 (1H, s), 10.06 (1H, s) | 3565–2345, 1743, 1688 |

Example 31

1-(3,4-Dimethoxyphenyl)-4-hydroxy-2-methoxycarbonyl-3-(pentafluoro-1-oxopropyl)-6,7,8-trimethoxynaphthalene Under nitrogen flow, 1.3 ml (2.0 mmol) of 1.5M MeLi.LiBr in ether was added dropwise to a solution of 260 mg (0.54 mmol) of compound IV-1 (Preparation 7) and 900 mg (3.7 mmol) of pentafluoroethyl iodide in 15 ml of dry methylene chloride at −78° C. After the addition, the mixture was stirred at the same temperature for 15 minutes. Saturated aqueous ammonium chloride was added to the reaction mixture, and the mixture was extracted with methylene chloride. The extract was washed with water and dried over anhydrous magnesium sulfate. After concentration under reduced pressure, the residue was washed with methanol to obtain 240 mg of crude crystals of desired product. Recrystallization from methylene chloride-methanol gave 170 mg (56%) of desired product. The structure of the compound synthesized is shown in above Table 6, and the physical properties thereof are shown in above Table 9.

Preparations 11–15

Compounds (XV) of the formula:

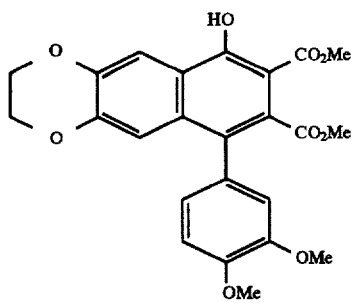
XV-6

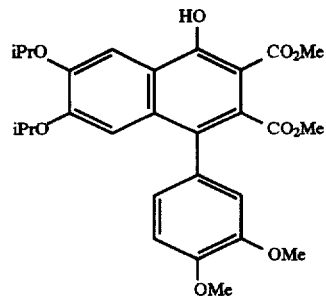
XV-7

-continued

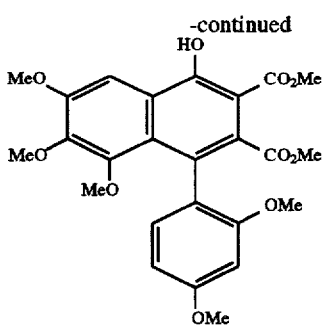
XV-8

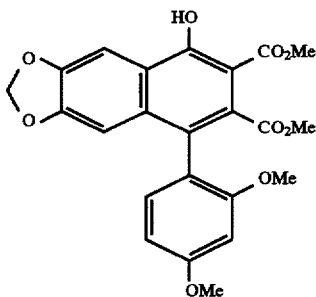
XV-9

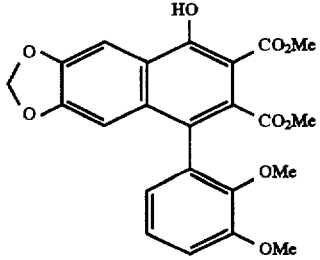
XV-10 were transformed into compounds (IV) of the formulas shown below, respectively:

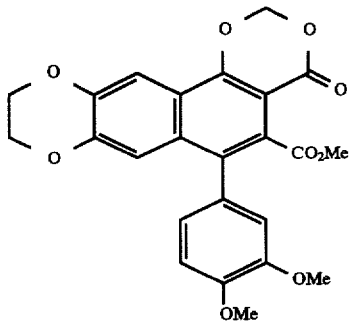
IV-6

-continued

IV-7
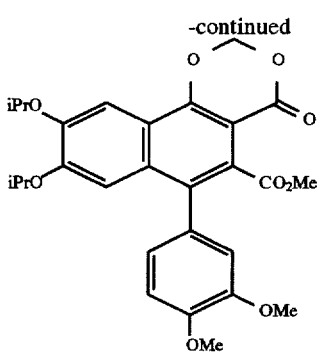

IV-8
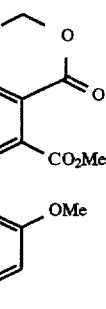

IV-9
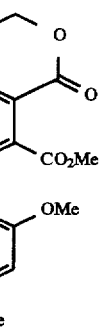

IV-10
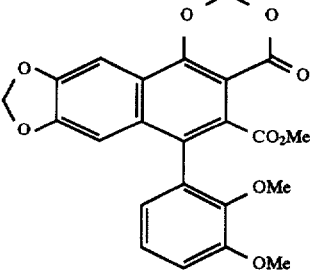

according to the procedure in Preparation 7.

Physical properties of the starting materials of the compounds of the present invention are shown below.

XV-6: mp: 172°–173° C. (methylene chloride-methanol)
$^1$H-NMR: δ(CDCl$_3$) 3.56(3H,s) 3.85(3H,s) 3.92(3H,s) 3.94(3H,s) 4.32(4H,s) 6.80–6.95(4H,m) 7.89(1H,s) 12.31(1H,s) ppm.

XV-7: mp: 120°–121° C. (methylene chloride-methanol)
$^1$H-NMR: δ(CDCl$_3$) 1.25(3H,d,J=2.4 Hz) 1.28(3H,d,J=2.4 Hz) 1.42(6H,d,J=9 Hz) 3.57(3H,s) 3.84(3H,s) 3.93(3H,s) 3.96(3H,s) 4.29–4.41(1H,m) 4.65–4.77(1H,m) 6.79(1H,s) 6.83–6.95(3H,m) 7.80(1H,s) 12.29(1H,s) ppm.

XV-8: mp: 145°–146° C. (methylene chloride-methanol)
$^1$H-NMR: δ(CDCl$_3$) 3.26(3H,s) 3.47(3H,s) 3.67(3H,s) 3.85(3H,s) 3.88(3H,s) 3.96(3H,s) 4.02(3H,s) 6.43–6.48(2H,m) 7.01–7.06(1H,m) 7.65(1H,s) 12.40(1H,s) ppm.

XV-9: mp: 176°–177° C. (methylene chloride-methanol)
$^1$H-NMR: δ(CDCl$_3$) 3.53(3H,s) 3.67(3H,s) 3.87(3H,s) 3.91(3H,s) 6.04(2H,d,J=1.6 Hz) 6.51(2H,m) 6.64(1H,s) 7.04(1H,d,J=9 Hz) 7.74(1H,s) 12.20(1H,s) ppm.

XV-10: mp: 234°–236° C. (methylene chloride-methanol
$^1$H-NMR: δ(CDCl$_3$) 3.56(3H,s) 3.60(3H,s) 3.92(6H,s) 6.03(2H,s) 6.66(1H,s) 6.73–6.77(1H,m) 6.97–7.13(2H,m) 7.74(1H,s) 12.22(1H,s) ppm.

Preparation 11 (IV-6): mp: 288°–289° C.
$^1$H-NMR: δ(CDCl$_3$) 3.67(3H,s) 3.85(3H,s) 3.95(3H,s) 4.35(4H,s) 5.86(2H,s) 6.84–6.95(3H,m) 7.05(1H,s) 7.67(1H,s) ppm.

Preparation 12 (IV-7): mp: 201°–203° C.
$^1$H-NMR: δ(CDCl$_3$) 1.28(3H,d,J=1.8 Hz) 1.28(3H,d,J=1.8 Hz) 1.44(6H,d,J=6.2 Hz) 3.68(3H,s) 3.85(3H,s) 3.96(3H,s) 4.32–4.44(1H,m) 4.64–4.76(1H,m) 5.86(2H,s) 6.87–6.94(4H,m) 7.54(1H,s) ppm.

Preparation 13 (IV-8): mp: 178°–180° C.
$^1$H-NMR: δ(CDCl$_3$) 3.28(3H,s) 3.58(3H,s) 3.67(3H,s) 3.86(3H,s) 3.90(3H,s) 4.02(3H,s) 5.82–5.91(2H,m) 6.45–6.50(2H,m) 7.04–7.09(1H,m) 7.39(1H,s) ppm.

Preparation 14 (IV-9): mp: 225°–227° C.
$^1$H-NMR: δ(CDCl$_3$) 3.64(3H,s) 3.67(3H,s) 3.87(3H,s) 5.82–5.89(2H,m) 6.07–6.09(2H,m) 6.54–6.58(2H,m) 6.76(1H,s) 7.04–7.08(1H,m) 7.49(1H,s) ppm.

Preparation 15 (IV-10): mp: 229°–230° C.
$^1$H-NMR: δ(CDCl$_3$) 3.62(3H,s) 3.66(3H,s) 3.93(3H,s) 5.83–5.91(2H,m) 6.07(2H,s) 6.74–6.78(2H,m) 6.99–7.15(2H,m) 7.50(1H,s) ppm.

Examples 32 to 34

According to Method B in Example 1, the reactions were conducted using compound IV-4 (Preparation 9) to obtain the compounds of Examples listed below.

Example 32:

1-(3,4-Dimethoxyphenyl)-4-hydroxy-2-methoxycarbonyl-6,7-methylenedioxy-3-(1-oxopropyl)naphthalene Example 33:

1-(3,4-Dimethoxyphenyl)-3-(2-ethyl-1-oxobutyl)-4-hydroxy-2-methoxycarbonyl-6,7-(methylenedioxy)naphthalene Example 34:

3-(4-Chlorobenzoyl)-1-(3,4-dimethoxyphenyl)-4-hydroxy-2-methoxycarbonyl-6,7-(methylenedioxy)naphthalene The structures of the compounds listed above are shown in Table 10 hereinafter, and their physical properties are shown in Table 13 hereinafter.

Examples 35 to 37

According to Method B in Example 1, the reactions were conducted using compound IV-6 (Preparation 11) to obtain the compounds of Examples listed below.

Example 35:

1-(3,4-Dimethoxyphenyl)-6,7-ethylenedioxy-4-hydroxy-2-methoxycarbonyl-3-(1-oxopropyl)naphthalene Example 36:

1-(3,4-Dimethoxyphenyl)-6,7-ethylenedioxy-3-(3-ethyl-1-oxopentyl)-4-hydroxy-2-(methoxycarbonyl)naphthalene Example 37:

3-(4-Chlorobenzoyl)-1-(3,4-dimethoxyphenyl)-6,7-ethylenedioxy-4-hydroxy-2-(methoxycarbonyl)naphthalene The structures of the compounds listed above are shown in Table 10 hereinafter, and their physical properties are shown in Table 13 hereinafter.

Examples 38–40

According to Method B in Example 1, the reactions were conducted using compound IV-7 (Preparation 12) to obtain the compounds of Examples listed below.

Example 38:

6,7-Bis(2-propyloxy)-1-(3,4-dimethoxyphenyl)-4-hydroxy-2-methoxycarbonyl-3-(1-oxopropyl)naphthalene Example 39:

6,7-Bis(2-propyloxy)-1-(3,4-dimethoxyphenyl)-3-(3-ethyl-1-oxopentyl)-4-hydroxy-2-(methoxycarbonyl)naphthalene Example 40:

6,7-Bis(2-propyloxy)-1-(3,4-dimethoxyphenyl)-4-hydroxy-2-methoxycarbonyl-3-[4-(trifluoromethyl)benzoyl]naphthalene The structures of the compounds listed above are shown in Table 10 hereinafter, and their physical properties are shown in Table 14 hereinafter.

Examples 41 to 43

According to Method B in Example 1, the reactions were conducted using compound IV-8 (Preparation 13) to obtain the compounds of Examples listed below.

Example 41:

1-(2,4-Dimethoxyphenyl)-4-hydroxy-2-methoxycarbonyl-3-(1-oxopropyl)-6,7,8-trimethoxynaphthalene Example 42:

1-(2,4-Dimethoxyphenyl)-3-(3-ethyl-1-oxopentyl)-4-hydroxy-2-methoxycarbonyl-6,7,8-trimethoxynaphthalene Example 43:

1-(2,4-Dimethoxyphenyl)-4-hydroxy-2-methoxycarbonyl-3-[4-(trifluoromethyl)benzoyl]-6,7,8-trimethoxynaphthalene The structures of the compounds listed above are shown in Table 11 hereinafter, and their physical properties are shown in Table 15 hereinafter.

Examples 44 to 46

According to Method B in Example 1, the reactions were conducted using compound IV-9 (Preparation 14) to obtain the compounds of Examples listed below.

Example 44:

1-(2,4-Dimethoxyphenyl)-4-hydroxy-2-methoxycarbonyl-6,7-methylenedioxy-3-(1-oxopropyl)naphthalene Example 45:

1-(2,4-Dimethoxyphenyl)-3-(3-ethyl-1-oxopentyl)-4-hydroxy-2-methoxycarbonyl-6,7-(methylenedioxy)naphthalene Example 46:

1-(2,4-Dimethoxyphenyl)-4-hydroxy-2-methoxycarbonyl-6,7-methylenedioxy-3-[4-(trifluoromethyl)benzoyl]naphthalene The structures of the compounds listed above are shown in Table 12 hereinafter, and their physical properties are shown in Table 16 hereinafter.

Examples 47 to 49

According to Method B in Example 1, the reactions were conducted using compound IV-10 (Preparation 15) to obtain the compounds of Examples listed below.

Example 47:

1-(2,3-Dimethoxyphenyl)-4-hydroxy-2-methoxycarbonyl-6,7-methylenedioxy-3-(1-oxopropyl)naphthalene Example 48:

1-(2,3-Dimethoxyphenyl)-3-(3-ethyl-1-oxopentyl)-4-hydroxy-2-methoxycarbonyl-6,7-(methylenedioxy)naphthalene Example 49:

1-(2,3-Dimethoxyphenyl)-4-hydroxy-2-methoxycarbonyl-6,7-methylenedioxy-3-[4-(trifluoromethyl)benzoyl]naphthalene The structures of the compounds listed above are shown in Table 12 hereinafter, and their physical properties are shown in Table 17 hereinafter.

The procedure to prepare the compounds of the present invention by Method C is described below. First, the starting materials shown below were prepared.

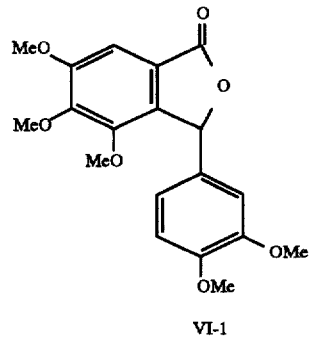

VI-1

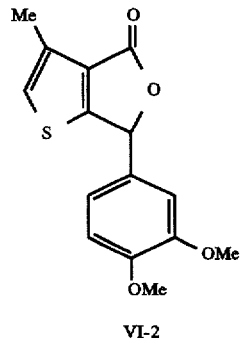

VI-2

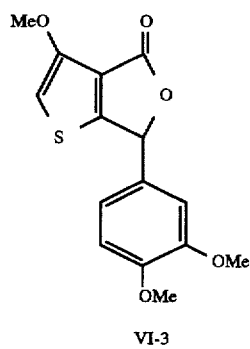
VI-3
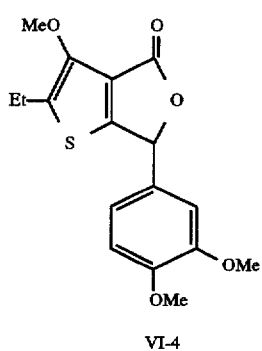
VI-4
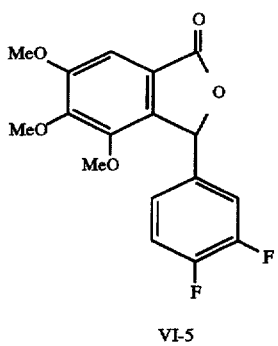
VI-5
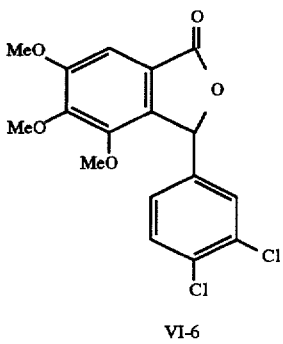
VI-6
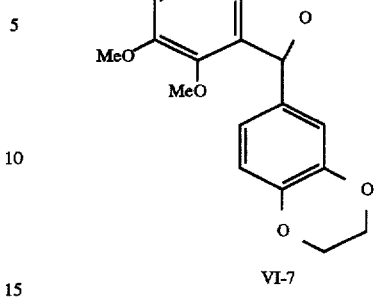
VI-7
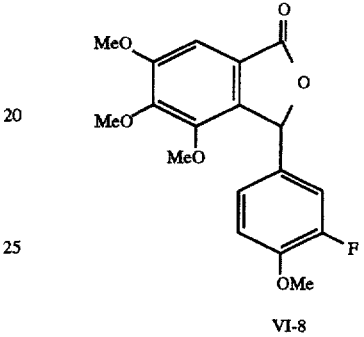
VI-8
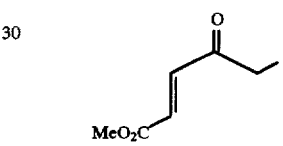
VII-1
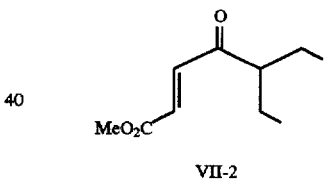
VII-2
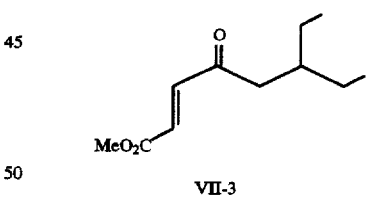
VII-3
[VII]
Preparation 16
Synthesis of 3-(3,4-dimethoxyphenyl)-4,5,6-trimethoxy-1(3H)-isobenzofuranone: VI-1
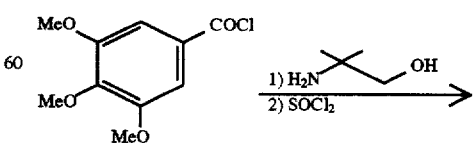
17

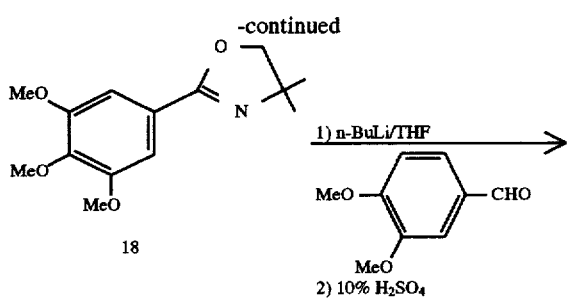

Step-1 (4,4-Dimethyl-2-(3,4,5-trimethoxyphenyl)-2-oxazoline: 18)

A solution of 16.2 g (70 mmol) of 3,4,5-trimethoxybenzoyl chloride (17) in 40 ml of dry methylene chloride was added dropwise to a solution of 12.5 g (140 mmol) of 2-amino-2-methyl-1-propanol in 50 ml of dry methylene chloride under cooling in an ice-bath over 30 minutes. After additional stirring for 45 minutes, the reaction mixture was filtered through a glass filter. The filter cake was washed with methylene chloride. The filtrate and the washing were combined and concentrated under reduced pressure. The residue was dissolved in 30 ml of toluene, and then 6.64 ml (91.0 mmol) of thionyl chloride was added dropwise under cooling in an ice-bath. The mixture was allowed to warm to room temperature while being stirred for 45 minutes. To the reaction mixture was added ice (20 g) and aqueous sodium hydroxide (18 g of NaOH in 60 ml of water) and the mixture was extracted with toluene. The extract was washed with water and brine, and dried over anhydrous magnesium sulfate. After concentration under reduced pressure, the residue was crystallized from 70 ml of n-hexane to obtain 16.8 g (90.6%) of desired compound 18.

mp: 87°–89° C.

$^1$H-NMR: δ(CDCl$_3$) 1.39(6H,s) 3.88(3H,s) 3.91(6H,s) 4.10(2H,s) 7.20(2H,s) ppm.

Step-2 (Synthesis of VI-1)

To a solution of compound 18 (16.8 g, 63.4 mmol) in 100 ml of dry THF, which was cooled with refrigerant at –30° C. 40.0 ml of 1.68N n-BuLi in n-hexane was added dropwise over 15 minutes under nitrogen flow. After stirring for 45 minutes, the mixture was cooled to –78° C., and a solution of 11.6 g (69.7 mmol) of 3,4-dimethoxybenzaldehyde in 30 ml of dry THF was added dropwise thereto. The mixture was allowed to warm to room temperature while being stirred for 1 hour. After addition of 20 ml of saturated aqueous ammonium chloride and 20 ml of water, the mixture was extracted with ethylacetate. The extract was washed with water and brine, and dried over anhydrous magnesium sulfate. After concentration under reduced pressure, the residue was dissolved in 70 ml of 10% sulfuric acid, and heated under reflux for 30 minutes. To the reaction mixture was added ice and water, and the mixture was extracted with methylene chloride. The extract was dried over anhydrous magnesium sulfate. After concentration under reduced pressure, the residue was crystallized from 80 ml of methanol to obtain 20.6 g (90.4%) of desired compound (VI-1).

mp: 141°–142° C.

$^1$H-NMR: δ(CDCl$_3$) 3.52(3H,s) 3.83(3H,s) 3.89(3H,s) 3.92(3H,s) 3.95(3H,s) 6.32(1H,s) 6.72(1H,s) 6.86(2H,s) 7.21(1H,s) ppm.

Preparations 17–20

The reactions were conducted similarly to that of Preparation 16 to obtain compounds VI-5, 6, 7 and 8, whose yields and physical properties are shown below.

Preparation 17 (VI-5); Yield: 80% (through 2 steps)

mp: 107°–108° C. (ether)

$^1$H-NMR: δ(CDCl$_3$) 3.60(3H,s) 3.92(3H,s) 3.95(3H,s) 6.29(1H,s) 7.02–7.18(3H,m) 7.20(1H,s) ppm.

Preparation 18 (VI-6); Yield: 79% (through 2 steps)

mp: 125°–127° C. (ether)

$^1$H-NMR: δ(CDCl$_3$) 3.62(3H,s) 3.91(3H,s) 3.95(3H,s) 6.28(1H,s) 7.15(1H,dd,J=8.4 Hz,2.2 Hz) 7.20(1H,s) 7.39 (1H,d,J=2.2 Hz) 7.45(1H,d,J=8.4 Hz) ppm.

Preparation 19 (VI-7); Yield: 88% (through 2 steps)

mp: 119°–121° C. (ether)

$^1$H-NMR: δ(CDCl$_3$) 3.56(3H,s) 3.92(3H,s) 3.94(3H,s) 4.24(4H,s) 6.25(1H,s) 6.72–6.88(3H,m) 7.19(1H,s) ppm.

Preparation 20 (VI-8); Yield: 82% (through 2 steps)

mp: 121°–122.5° C. (ether)

$^1$H-NMR: δ(CDCl$_3$) 3.56(3H,s) 3.89(3H,s) 3.92(3H,s) 3.95(3H,s) 6.28(1H,s) 6.89–7.09(3H,m) 7.20(1H,s) ppm.

Preparation 21

Synthesis of 4,6-dihydro-6-(3,4-dimethoxyphenyl)-3-methyl-4-oxothieno[2,3-c]furan: VI-2

Step-1 (4-Methylthiophen-3-carboxylic acid: 19)

A mixture of 8.30 g (67.4 mmol) of 3-cyano-4-methylthiophene [J. W. Terpstra and A. M. von Leusen, J. Org. Chem., 51, 230 (1986)] and 83 ml of concentrated hydrochloric acid was heated under reflux for 40 hours. After cooling, the mixture was extracted with ethyl acetate. The extract was washed with water and brine, and then dried over anhydrous magnesium sulfate. The solvent was distilled off under reduced pressure and the residue was washed with petroleum ether to obtain 6.40 g of desired compound 19. The solvent in the washings was distilled off, and to the residue was added 5 ml of water, 5 ml of acetic acid and 5 ml of conc. sulfuric acid, and then the mixture was stirred for 3.5 hours at 135° C. After cooling, the mixture was extracted with ether. The ether layer was extracted with 10% aqueous sodium hydroxide. The aqueous layer was acidified with dilute hydrochloric acid, and extracted again with ether. The extract was washed with water and brine, and dried over anhydrous magnesium sulfate. The solvent was distilled off under reduced pressure and the residue was washed with petroleum ether to obtain 1.57 g of desired compound 19 (total yield: 83%).

mp: 137°–138° C.

$^1$H-NMR: δ(CDCl$_3$) 2.49(3H,d,J=0.8 Hz) 6.94–6.98(1H, m) 8.24(1H,d,J=3.6 Hz) ppm.

Step-2 (VI-2)

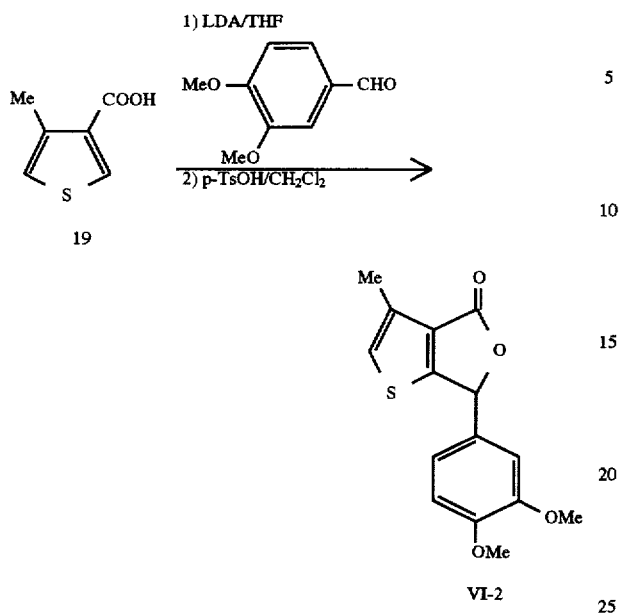

To a solution of 11.6 g (114 mmol) of diisopropylamine in 150 ml of dry THF cooled at −78° C., 68.9 ml of 1.66M n-BuLi in n-hexane (114 mmol) was added dropwise under nitrogen flow. After addition, the mixture was stirred at 0° C. for additional 30 minutes, and then re-cooled to −78° C. To this cooled solution, a solution of 4-methyl-3-thiophenecarboxylic acid 19 obtained above (7.40 g, 52.0 mmol) in 50 ml of dry THF was added dropwise, and the mixture was stirred at 0° C. for 30 minutes, and then cooled again to −78° C. To the cooled solution, a solution of 8.65 g (52.1 mmol) of 3,4-dimethoxybenzaldehyde in 50 ml of dry THF was added dropwise over 10 minutes. After addition, the mixture was stirred for 100 minutes at the same temperature. The reaction mixture was acidified by addition of ice and 6N HCl, and then extracted with ethyl acetate. The extract was washed with water and brine, and dried over anhydrous magnesium sulfate. The solvent was distilled off under reduced pressure. The residue was dissolved in 50 ml of dry methylene chloride and to the solution was added 740 mg (3.87 mmol) of p-toluenesulfonic acid monohydride. The mixture was stirred at room temperature for 1 hour. After washing with saturated aqueous sodium bicarbonate and water, the mixture was dried over anhydrous magnesium sulfate. The residue obtained by concentration under reduced pressure was washed with petroleum ether to obtain 13.5 g (89%) of desired lactone VI-2.

mp: 155.5°–158° C.

$^1$H-NMR: δ(CDCl$_3$) 2.44(3H,d,J=1.2 Hz) 3.85(3H,s) 3.89 (3H,s) 6.43(1H,s) 6.77–7.04(4H,m) ppm.

Preparations 22–23

Syntheses of VI-3, 4

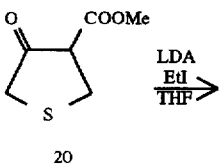

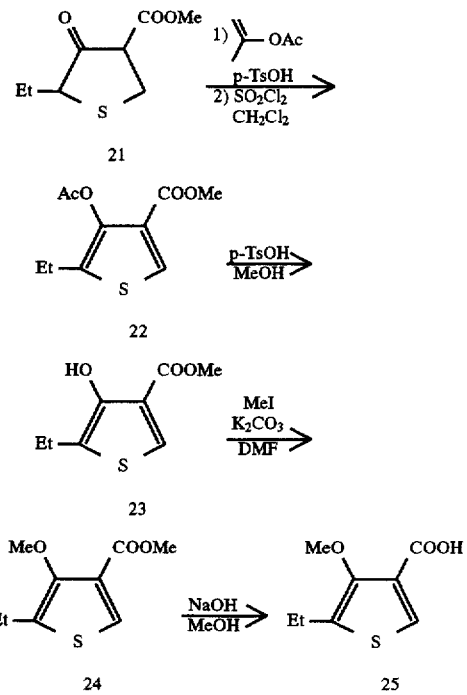

Step-1 (Methyl tetrahydro-5-ethyl-4-oxothiophen-3-carboxylate: 21)

To a solution of 33.4 g (330 mmol) of diisopropylamine in 300 ml of dry THF cooled at −78° C., 199 ml of 1.66M n-BuLi in n-hexane (330 mmol) was added dropwise under nitorogen flow. After completion of the addition, the mixture was stirred at 0° C. for additional 30 minutes, and then re-cooled to −78° C. To this cooled reaction mixture, a solution of 24.0 g (150 mmol) of methyl tetrahydro-4-oxothiophen-3-carboxylate 20 [O. Hromatka, D. Binder and K. Eichinger, Monatsh. Chem., 104, 1520 (1973)] in 30 ml of dry THF was added dropwise, and then the mixture was stirred at −30° C. for 30 minutes. To this mixture, 23.4 g (150 mmol) of ethyl iodide was added dropwise at the same temperature over 10 minutes. After addition, the mixture was stirred for additional 2 hours at −20° C. The reaction mixture was acidified by addition of ice and 6N hydrochloric acid, and extracted with ethyl acetate. The extract was washed with water and brine, and dried over anhydrous magnesium sulfate. After concentration under reduced pressure, the residue was purified by column chromatography on silica gel (ethyl acetate:n-hexane=4:1) to obtain 13.6 g (48%) of desired compound 21 as an oil.

$^1$H-NMR: δ(CDCl$_3$) 1.00(3H,t,J=7.3 Hz) 1.63–2.12(2H, m) 3.66–3.70(2H,m) 3.77(3H,s) 4.12–4.22(1H,m) 10.98 (1H,s) ppm.

Step-2 (Methyl 4-acetoxy-5-ethylthiophen-3-carboxylate: 22)

A mixture of compound 21 obtained above (13.6 g, 72.2 mmol), 41 ml of isopropenyl acetate and 50 mg of p-toluenesulfonic acid monohydrate was heated under reflux for 22 hours. Excess isopropenyl acetate and generated acetone were distilled off under reduced pressure, and then the residue was purified by column chromatography on silica gel (ethyl acetate:n-hexane=4:1) to obtain 17.2 g of an oil. The oil was dissolved in 150 ml of dry methylene chloride, and to the solution 11.7 g (86.6 mmol) of sulfuryl chloride was added at −20° C. over 30 minutes. The mixture was stirred for 1 hour at the same temperature, and then allowed to stand at room temperature overnight. The reaction mixture was washed with saturated aqueous sodium bicarbonate and water, dried over anhydrous magnesium sulfate, and evaporated under reduced pressure to obtain 14.7 g (88%) of desired compound 22 as an oil.

$^1$H-NMR: δ(CDCl$_3$) 1.24(3H,t,J=7.5 Hz) 2.35(3H.s) 2.69 (2H,q,J=7.5 Hz) 3.81(3H,s) 7.89(1H,s) ppm.

Step-3 (Methyl 5-ethyl-4-hydroxythiophen-3-carboxylate: 23)

To a solution of compound 22 obtained above (14.8 g, 64.9 mmol) in 41 ml of dry methanol was added 250 mg of p-toluenesulfonic acid monohydrate, and the mixture was heated under reflux for 22 hours. After methanol was distilled off under reduced pressure, saturated aqueous sodium bicarbonate was added thereto. The mixture was extracted with ethyl acetate. The extract was washed with water, dried over anhydrous magnesium sulfate, and evaporated under reduced pressure to obtain 10.4 g (86%) of desired compound 23 as an oil.

$^1$H-NMR: δ(CDCl$_3$) 1.25(3H,t,J=7.5 Hz) 2.74(2H,q,J=7.5 Hz) 3.90(3H,s) 7.71(1H,s) 8.52(1H,s) ppm Step-4 (Methyl 5-ethyl-4-methoxythiophen-3-carboxylate: 24)

To a solution of compound 23 obtained above (10.1 g, 50 mmol) in 100 ml of dry DMF was added 9.71 g (70.3 mmol) of potassium carbonate and 9.97 g (70.2 mmol) of methyl iodide, and the mixture was stirred at 70° C. for 2 hours. After cooling, the mixture was poured into dilute hydrochloric acid and ice, and extracted with ethyl acetate. The extract was washed with water and dried over anhydrous magnesium sulfate. The solvent was distilled off under reduced pressure, and the residue was distilled under reduced pressure to obtain 6.36 g (59%) of desired compound 24 as an oil.

bp: 86°–93° C. (3 mmHg)

$^1$H-NMR: δ(CDCl$_3$) 1.26(3H,t,J=7.6 Hz) 2.78(2H,q,J=7.6 Hz) 3.83(3H,s) 3.86(3H,s) 7.81(1H,s) ppm Step-5 (5-Ethyl-4-methoxythiophen-3-carboxylic acid: 25)

To a solution of compound 24 obtained above (6.36 g, 31.8 mmol) in 50 ml of methanol was added 20 ml of 10% aqueous sodium hydroxide, and the mixture was heated under reflux for 35 minutes. After cooling, dilute hydrochloric acid and ice was added, and the resulting mixture was extracted with ethyl acetate. The extract was washed with water and dried over anhydrous magnesium sulfate. The solvent was distilled off under reduced pressure, and the residue was purified by column chromatography on silica gel (methylene chloride:methanol=19:1) to obtain 4.74 g (80%) of desired compound 25.

mp: 109°–112° C.

$^1$H-NMR: δ(CDCl$_3$) 1.29(3H,t,J=7.5 Hz) 2.72(2H,q,J=7.5 Hz) 3.89(3H,s) 7.99(1H,s) ppm Step-6

The reaction was conducted similarly to that of Step-2 in Preparation 21 to obtain VI-3 and VI-4 from 4-methoxy-3-thiophenecarboxylic acid [J. B. Press, C. M. Hofmann and S. R. Safir, J. Org. Chem., 44, 3292 (1979)] and 5-ethyl-4-methoxythiophen-3-carboxylic acid 25, respectively. Yields and physical properties are shown below.

Preparation 22 (VI-3); Yield: 45% (through 2 steps)

mp: 158.5°–160.5° C. (ether)

$^1$H-NMR: δ(CDCl$_3$) 2.85(3H,s) 3.89(3H,s) 3.94(3H,s) 6.34(2H,s) 6.76–6.96(3H,m) ppm.

Preparation 23 (VI-4); Yield: 86% (through 2 steps)

$^1$H-NMR: δ(CDCl$_3$) 1.24(3H,t,J=7.5 Hz) 2.68–2.83(2H, m) 3.86(3H,s) 3.89 (3H,s) 4.13(3H,s) 6.30(1H,s) 6.78–6.94 (3H,m) ppm.

Preparations of compound (VII) are shown below.

Preparation 24

Synthesis of methyl(E)-5-ethyl-4-oxo-2-heptenoate: VII-2

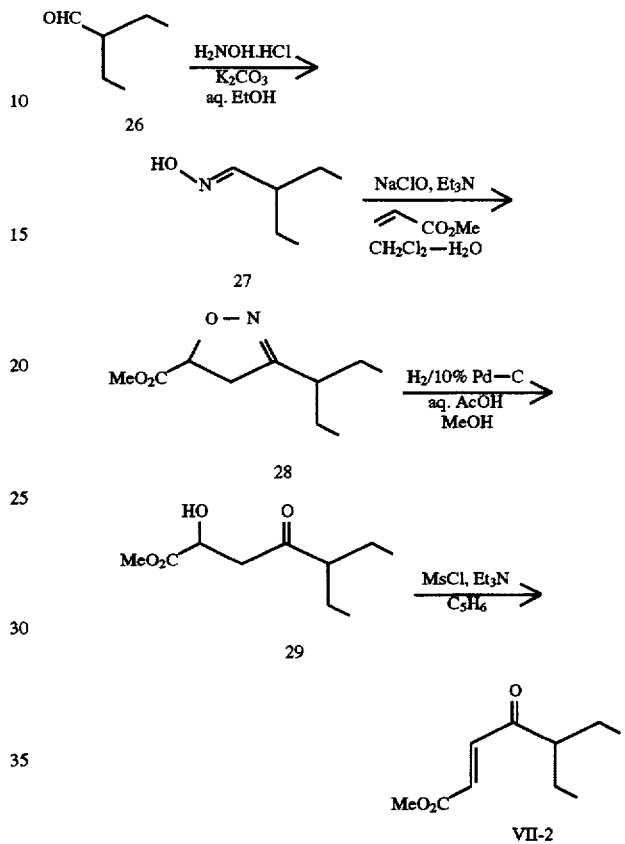

Step-1 ((2-Ethylbutyliden)azanol: 27)

A solution of 40.0 g (400 mmol) of (2-ethyl) butyraldehyde in 250 ml of 99% ethanol was added dropwise to a solution of 30.6 g (440 mmol) of hydroxylamine hydrochloride and 33.1 g (240 mmol) of potassium carbonate under cooling in an ice-bath. After the addition, the mixture was allowed to warm to room temperature while being stirred for 1.5 hours, and then the resulting mixture was diluted with 500 ml of ice water and extracted with ether. The extract was washed with water and brine, dried over anhydrous magnesium sulfate, and concentrated under reduced pressure to obtain 48.1 g of desired compound 27 as a crude oily product, which was used in the next reaction without purification.

Step-2 (3-(1-Ethyl)propyl-5-(methoxycarbonyl)-2-isooxazoline: 28)

To a mixture of 400 ml of about 10% aqueous sodium hypochlorite (about 600 mmol) and a solution of 40.0 ml (440 mmol) of methyl acrylate and 5.57 ml (40 mmol) of triethylamine in 150 ml of methylen chloride, a solution of 48.1 g of crude oxime 27 obtained above in 150 ml of methylene chloride was added dropwise with vigorous stirring under cooling in an ice-bath. After the addition, the mixture was allowed to warm to room temperature with stirring for 2 hours. Ice and water were added, and then the mixture was extracted with methylene chloride. The extract was dried over anhydrous magnesium sulfate and concentrated under reduced pressure. The residue was distilled under reduced pressure to obtain 60.2 g (75.7%, through 2 steps) of desired compound 28 as an oil.

bp: 95°–97° C. (1 mmHg)

$^1$H-NMR: δ(CDCl$_3$) 0.88(3H,t,J=7.4 Hz) 0.89(3H,t,J=7.4 Hz) 1.33–1.71(4H,m) 2.36–2.53(1H,m) 3.13(1H,d,J=9.6 Hz) 3.14(1H,d,J=7.8 Hz) 3.79(3H,s) 4.99(1H,dd,J=9.6 Hz,7.8 Hz) ppm.

Step-3 (Methyl 5-ethyl-2-hydroxy-4-oxoheptanoate: 29)

Isooxazoline 28 obtained above (45.4 g, 228 mmol) was dissolved in a solvent mixture of 200 ml of methanol, 40 ml of water and 40 ml of acetic acid, and the mixture was stirred at room temperture for 5 hours in the presence of 1.36 g of 10% Pd—C under hydrogen atomosphere. After filtering off Pd—C, the mixture was diluted with 200 ml of water, and extracted with ether. The extract was washed with water, saturated aqueous sodium bicarbonate, and brine, dried over anhydrous magnesium sulfate, and concentrated under reduced pressure to obtain 42.3 g of desired compound 29 as a crude oily product, which was subjected to the next reaction without purification.

Step-4 (VII-2)

To a solution of 42.3 g of crude hydroxyketone 29 obtained above and 139 ml (838 mmol) of triethylamine in 200 ml of dry benzene was added 24.3 ml of methanesulfonyl chloride under cooling in an ice-bath, and the mixture was allowed to warm to room temperature while being stirred overnight. The reaction mixture was diluted with 300 ml of water and extracted with ethyl acetate. The extract was washed with water, 2N HCl, water and brine, successively. The mixture was dried over anhydrous magnesium sulfate and concentrated under reduced pressure. The residue was distilled under reduced pressure to obtain 32.1 g (76.5%, through 2 steps) of desired compound VII-2 as an oil.

bp: 64°–67° C. (0.5 mmHg)

$^1$H-NMR: δ(CDCl$_3$) 0.86(6H,t,J=7.4 Hz) 1.42–1.80(4H, m) 2.51–2.70(1H,m) 3.82(3H,s) 6.72(1H,d,J=15.8 Hz) 7.19 (1H,d,J=15.8 Hz) ppm.

Preparations 25–26

VII-1 and VII-3

The reactions were conducted similarly to that of Preparation 24 to obtain compound VII-1 and 3. The physical properties are shown below.

Preparation 25 (VII-1); bp: 87°–90° C. (8 mmHg)

$^1$H-NMR: δ(CDCl$_3$) 1.14(3H,t,J=7.2 Hz) 2.67(2H,q,J=7.2 Hz) 3.81(3H,s) 6.69(1H,d,J=16.0 Hz) 7.09(1H,d,$^J$=16.0 Hz) ppm.

Preparation 26 (VII-3); bp: 75°–76° C. (0.8 mmHg)

$^1$H-NMR: δ(CDCl$_3$) 0.86(6H,t,J=7.2 Hz) 1.19–1.50(4H, m) 1.79–1.96(1H,m)2.54(2H,d,J=6.6 Hz) 3.82(3H,s) 6.67 (1H,d,J=15.8 Hz) 7.09(1H,d,J=15.8 Hz) ppm.

Example 50

Synthesis of compound I-1 of Example 1 by Method C

Step-1 (1,2-Dihydro-1,4-dihydroxy-1-(3,4-dimethoxyphenyl)-3-(3-ethyl-1-oxopentyl)-2-(methoxycarbonyl)-6,7,8-trimethoxynaphthalene; VIII-1)

Under nitrogen flow, 30 ml of 1.68M n-BuLi in n-hexane (50.4 mmol) was added dropwise to a solution of 10.6 ml (50.4 mmol) of (TMS)$_2$NH in 35 ml of dry THF under cooling in an ice-bath. After addition, the mixture was stirred at the same temperature for 20 minutes and then cooled to −78° C. To the cooled solution, a solution of lactone VI-1 obtained in Preparation 16 (9.00 g, 25.0 mmol) in 25 ml of dry methylene chloride was added dropwise over 20 minutes. After stirring for 25 minutes, a solution of unsaturated ketoester VII-3 obtained in Preparation 26 (5.45 g, 27.5 mmol) in 20 ml of dry THF was added dropwise over 20 minutes. After the addition, 8.8 ml (27.5 mmol) of HMPA was added thereto and the mixture was warmed to 0° C. The reaction mixture was stirred under cooling in an ice-bath for 2.5 hours. Ice and 50 ml of 2N HCl were added to the reaction mixture, and the resulting mixture was extracted with ethyl acetate. The extract was washed with water and brine, and dried over anhydrous magnesium sulfate. After concentration under reduced pressure, the residue was crystallized from 35 ml of methanol, and then recrystallized twice from 30 ml of methanol to obtain 8.93 g (63.9%) of desired compound VIII-1.

mp: 132°–133° C.

$^1$H-NMR: δ(CDCl$_3$) 0.65(3H,t,J=7.2 Hz) 0.69(3H,t,J=7.2 Hz) 0.80–1.29(5H,m) 2.03(1H,dd,J=14.0 Hz,7.0 Hz) 2.31 (1H,dd,J=14.0 Hz,6.4 Hz) 3.40(3H,s) 3.67(3H,s) 3.81(3H,s) 3.86(3H,s) 3.88(1H,s) 3.94(3H,s) 3.99(3H,s) 5.73(1H,s) 6.43(1H,dd,J=8.4 Hz,2.2 Hz) 6.64(1H,d,J=8.4 Hz) 7.14(1H, d,J=2.2 Hz) 7.54(1H,s) ppm.

Step-2 (I-1)

Under nitrogen atmosphere, a solution of BF$_3$.OEt$_2$ (2.56 ml, 208 mmol) in 7 ml of dry methylene chloride was added dropwise under cooling in an ice-bath to a solution of compound VIII-1 obtained above (8.93 g, 160 mmol) in 40 ml of dry methylene chloride over 10 minutes, and the mixture was stirred at the same temperature for 17 minutes. To the reaction mixture was added 4.0 ml (28.8 mmol) of triethylamine, and the resulting mixture was stirred at room temperature for 10 minutes. Water was added to the reaction mixture, which was then extracted with methylene chloride. The extract was washed with 1N hydrochloric acid, water and brine, and dried over anhydrous magnesium sulfate. The mixture was concentrated under reduced pressure and the residue was crystallized from 30 ml of methanol. Further recrystallization from 30 ml of methanol gave 8.32 g (96.3%) of desired compound I-1.

mp: 127.5°–128.5° C.

Example 51

Synthesis of compound I-4 of Example 4 by Method C

Step-1 (1,2-Dihydro-1,4-dihydroxy-1-(3,4-dimethoxyphenyl)-3-(2-ethyl-1-oxobutyl)-2-(methoxycarbonyl)-6,7,8-trimethoxynaphthalene: VIII-4)

Under nitrogen flow, 59.6 ml of 1.68M n-BuLi in n-hexane (50.0 mmol, 2.0 eq) was added dropwise to a solution of 21.2 ml of (TMS)$_2$NH (50.0 mmol, 2.0 eq) in 10 ml of dry THF under cooling in an ice-bath. After the addition, the mixture was stirred at the same temperature for 20 minutes and then cooled to −78° C. To the cooled solution, a solution of lactone VI-1 obtained in Preparation 16 (18.0 g, 50.0 mmol) in 80 ml of dry DMF was added dropwise over 30 minutes. After stirring for 20 minutes, a solution of unsaturated ketoester VII-2 obtained in Preparation 24 (11.0 g, 60.0 mmol) in 40 ml of dry THF was added dropwise thereto over 12 minutes. After stirring at the same temperature for 25 minutes, the mixture was warmed to 0° C. over 35 minutes. The reaction mixture was stirred under cooling in an ice-bath for 3.5 hours. Ice and 100 ml of 2N HCl was added to the reaction mixture, and the resulting mixture was extracted with ethyl acetate. The extract was washed with water and brine, and dried over anhydrous magnesium sulfate. After concentration under reduced pressure, the residue was crystallized from 100 ml of methanol, and then recrystallized from 100 ml of methanol to obtain 15.1 g (55.4%) of desired compound VIII-4.

mp: 156°–157° C.

$^1$H-NMR: δ(CDCl$_3$) 0.19(3H,t,J=7.4 Hz) 0.75(3H,t,J=7.4 Hz) 1.13–1.72(4H,m) 2.35–2.51(1H,m) 3.42(3H,s) 3.65 (3H,s) 3.79(3H,s) 3.86(3H,s) 3.94(3H,s) 3.96(1H,s) 3.99 (3H,s) 5.76(1H,s) 6.42(1H,dd,J=8.4 Hz,2.2 Hz) 6.64(1H,d, J=8.4 Hz) 7.14(1H,d,J=2.2 Hz) 7.56(1H,s) ppm.

Step-2 (Compound I-4)

Under nitrogen atmosphere, a solution of 4.43 ml of BF$_3$.OEt$_2$ (36.0 mmol, 1.3 eq) in 20 ml of dry methylene chloride was added dropwise under cooling in an ice-bath to a solution of compound VIII-4 obtained above (15.1 g, 27.7 mmol) in 150 ml of dry methylene chloride over 7 minutes, and the mixture was stirred at the same temperature for 10 minutes. To the reaction mixture was added 9.64 ml (69.3 mmol, 2.5 eq) of triethylamine, and the resulting mixture was stirred at room temperature for 5 minutes. Water was added to the reaction mixture, which was then extracted with ethyl acetate. The extract was washed with 1N hydrochloric acid, water and brine, and dried over anhydrous magnesium sulfate. The mixture was concentrated under reduced pressure and the residue was crystallized from 60 ml of 90% aqueous ethanol, and then recrystallized from 50 ml of 80% aqueous ethanol to obtain 11.3 g (77.3%) of desired compound I-4.

mp: 113°–114° C.

$^1$H-NMR: δ(CDCl$_3$) 0.82(3H,t,J=8 Hz) 0.83(3H,t,J=8 Hz) 1.42–1.60(2H,m) 1.64–1.81(2H,m) 2.78–2.90(1H,m) 3.24 (3H,s) 3.42(3H,s) 3.86(3H,s) 3.89(3H,s) 3.93(3H,s) 4.03 (3H,s) 6.81–6.87(3H,m) 7.72(1H,s) 14.18(1H,s) ppm.

Examples 52 to 61

According to Method C in Example 50, the compounds of Examples listed below were synthesized.

Example 52

7-(3,4-Dimethoxyphenyl)-4-hydroxy-6-methoxycarbonyl-3-methyl-5-(1-oxopropyl)benzo[b]thiophene Using compound VI-2 (Preparation 21) and compound VII-1 (Preparation 25), the title compound was obtained.

Example 53

7-(3,4-Dimethoxyphenyl)-5-(3-ethyl-1-oxopentyl)-4-hydroxy-6-methoxycarbonyl-3-methylbenzo[b]thiophene Using compound VI-2 (Preparation 21) and compound VII-3 (Preparation 26), the title compound was obtained.

The structures and the physical properties of the compound listed above are shown in Table 10 and Table 18 hereinafter, respectively.

Example 54

7-(3,4-Dimethoxyphenyl)-4-hydroxy-3-methoxy-6-methoxycarbonyl-5-(1-oxopropyl)benzo[b]thiophene Using compound VI-3 (Preparation 22) and compound VII-1 (Preparation 25), the title compound was obtained.

Example 55

7-(3,4-Dimethoxyphenyl)-5-(3-ethyl-1-oxopentyl)-4-hydroxy-3-methoxy-6-(methoxycarbonyl)benzo[b]thiophene Using compound VI-3 (Preparation 22) and compound VII-3 (Preparation 26), the title compound was obtained.

Example 56

7-(3,4-Dimethoxyphenyl)-2-ethyl-4-hydroxy-3-methoxy-6-methoxycarbonyl-5-(1-oxopropyl)benzo[b]thiophene Using compound VI-4 (Preparation 23) and compound VII-1 (Preparation 25), the title compound was obtained.

Example 57

7-(3,4-Dimethoxyphenyl)-2-ethyl-5-(3-ethyl-1-oxopentyl)-4-hydroxy-3-methoxy-6-(methoxycarbonyl)benzo[b]thiophene Using compound VI-4 (Preparation 23) and compound VII-3 (Preparation 26), the title compound was obtained.

The structures and the physical properties of the compounds listed above are shown in Table 10 and Table 19 hereinafter, respectively.

Example 58

1-(3,4-Difluorophenyl)-3-(3-ethyl-1-oxopentyl)-4-hydroxy-2-methoxycarbonyl-6,7,8-trimethoxynaphthalene Using compound VI-5 (Preparation 17) and compound VII-3 (Preparation 26), the title compound was obtained.

Example 59

1-(3,4-Dichlorophenyl)-3-(3-ethyl-1-oxopentyl)-4-hydroxy-2-methoxycarbonyl-6,7,8-trimethoxynaphthalene Using compound VI-6 (Preparation 18) and compound VII-3 (Preparation 26), the title compound was obtained.

Example 60

1-[3,4-(Ethylenedioxy)phenyl]-3-(3-ethyl-1-oxopentyl)-4-hydroxy-2-methoxycarbonyl-6,7,8-trimethoxynaphthalene Using compound VI-7 (Preparation 19) and compound VII-3 (Preparation 26), the title compound was obtained.

Example 61

3-(3-Ethyl-1-oxopentyl)-1-(3-fluoro-4-methoxyphenyl)-4-hydroxy-2-methoxycarbonyl-6,7,8-trimethoxynaphthalene Using compound VI-8 (Preparation 20) and compound VII-3 (Preparation 26), the title compound was obtained.

The structures and the physical properties of the compounds listed above are shown in Table 11 and Table 20 hereinafter, respectively.

Alternative methods to prepare the compounds of the present invention are described below.

Preparation 27

Synthesis of 3-bromo-1-(3,4-dimethoxyphenyl)-4-methoxymethoxy-2-methyl-6,7,8-trimethoxynaphthalene: 36a

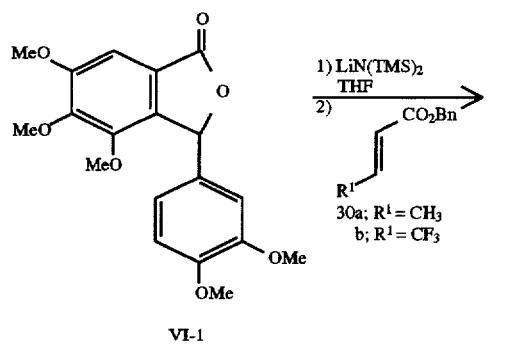

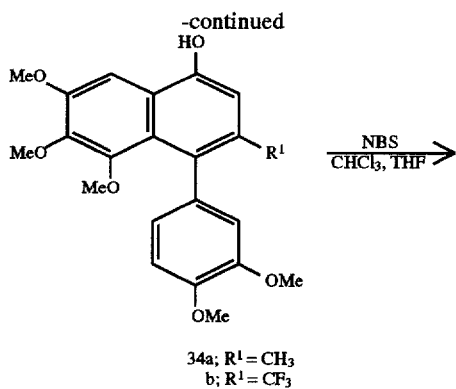

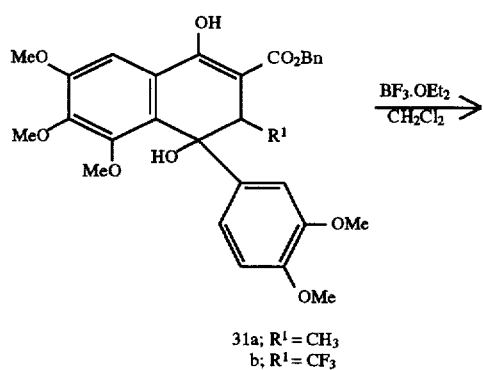

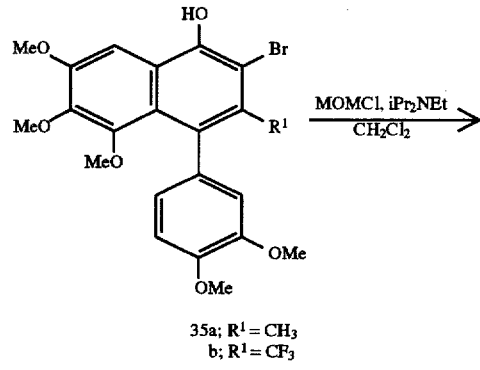

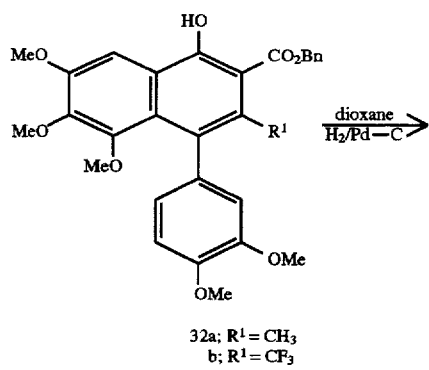

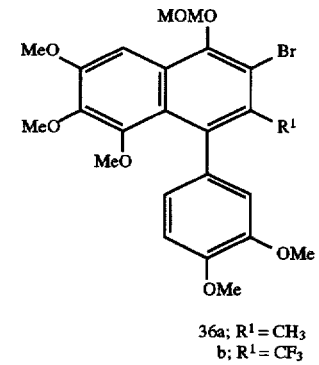

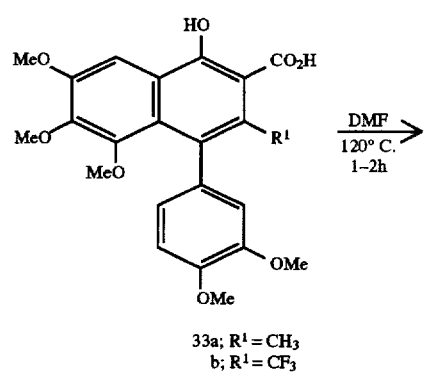

Step-1 (3-(Benzyloxy)carbonyl-1,2-dihydro-1,4-dihydroxy-1-(3,4-dimethoxyphenyl)-2-methyl-6,7,8-trimethoxynaphthalene: 31a)

Under nitrogen flow, 100 ml of 1.65M n-BuLi in n-hexane (165 mmol) was added dropwise to a solution of (TMS)$_2$NH (34.7 ml, 165 mmol) in 100 ml of dry THF under cooling in an ice-bath. After the addition, the mixture was stirred at the same temperature for 20 minutes and then cooled to −78° C. To the cooled solution, a solution of lactone VI-1 obtained in Preparation 16 (29.7 g, 82.5 mmol) in 100 ml of dry methylene chloride was added dropwise over 15 minutes. After stirring for additional 10 minutes, a solution of benzyl crotonate 30a (14.4 g, 82.5 mmol) in 35 ml of dry THF was added dropwise over 10 minutes. After the addition, the mixture was warmed to 0° C., and the reaction mixture was stirred under cooling in an ice-bath for 2.5 hours. To the reaction mixture was added ice and 50 ml of 2N HCl, and the resulting mixture was extracted with ethyl acetate. The extract was washed with water and brine, dried over anhydrous magnesium sulfate, and concentrated under reduced pressure to obtain 35 g of desired compound 31a as a crude oily product, which was used in the next step without purification.

Step-2 (3-(Benzyloxy)carbonyl-1-(3,4-dimethoxyphenyl)-4-hydroxy-2-methyl-6,7,8-trimethoxynaphthalene: 32a)

Under nitrogen atmosphere, $BF_3 \cdot OEt_2$ (20.3 ml, 165 mmol) was added under cooling in an ice-bath to a solution of 35 g of the crude compound 31a obtained above in 400 ml of dry methylene chloride, and the mixture was allowed to warm to room temperature while being stirred overnight. To the reaction mixture was added 23 ml of triethylamine, and the resulting mixture was stirred at room temperature for 10 minutes. Water was added to the reaction mixture, which was then extracted with methylene chloride. The extract was washed with 1N hydrochloric acid and brine, and dried over anhydrous magnesium sulfate. After concentration under reduced pressure, the residue was crystallized from methylene chloride:methanol to obtain 37.4 g (87.3%) of desired compound 32a.

mp: 153°–154° C.

$^1$H-NMR: $\delta(CDCl_3)$ 2.18(3H,s) 3.24(3H,s) 3.83(3H,s) 3.86(3H,s) 3.93(3H,s) 4.01(3H,s) 5.44(2H,s) 6.67–6.74(2H, m) 6.88(1H,d,J=8.2 Hz) 7.32–7.50(5H,m) 7.62(1H,s) 12.25 (1H,s) ppm Step-3 (1-(3,4-Dimethoxyphenyl)-4-hydroxy-2-methyl-6,7,8-trimethoxy-3-naphthoic acid: 33a)

Under hydrogen atmosphere, 1.0 g of 10% Pd—C was added to a solution of compound 32a (36.9 g, 71.1 mmol) in 300 ml of 1,3-dioxane, and the mixture was stirred at room temperature for one hour and 10 minutes. After filtering Pd—C off, the reaction mixture was concentrated under reduced pressure and the residue was crystallized from methanol to obtain 29.6 g (97.3%) of desired compound 33a.

mp: 185°–187° C. (dec.)

$^1$H-NMR: $\delta(CDCl_3)$ 2.28(3H,s) 3.26(3H,s) 3.86(3H,s) 3.88(3H,s) 3.96(3H,s) 4.02(3H,s) 6.70–6.77(2H,m) 6.93 (1H,d,J=9.0 Hz) 7.65(1H,s) 12.29(1H,s) ppm.

Step-4 (1-(3,4-Dimethoxyphenyl)-4-hydroxy-2-methyl-6,7,8-trimethoxynaphthalene: 34a)

Under nitrogen atmosphere, a solution of compound 33a (25.5 g, 59.6 mmol) in 100 ml of dry DMF was stirred for 1 hour and 50 minutes at 125° C. To the reaction mixture was slowly added 200 ml of water, and precipitated crystals were collected by filtration. Recrystallization from THF-methanol gave 20.5 g (89.6%) of desired compound 34a.

mp: 201°–202° C.

$^1$H-NMR: $\delta(CDCl_3)$ 2.02(3H,s) 3.29(3H,s) 3.84(3H,s) 3.86(3H,s) 3.95(3H,s) 3.99(3H,s) 5.56(1H,br.s) 6.68(1H,s) 6.72–6.78(2H,m) 6.91(1H,d,J=8.8 Hz) 7.37(1H,s) ppm.

Step-5 (3-Bromo-1-(3,4-dimethoxyphenyl)-4-hydroxy-2-methyl-6,7,8-trimethoxynaphthalene: 35a)

Under nitrogen atmosphere, 3.71 g (20.8 mmol) of N-bromosuccinimide was added to a solution of compound 34a (8.00 g, 20.8 mmol) in a mixture of 80 ml of chloroform and 40 ml of THF at −78° C. The reaction mixture was stirred for 35 minutes at the same temperature, and then allowed to warm to room temperature while being stirred for additional 1 hour and 40 minutes. To the reaction mixture was added aqueous sodium thiosulfate and the resulting mixture was extracted with methylene chloride. The extract was washed with water and brine, dried over anhydrous magnesium chloride, and concentrated under reduced pressure to obtain 10.5 g of desired compound 35a as a crude oily product, which was used in the next reaction without purification.

Step-6 (3-Bromo-1-(3,4-dimethoxyphenyl)-4-methoxymethoxy-2-methyl-6,7,8-trimethoxynaphthalene: 36a )

Diisopropylethylamine (7.96 ml, 45.8 mmol) and chloromethyl methyl ether (3.20 ml, 41.6 mmol ) were added to a solution of the crude compound 35a obtained above in 150 ml of methylene chloride, and the mixture was stirred overnight. After addition of 10 ml of methanol, methylene chloride was evaporated under reduced pressure. The residue was dissolved in ethyl acetate, washed with water and brine, and dried over anhydrous magnesium chloride. After concentration under reduced pressure, the residue was purified by medium pressure column chromatography (200 g of silica gel; ethyl acetate:n-hexane=1:2) to obtain 10.3 g (97.9%) of desired compound 36a as an oil.

$^1$H-NMR: $\delta(CDC_3)$ 2.18(3H,s) 3.27(3H,s) 3.79(3H,s) 3.84(6H,s) 3.95(3H,s) 4.00(3H,s) 5.27(2H,s) 6.69–6.76(2H, m) 6.92(1H,d,J=8.6 Hz) 7.44(1H,s) ppm.

Preparation 28

Synthesis of 3-bromo-1-(3,4-dimethoxyphenyl)-4-methoxymethoxy-2-(trifluoromethyl)-6,7,8-trimethoxynaphthalene: 36b The reactions were conducted similarly to those of preparation 27, to obtain compound 36b. Physical properties of compound 36b and intermediates thereof are shown below.

32b;

Yield 80.9% (through 2 steps)

mp: 147°–148° C. (methanol)

$^1$H-NMR: $\delta(CDCl_3)$ 3.20(3H,s) 3.82(3H,s) 3.86(3H,s) 3.94(3H,s) 4.03(3H,s) 5.39(2H,s) 6.81(1H,s) 6.85(2H,s) 7.35–7.49(5H,m) 7.61(1H,s) 10.54(1H,s) ppm 33b;

Quantitative yield mp: 154°–156° C. (dec.) (THF-isopropyl ether)

$^1$H-NMR: $\delta(CDCl_3)$ 3.24(3H,s) 3.85(3H,s) 3.89(3H,s) 3.96(3H,s) 4.05(3H,s) 6.85(1H,br.s) 6.89(2H,s) 7.65(1H,s) 10.82(1H,s) ppm 34b;

Yield 74.2% mp: 230°–231° C. (THF-methanol)

$^1$H-NMR: $\delta(CDCl_3)$ 3.28(3H,s) 3.84(3H,s) 3.85(3H,s) 3.95(3H,s) 4.03(3H,s) 6.07(1H,br.s) 6.79–6.91(3H,m) 7.07 (1H,s) 7.43(1H,s) ppm.

36b;

Yield 64.0% (through 2 steps), oil $^1$H-NMR: $\delta(CDCl_3)$ 3.21(3H,s) 3.79(3H,s) 3.84(3H,s) 3.85(3H,s) 3.94(3H,s) 4.03(3H,s) 5.30(2H,s) 6.75–6.90(3H, m) 7.52(1H,s) ppm Example 62

Synthesis of 1-(3,4-dimethoxyphenyl)-4-hydroxy-2-methyl-3-[4-(trifluoromethyl)benzoyl]-6,7,8-trimethoxynaphthalene: I-62

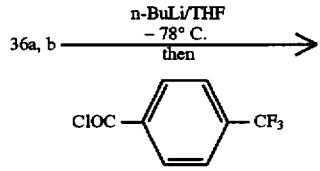

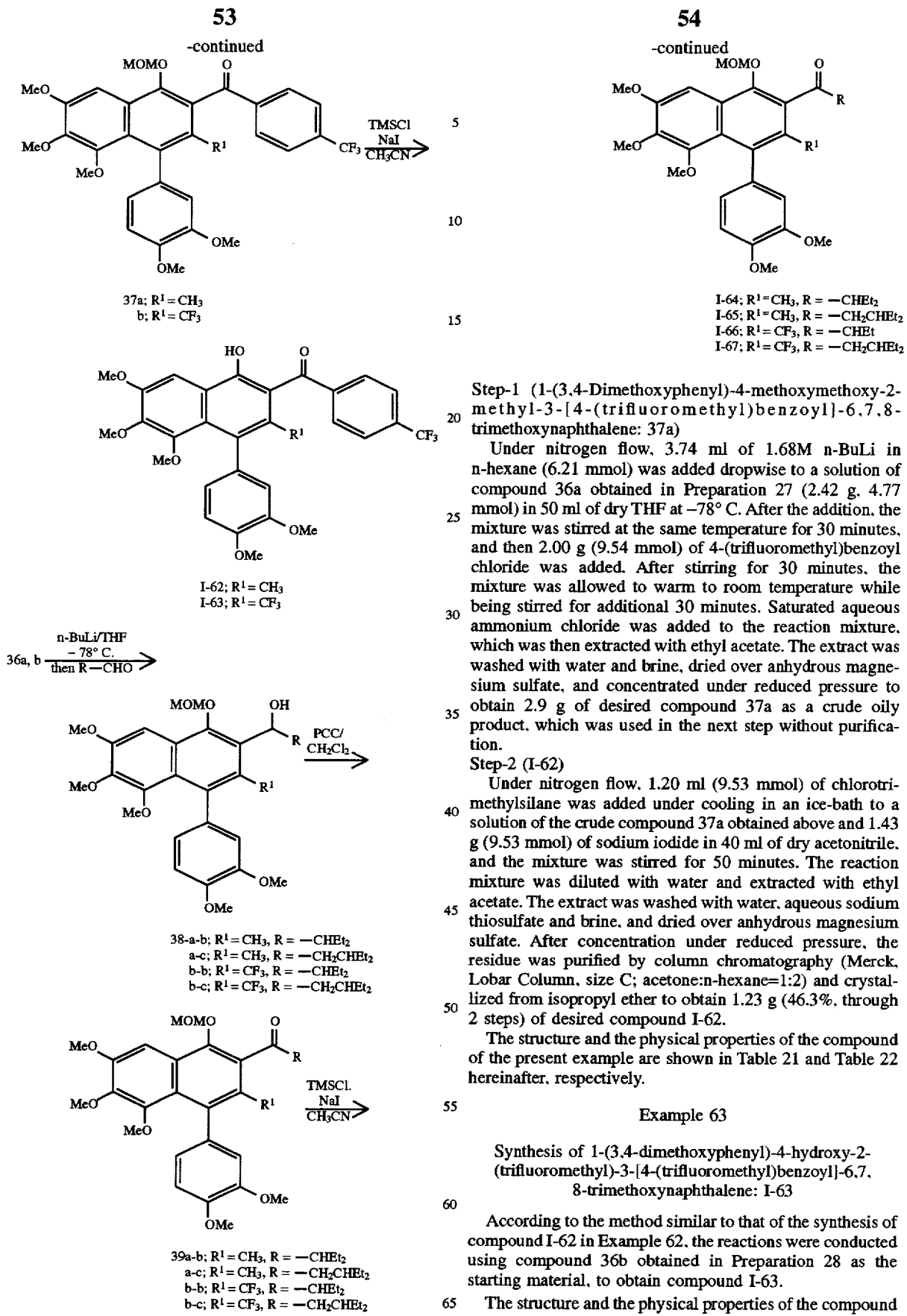

Step-1 (1-(3,4-Dimethoxyphenyl)-4-methoxymethoxy-2-methyl-3-[4-(trifluoromethyl)benzoyl]-6,7,8-trimethoxynaphthalene: 37a)

Under nitrogen flow, 3.74 ml of 1.68M n-BuLi in n-hexane (6.21 mmol) was added dropwise to a solution of compound 36a obtained in Preparation 27 (2.42 g, 4.77 mmol) in 50 ml of dry THF at −78° C. After the addition, the mixture was stirred at the same temperature for 30 minutes, and then 2.00 g (9.54 mmol) of 4-(trifluoromethyl)benzoyl chloride was added. After stirring for 30 minutes, the mixture was allowed to warm to room temperature while being stirred for additional 30 minutes. Saturated aqueous ammonium chloride was added to the reaction mixture, which was then extracted with ethyl acetate. The extract was washed with water and brine, dried over anhydrous magnesium sulfate, and concentrated under reduced pressure to obtain 2.9 g of desired compound 37a as a crude oily product, which was used in the next step without purification.

Step-2 (I-62)

Under nitrogen flow, 1.20 ml (9.53 mmol) of chlorotrimethylsilane was added under cooling in an ice-bath to a solution of the crude compound 37a obtained above and 1.43 g (9.53 mmol) of sodium iodide in 40 ml of dry acetonitrile, and the mixture was stirred for 50 minutes. The reaction mixture was diluted with water and extracted with ethyl acetate. The extract was washed with water, aqueous sodium thiosulfate and brine, and dried over anhydrous magnesium sulfate. After concentration under reduced pressure, the residue was purified by column chromatography (Merck, Lobar Column, size C; acetone:n-hexane=1:2) and crystallized from isopropyl ether to obtain 1.23 g (46.3%, through 2 steps) of desired compound I-62.

The structure and the physical properties of the compound of the present example are shown in Table 21 and Table 22 hereinafter, respectively.

Example 63

Synthesis of 1-(3,4-dimethoxyphenyl)-4-hydroxy-2-(trifluoromethyl)-3-[4-(trifluoromethyl)benzoyl]-6,7,8-trimethoxynaphthalene: I-63

According to the method similar to that of the synthesis of compound I-62 in Example 62, the reactions were conducted using compound 36b obtained in Preparation 28 as the starting material, to obtain compound I-63.

The structure and the physical properties of the compound of the present example are shown in Table 21 and Table 22 hereinafter, respectively.

Example 64

Synthesis of 1-(3,4-dimethoxyphenyl)-3-(2-ethyl-1-oxobutyl)-4-hydroxy-2-methyl-6,7,8-trimethoxynaphthalene: I-64

Step-1 (1-(3,4-Dimethoxyphenyl)-3-(2-ethyl-1-hydroxybutyl)-4-methoxymethoxy-2-methyl-6,7,8-trimethoxynaphthalene: 38a–b)

Under nitrogen flow, 7.57 ml (12.6 mmol) of 1.66M n-BuLi in n-hexane was added dropwise to a solution of compound 36a obtained in Preparation 27 (4.90 g, 9.66 mmol) in 200 ml of dry THF at −78° C. After the addition, the mixture was stirred for 30 minutes at the same temperature and, 2.37 ml (19.3 mmol) of 2-(ethyl)butyraldehyde was added thereto. After stirring for 15 minutes, the mixture was warmed to room temperature while being stirred for additional 1 hour and 40 minutes. To the reaction mixture was added saturated aqueous ammonium chloride, and the resulting mixture was extracted with ethyl acetate. The extract was washed with water and brine, and dried over anhydrous magnesium sulfate. After concentration under reduced pressure, the residue was purified by medium pressure column chromatography (200 g of silica gel; ethyl acetate:n-hexane=1:3 to 1:2) to obtain 3.91 g (76.5%) of desired compound 38a–b.

$^1$H-NMR: δ(CDCl$_3$) 0.73(3H,t,J=7.4 Hz) 0.99(3H,t,J=7.4 Hz) 1.03–1.20(2H,m) 1.50–1.97(3H,m) 2.14&2.15 (total 3H,each s) 2.12–2.32 (1H,m) 3.28(3H,s) 3.72(3H,s) 3.84 (6H,s) 3.95(3H,s) 3.99(3H,s) 5.03–5.25(3H,m) 6.68–6.77 (2H,m) 6.92(1H,d,J=8.8 Hz) 7.18 (1H,s) ppm.

Step-2 (1-(3,4-Dimethoxyphenyl)-3-(2-ethyl-1-oxobutyl)-4-methoxymethoxy-2-methyl-6,7,8-trimethoxynaphthalene: 39a–b)

To a solution of compound 38a–b obtained above (3.20 g, 7.37 mmol) in 100 ml of methylene chloride was added 4.78 g (22.1 mmol) of pyridinium chlorochromate (PCC), and the mixture was stirred at room temperature for 2 hours. The mixture was diluted with 200 ml of ether and filtered through Celite. After concentrating the filtrate under reduced pressure, the residue was purified by medium pressure column chromatography (200 g of silica gel; ethyl acetate:n-hexane=1:3) to obtain 2.88 g (90.0%) of desired compound 39a–b as an oil.

$^1$H-NMR: δ(CDCl$_3$) 0.96(3H,t,J=7.4 Hz) 0.97(3H,t,J=7.4 Hz) 1.48–1.95(4H,m) 1.90(3H,s) 2.83–2.92(1H,m) 3.29(3H, s) 3.64(3H,s) 3.85(3H,s) 3.86(3H,s) 3.95(3H,s) 4.00(3H,s) 5.06(2H,s) 6.70–6.78(2H,m) 6.92(1H,d,J=8.8 Hz) 7.46(1H, s) ppm.

Step-3 (Synthesis of I-64)

Under nitrogen flow, 2.06 ml (16.4 mmol) of chlorotrimethylsilane was added to a solution of compound 39a–b obtained above (2.88 g, 5.44 mmol) and 2.45 g (16.3 mmol) of sodium iodide in 60 ml of dry acetonitrile under cooling in an ice-bath, and the mixture was stirred for 20 minutes. To the reaction mixture was added water and the resulting mixture was extracted with ethyl acetate. The extract was washed with, water, aqueous sodium thiosulfate and brine, and dried over anhydrous magnesium sulfate. After concentration under reduced pressure, the residue was purified by column chromatography (Merck, Lobar Column, size C (2 columns); ethyl acetate:n-hexane=1:3) and crystallized from n-hexane to obtain 1.30 g (49.2%) of desired compound I-64.

The structure and the physical characteristics of the compound of the present example are shown in Table 21 and Table 22 hereinafter, respectively.

Examples 65 to 67

According to the method similar to that of Example 64, the reactions were conducted using compound 36a and 36b obtained in Preparations 27 and 28, respectively, as the starting materials, to obtain the compounds of Examples shown below. The structure and the physical properties of the compounds of the present example are shown in Table 21 and Table 23 hereinafter, respectively.

Example 65:

1-(3,4-Dimethoxyphenyl)-3-(3-ethyl-1-oxopentyl)-4-hydroxy-2-methyl-6,7,8-trimethoxynaphthalene Example 66:

1-(3,4-Dimethoxyphenyl)-3-(2-ethyl-1-oxobutyl)-4-hydroxy-2-(trifluoromethyl)-6,7,8-trimethoxynaphthalene Example 67:

1-(3,4-Dimethoxyphenyl)-3-(3-ethyl-1-oxopentyl)-4-hydroxy-2-(trifluoromethyl)-6,7,8-trimethoxynaphthalene TABLE 10
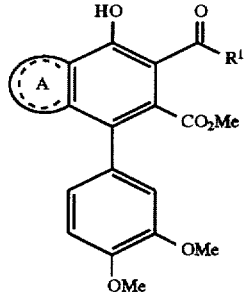
| (Method) | A ring | R¹ | | | | |
|---|---|---|---|---|---|---|
| | | −Et | −CHEt₂ | −CH₂CHEt₂ | 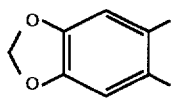 | 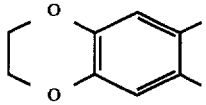 |
| (B) | 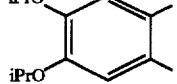 | Exam. 32 | Exam. 33 | | Exam. 34 | |
| (B) | 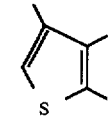 | Exam. 35 | | Exam. 36 | Exam. 37 | |
| (B) | 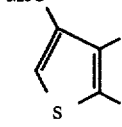 | Exam. 38 | Exam. 39 | | | Exam. 40 |
| (C) | 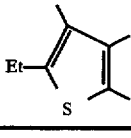 Me | Exam. 52 | Exam. 53 | | | |
| (C) | MeO (thiophene) | Exam. 54 | Exam. 55 | | | |
| (C) | MeO, Et (thiophene) | Exam. 56 | Exam. 57 | | | |

TABLE 11

[Structure: naphthalene with MeO groups at 6,7,8 positions, HO at 4, C(O)R¹ at 3, CO₂Me at 2, R³ at 1]

| (Method) | R³ | −Et | −CH₂CHEt₂ | −C₆H₄−CF₃ (para) |
|---|---|---|---|---|
| (C) | [3,4-difluorophenyl] | | Exam. 58 | |
| (C) | [3,4-dichlorophenyl] | | Exam. 59 | |
| (C) | [3,4-ethylenedioxyphenyl] | | Exam. 60 | |
| (C) | [3-fluoro-4-methoxyphenyl] | | Exam. 61 | |
| (B) | [2,4-dimethoxyphenyl] | Exam. 41 | Exam. 42 | Exam. 43 |

TABLE 12

| (Method) | R¹ |||
|---|---|---|---|
| | —Et | —CH₂CHEt₂ | —C₆H₄-CF₃ (p) |
| 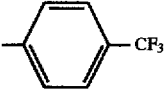 (B) | Exam. 44 | Exam. 45 | Exam. 46 |
| 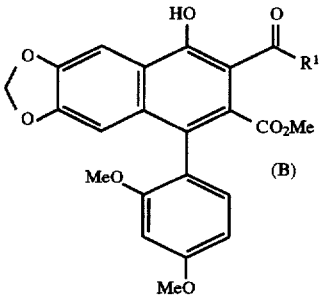 (B) | Exam. 47 | Exam. 48 | Exam. 49 |

TABLE 13

| Exam. No. | mp (°C.) | ¹H—NMR δ (CDCl₃) ppm | I R ν max (CHCl₃) cm⁻¹ |
|---|---|---|---|
| 32 | 169~170 (methylene chloride-methanol) | 1.19 (3H, t, J = 7.2 Hz), 2.81~2.91 (2H, m), 3.52 (3H, s), 3.86 (3H, s), 3.95 (3H, s), 6.06 (2H, s), 6.72 (1H, s), 6.79~6.92 (3H, m), 7.81 (1H, s), 14.36 (1H, s) | 1724, 1619, 1582, 1459, 1175, 1038, 1025 |
| 33 | 151~152 (methylene chloride-methanol) | 0.84 (6H, t, J = 7.2 Hz), 1.45~1.80 (4H, m), 3.49 (3H, s), 3.86 (3H, s), 3.96 (3H, s), 6.06 (2H, s), 6.75~6.97 (4H, m), 7.80 (1H, s), 13.98 (1H, s) | 1725, 1618, 1583, 1515, 1459, 1039, 1027 |
| 34 | 201~202 (methylene chloride-methanol) | 2.86 (3H, s), 3.83 (3H, s) 3.93 (3H, s), 6.09 (2H, s), 6.72~6.95 (4H, m), 7.35~7.62 (4H, m), .7.82 (1H, s), 12.12 (1H, s) | 1732, 1714, 1619, 1590, 1516, 1459, 1039, 1027 |
| 35 | 158~159 (methanol) | 1.18 (3H, t, J = 7.2 Hz), 2.79~2.90 (2H, m), 3.52 (3H, s), 3.86 (3H, s), 3.95 (3H, s), 4.32 (4H, s), 6.79~6.95 (4H, m), 7.95 (1H, s) 14.57 (1H, s) | 1722, 1612, 1581, 1503, 1422, 1180 |
| 36 | 159~160 (methanol) | 0.83 (6H, t, J = 7.4 Hz), 1.24~1.38 (4H, m), 1.20~2.12 (1H, m), 2.72 (2H, d, J = 7.2 Hz), 3.51 (3H, s), 3.86 (3H, s), 3.95 (3H, s), 4.33 (4H, s), 6.80 (1H, s), 6.82~6.93 (3H, m), 7.95 (1H, s), 14.37 (1H, s) | 1725, 1613, 1581, 1503, 1423, 1178, 1069, 1024 |
| 37 | 159~161 (methylene chloride-methanol) | 2.86 (3H, s), 3.83 (3H, s) 3.93 (3H, s), 4.35 (4H, s), 6.72~6.93 (3H, m) 6.99 (1H, s), 7.35~7.61 (4H, m), 7.96 (1H, s), 12.43 (1H, s) | 1732, 1714, 1590, 1505, 1423, 1368, 1291, 1068 |

TABLE 14

| Exam. No. | mp (°C.) | ¹H—NMR δ (CDCl₃) ppm | I R ν max (CHCl₃) cm⁻¹ |
|---|---|---|---|
| 38 | 120~121 (methylene chloride-methanol) | 1.19 (3H, t, J = 7.2 Hz), 1.25 (3H, d, J = 1.6 Hz), 1.27 (3H, t, J = 1.6 Hz), 1.42 (6H, d, J = 6.0 Hz), 2.80~2.91 (2H, m), 3.53 (3H, s) 3.85 (3H, s), 3.96 (3H, s), | 1721, 1609, 1575, 1512, 1495, 1495, 1461, 1437, 1416, 1375, 1187 |

TABLE 14-continued

| Exam. No. | mp (°C.) | ¹H—NMR δ (CDCl₃) ppm | I R ν max (CHCl₃) cm⁻¹ |
|---|---|---|---|
| 39 | 146–147 (methylene chloride-methanol) | 4.28–4.40 (1H, m), 4.66–4.78 (1H, m), 6.75 (1H, s), 6.82–6.98 (3H, m), 7.85 (1H, s), 14.49 (1H, s), 0.83 (6H, t, J = 7.4 Hz), 1.25–1.45 (16H, m), 2.00–2.13 (1H, m), 2.73 (2H, d, J = 6.6 Hz), 3.52 (3H, s), 3.86 (3H, s), 3.97 (3H, s), 4.28–4.40 (1H, m), 4.66–4.78 (1H, m), 6.78 (1H, s), 6.82–6.95 (3H, m), 7.85 (1H, s), 14.29 (1H, s) | 1722, 1608, 1575, 1512, 1495, 1461, 1437, 1417, 1374 |
| 40 | 137–138 isopropyl ether-n-hexane) | 1.29 (6H, d, J = 6 Hz), 1.46 (6H, d, J = 6.0 Hz), 2.77 (3H, s), 3.83 (3H, s), 3.94 (3H, s), 4.31–4.43 (1H, m), 4.70–4.82 (1H, m), 6.76–6.95 (4H, m), 7.64–7.76 (4H, m), 7.88 (1H, s), 12.60 (1H, s) | 1732, 1713, 1605, 1578, 1513, 1499, 1463, 1437, 1409, 1370, 1321, 1172, 1136 |

TABLE 15

| Exam. No. | mp (°C.) | ¹H—NMR δ (CDCl₃) ppm | I R ν max (CHCl₃) cm⁻¹ |
|---|---|---|---|
| 41 | 127–128 (methylene chloride-methanol) | 1.16 (3H, t, J = 7.2 Hz), 2.82–2.92 (2H, m), 3.24 (3H, s), 3.43 (3H, s), 3.70 (3H, s), 3.85 (3H, s), 3.88 (3H, s), 4.02 (3H, s), 6.42–6.51 (2H, m), 6.98 (1H, d, J = 8.2 Hz), 7.72 (1H, s), 14.60 (1H, s) | 1721, 1608, 1579, 1507, 1459, 1435, 1412, 1121 |
| 42 | 133–134 (methanol) | 0.83 (3H, t, J = 7.4 Hz), 0.84 (3H1 t, J = 7.4 Hz), 1.00–1.35 (4H, m), 1.98–2.10 (1H, m), 2.73 (1H, d, J = 1.6 Hz), 2.76 (1H, d, J = 1.0 Hz), 3.24 (3H, s), 3.43 (3H, s), 3.71 (3H, s), 3.85 (3H, s), 3.88 (3H, s), 4.02 (3H, s), 6.45–6.50 (2H, m) 6.98 (2H, d, J = 4.2 Hz), 7.71 (1H, s), 14.40 (1H, s) | 1724, 1608, 1580, 1207, 1507, 1487, 1460, 1434, 1412, 1376, 1141, 1060 |
| 43 | 136–137 (ethyl acetate-n-hexane) | 2.70 (3H, s), 3.24 (3H, s), 3.74 (3H, s) 3.81 (3H, s), 3.91 (3H, s), 4.05 (3H, s), 6.36–6.49 (2H, m), 6.84 (1H, d, J = 8 Hz), 7.62–7.76 (5H, m), 12.56 (1H, s) | 1734, 1710, 1608, 1581, 1508, 1486, 1460, 1321, 1134 |

TABLE 16

| Exam. No. | mp (°C.) | ¹H—NMR δ (CDCl₃) ppm | I R ν max (CHCl₃) cm⁻¹ |
|---|---|---|---|
| 44 | 145–146 (methylene chloride-methanol) | 1.17 (3H, t, J = 7.0 Hz), 2.80–2.91 (2H, m), 3.50, (3H, s), 3.69 (3H, s), 3.88 (3H, s), 6.03–6.05 (2H, m), 6.50–6.57 (2H, m), 6.62 (1H, s), 6.98–7.02 (1H, m), 7.79 (1H, s), 14.33 (1H, s) | 1725, 1611, 1581, 1510, 1459, 1378, 1040 |
| 45 | 123–124 (methylen chloride-methanol) | 0.82 (3H, t, J = 7.4 Hz), 0.83 (3H, t, J = 7.4 Hz), 1.20–1.40 (4H, m), 1.97–2.09 (1H, m), 2.72 (2H, d, J = 6.2 Hz), 3.50 (3H, s), 3.69 (3H, s), 3.87 (3H, s), 6.04 (2H, d, J = 0.4 Hz), 6.53–6.57 (2H, 1), 6.64 (1H, s), 7.01 (1H, d, J = 8.6 Hz), 7.26 (1H, s), 14.11 (1H, s) | 1726, 1611, 1581, 1510, 1459, 1379, 1173, 1040 |
| 46 | 119–120 (methylene choride-methanol) | 2.78 (3H, s), 3.68 (3H, s), 3.85 (3H, s), 6.08 (2H, s), 6.50–6.55 (2H, m), 6.79 (1H, s), 6.96 (1H, d, J = 9.0 Hz), 7.63–7.78 (4H, m), 7.82 (1H, s), 12.36 (1H, s) | 1732, 16H, 1586, 1510, 1459, 1406, 1367, 1321, 1133 |

TABLE 17

| Exam. No. | mp (°C.) | ¹H—NMR δ (CDCl₃) ppm | I R ν max (CHCl₃) cm⁻¹ |
|---|---|---|---|
| 47 | 152–153 (methylene chloride-methanol) | 1.18 (3H, t, J = 7.4 Hz), 2.79–2.90 (2H, m), 3.53 (3H, s), 3.63 (3H, s), 3.94 (3H, s), 6.04 (2H, s), 6.65 (1H, s), 6.69–6.72 (1H, m), 6.99–7.14 (2H, m), 7.80 (1H, s), 14.20 (1H, s) | 1726, 1626, 1579, 1496, 1459, 1379, 1076, 1040 |
| 48 | 109–110 (methylen chloride- | 0.79 (3H, t, J = 7.4 Hz), 0.83 (3H, t, J = 7.4 Hz), 1.20–1.18 (4H, m), 1.95–2.08 (1H, m), 3.53 (3H, s), 3.63 | 1726, 1620, 1597, 1579, 1497, 1459, 1436, 1402, 1377, 1075, |

TABLE 17-continued

| Exam. No. | mp (°C.) | $^1$H—NMR δ (CDCl$_3$) ppm | I R ν max (CHCl$_3$) cm$^{-1}$ |
|---|---|---|---|
|  | methanol) | (3H, s), 3.91 (3H, s), 6.03 (2H, s), 6.67–6.72 (2H, m), 6.98–7.10 (2H, m), 7.79 (1H, s), 13.92 (1H, s) | 1039 |
| 49 | 156–157 (methylene chloride-methanol) | 2.80 (3H, s), 3.66 (3H, s) 3.92 (3H, s), 6.08 (2H, s), 6.07–6.65 (1H, m), 6.76 (1H, s), 6.95–7.11 (2H, m), 7.62–7.77 (4H, m), 7.83 (1H, s), 12.30 (1H, s) | 1730, 1621, 1597, 1578, 1498, 1459, 1367, 1320, 1074 |

TABLE 18

| Exam. No. | mp (°C.) | $^1$H—NMR δ (CDCl$_3$) ppm | I R ν max (CHCl$_3$) cm$^{-1}$ |
|---|---|---|---|
| 52 | 145–146 (methanol) | 1.19 (3H, t, J = 7.0 Hz), 2.69 (3H, d, J = 1.3 Hz), 2.85 (2H, q, J = 7.0 Hz), 3.58 (3H, s), 3.87 (3H, s), 3.95 (3H, s) 6.90–6.94 (3H, m), 6.98 (1H, d, J = 1.3 Hz), 13.80 (1H, s) | 3350–2380, 1724, 1619 |
| 53 | 124–126 (methanol) | 0.83 (6H, t, J = 7.3 Hz), 1.18–1.38 (4H, m), 1.98–2.11 (1H, m), 2.69 (3H, d, J = 1.2 Hz), 2.72 (2H, d, J = 6.8 Hz), 3.57 (3H, s), 3.87 (3H, s), 3.94 (3H, s), 6.91–6.93 (3H, m), 6.98 (1H, d, J = 1.2 Hz), 13.57 (1H, s) | 3420–2400, 1725, 1619 |

TABLE 19

| Exam. No. | mp (°C.) | $^1$H—NMR δ (CDCl$_3$) ppm | I R ν max (CHCl$_3$) cm$^{-1}$ |
|---|---|---|---|
| 54 | 180–182 (methanol) | 1.22 (3H, t, J = 7.2 Hz), 3.05 (2H, q, J–7.2 Hz), 3.58 (3H, s), 3.86 (3H, s), 3.94 (3H, s), 4.05 (3H, s), 6.38 (1H, s), 6.89–6.99 (3H, m), 9.59 (1H, s) | 3446, 1722, 1678 |
| 55 | 127–129 (methanol) | 0.88 (6H, t, J = 7.3 Hz), 1.31–1.49 (4H, m), 1.92–2.14 (1H, m), 2.97 (2H, d, J = 6.8 Hz), 3.57 (3H, s), 3.86 (3H, s), 3.93 (3H, s), 4.05 (3H, s), 6.37 (1H, s), 6.89–6.99 (3H, m), 9.65 (1H, s) | 3440, 1725, 1672 |
| 56 | 115–117 (methanol) | 1.21 (3H, t, J = 7.4 Hz), 1.28 (3H, t, J = 7.4 Hz), 2.86 (2H, q, J = 7.4 Hz), 2.96 (2H, q, J = 7.4 Hz), 3.57 (3H, s), 3.87 (3H, s), 3.94 (3H, s), 3.98 (3H, s), 6.88–6.94 (3H, m), 11.43 (1H, s) | 3410, 1722, 1621 |
| 57 | oil | 0.86 (6H, t, J = 7.4 Hz), .1.23–1.43 (7H, m), 1.94–2.13 (1H, m), 2.80–2.93 (4H, m), 3.57 (3H, s), 3.87 (3H, s), 3.94 (3H, s), 3.98 (3H, s), 6.90–6.94 (3H, m), 11.39 (1H, s) | 3404, 3260–2380, 1725, 1669 1621 |

TABLE 20

| Exam. No. | mp (°C.) | $^1$H—NMR δ (CDCl$_3$) ppm | I R ν max (CHCl$_3$) cm$^{-1}$ |
|---|---|---|---|
| 58 | 110–112 (methanol) | 0.78–0.89 (6H, m), 1.20–1.40 (4H, m), 1.96–2.13 (1H, m), 2.70 (2H, d, J = 6.6 Hz) 3.27 (3H, s), 3.48 (3H, s), 3.89 (3H, s), 4.03 (3H, s), 6.93–7.22 (3H, m), 7.73 (1H, s), 14.31 (1H, s) | 2940, 2840, 1729, 1603, 1572, 1514, 1487, 1460, 1432, 1411, 1377, 1126, 1114, 1057 |
| 59 | 1.22–124 (methanol) | 0.89 (6H, t, J = 7.3 Hz), 1.18–1.42 (4H, m), 1.95–2.13 (1H, m), 2.70 (2H, d, J = 6.4 Hz), 3.27 (3H, s), 3.48 (3H, s), 3.89 (3H, s), 4.03 (3H, s), 7.13 (1H, dd, J = 8.0 Hz, 2.0 Hz), 7.40 (1H, d, J = 2.0 Hz), 7.42 (1H, d, J = 8.0 Hz), 7.72 (1H, s), 14.31 (1H, s) | 2960, 2940, 1730, 1605, 1572, 1489, 1460, 1433, 1412, 1380, 1144, 1126, 1106, 1061, 1030 |
| 60 | 139–141 (methanol) | 0.82 (6H, t, J = 7.4 Hz), 1.20–1.41 (4H, m), 1.95–2.13 (1H, m), 2.72 (2H, d, J = 6.6 Hz), 3.29 (3H, s), 3.48 (3H, s), 3.89 (3H, s), 4.03 (3H, s), 4.29 (4H, s) 6.70–6.87 (3H m), 7.71 (1H, s), 14.31 (1H, s) | 2960, 2935, 1728, 1605, 1582, 1503, 1488, 1460, 1432, 1410, 1375, 1300, 1280, 1131, 1069 |
| 61 | 121.5–123 | 0.76–0.90 (6H, m), 1.21–1.42 (4H, m), 1.94–2.13 | 2965, 2940, 1730, 1619, 1605, |

TABLE 20-continued

| Exam. No. | mp (°C.) | ¹H—NMR δ (CDCl₃) ppm | I R ν max (CHCl₃) cm⁻¹ |
|---|---|---|---|
| | (methanol) | (1H, m), 2.71 (2H, d, J = 6.6 Hz), 3.26 (3H, s), 3.47 (3H, s), 3.89 (3H, s), 3.94 (3H, s), 4.03 (3H, s) 6.87~ 7.14 (3H, m), 7.72 (1H, s), 14.32 (1H, s) | 1576, 1514, 1490, 1462, 1435, 1412, 1377, 1261, 1137, 1122, 1108, 1061, 1031 |

TABLE 21

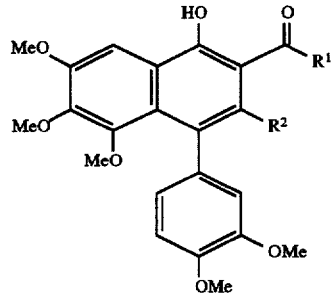

| (Method) | R² | —CHEt₂ | —CH₂CHEt₂ | —C₆H₄—CF₃ |
|---|---|---|---|---|
| — | —Me | Exam. 64 | Exam. 65 | Exam. 62 |
| — | CF₃ | Exam. 66 | Exam. 67 | Exam. 63 |

TABLE 22

| Exam. No. | mp (°C.) | ¹H—NMR δ (CDCl₃) ppm | I R ν max (CHCl₃) cm⁻¹ |
|---|---|---|---|
| 62 | 139–140 (isopropyl ether) | 1.61 (3H, s), 3.31 (3H, s), 3.83 (3H, s), 3.90 (3H, s) 3.92 (3H, s), 4.03 (3H, s), 6.67 (1H, d, J = 8.2 Hz, 1.8 Hz), 6.74 (1H, dd, J = 8.2 Hz,1.8 Hz), 6.90 (1H, d, J = 8.2 Hz), 7.65 (1H, s), 7.72 (2H, d, J = 8.0 Hz), 7.81 (2H, d, J = 8.0 Hz), 11.39 (1H, s) | 1606, 1581, 1512, 1185, 1463, 1420, 1364, 1324, 1170, 1135, 1070 |
| 63 | 215–217 (methanol) | 3.33 (3H, s), 3.83 (3H, s), 3.89 (3H, s), 3.94 (3H, s), 4.06 (3H, s), 6.77–6.91 (3H, m), 7.66 (1H, s), 7.71 (2H, d, J = 8. 0 Hz) 7.79 (2H, d, J = 8.0 Hz), 10.08 (1H, s) | 1630, 1605, 1579, 1513, 1487, 1462, 1420, 1371, 1324, 1137, 1064, 1050 |
| 64 | 108–109 (n-hexane) | 0.84 (3H, t, J = 7.4 Hz), 0.88 (3H, t, J = 7.4 Hz), 1.50– 1.88 (4H, m), 2.18 (3H, s), 3.12–3.29 (1H, m), 3.28 (3H, s), 3.86 (3H, s), 3.87 (3H, s), 3.95 (3H, s), 4.01 (3H, s), 6.69–6.81 (2H, m), 6.93 (1H, d, J = 8.2 Hz) 7.60 (1H, s), 12.00 (1H, s) | 2964, 1608, 1582, 1513, 1486, 1463, 1411, 1359, 1136, 1070, 1036 |

55

TABLE 23

| Exam. No. | mp (°C.) | ¹H—NMR δ (CDCl₃) ppm | I R ν max (CHCl₃) cm⁻¹ |
|---|---|---|---|
| 65 | oil | 0.84 (3H, t, J = 7.1 Hz), 0.85 (3H, t, J = 7.4 Hz), 1.20 ~ 1.43 (4H, m), 1.93–2.10 (1H, m), 2.18 (3H, s), 2.86 (2H, d, J = 6.8 Hz), 3.28 (3H, s), 3.86 (3H, s), 3.87 (3H, s), 3.95 (3H, s), 4.01 (3H, s), 6.70–6.80 (2H, m), 6.93 (1H, d, J = 8.0 Hz), 7.62 (1H, s), 12.57 (1H, s) | 3008, 2956, 2930, 1060, 1582, 1513, 1485, 1462, 1411, 1358, 1236, 1134, 1069 |

TABLE 23-continued

| Exam. No. | mp (°C.) | $^1$H—NMR δ (CDCl$_3$) ppm | I R ν max (CHCl$_3$) cm$^{-1}$ |
|---|---|---|---|
| 66 | 92–94 (n-hexane) | 0.78 (3H, t, J = 7.4 Hz), 0.85 (3H, t, J = 7.6 Hz), 1.39–1.79 (4H, m), 2.90–3.07 (1H, m), 3.28 (3H, s), 3.85 (3H, s), 3.86 (3H, s), 3.95 (3H, s), 4.04 (3H, s), 6.81 (1H, s), 6.88 (2H, s), 7.61 (1H, s), 10.79 (1H, s) | 2962, 1640, 1606, 1578, 1514, 1488, 1462, 1113, 1371, 1159, 1128, 1056, 1026 |
| 67 | 93–94 (n-hexane) | 0.78 (3H, t, J = 7.4 Hz), 0.81 (3H, t, J = 7.4 Hz), 1.17–1.35 (4H, m), 1.76–1.90 (1H, m), 2.80 (2H, d, J = 6.6 Hz), 3.28 (3H, s), 3.84 (3H, s), 3.87 (3H, s), 3.95 (3H, s), 4.04 (3H, s), 6.81 (1H, s), 6.89 (2H, s), 7.63 (1H, s), 11.07 (1H, s) | 2960, 1635, 1604, 1580, 1512, 1488, 1462, 1411, 371, 1158, 1124, 1056, 1025 |

Preparations of the present compounds having substituents on position 5 on ring A are described below.

Preparation 29

Synthesis of 6-(3,4-dimethoxyphenyl)-5-methoxycarbonyl-10-methyl-7,8,9-trimethoxy-4H-naphtho[1,2-d][1,3]dioxin-4-one: IV-11

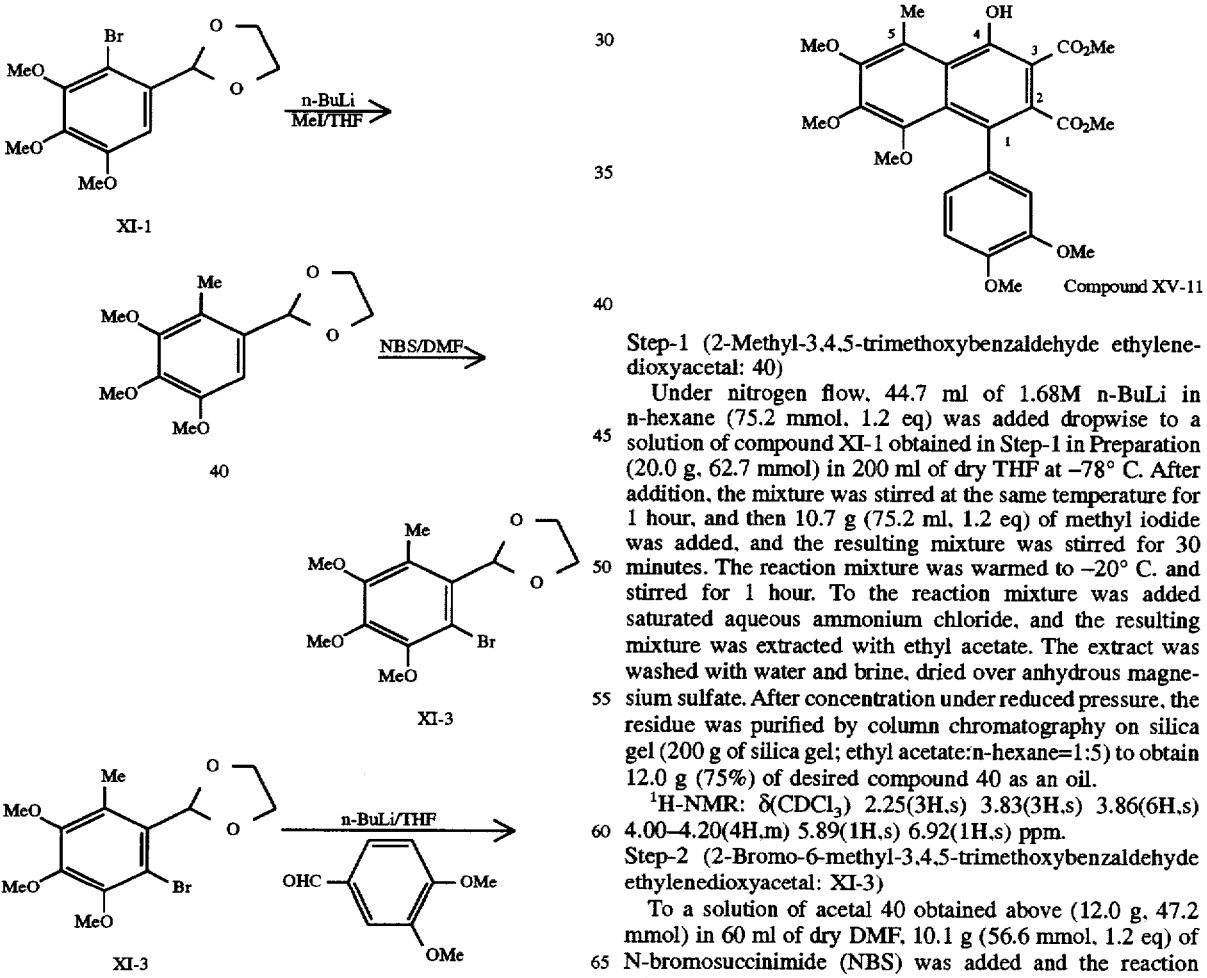

Step-1 (2-Methyl-3,4,5-trimethoxybenzaldehyde ethylenedioxyacetal: 40)

Under nitrogen flow, 44.7 ml of 1.68M n-BuLi in n-hexane (75.2 mmol, 1.2 eq) was added dropwise to a solution of compound XI-1 obtained in Step-1 in Preparation (20.0 g, 62.7 mmol) in 200 ml of dry THF at -78° C. After addition, the mixture was stirred at the same temperature for 1 hour, and then 10.7 g (75.2 ml, 1.2 eq) of methyl iodide was added, and the resulting mixture was stirred for 30 minutes. The reaction mixture was warmed to -20° C. and stirred for 1 hour. To the reaction mixture was added saturated aqueous ammonium chloride, and the resulting mixture was extracted with ethyl acetate. The extract was washed with water and brine, dried over anhydrous magnesium sulfate. After concentration under reduced pressure, the residue was purified by column chromatography on silica gel (200 g of silica gel; ethyl acetate:n-hexane=1:5) to obtain 12.0 g (75%) of desired compound 40 as an oil.

$^1$H-NMR: δ(CDCl$_3$) 2.25(3H,s) 3.83(3H,s) 3.86(6H,s) 4.00–4.20(4H,m) 5.89(1H,s) 6.92(1H,s) ppm.

Step-2 (2-Bromo-6-methyl-3,4,5-trimethoxybenzaldehyde ethylenedioxyacetal: XI-3)

To a solution of acetal 40 obtained above (12.0 g, 47.2 mmol) in 60 ml of dry DMF, 10.1 g (56.6 mmol, 1.2 eq) of N-bromosuccinimide (NBS) was added and the reaction mixture was stirred for 3 hours at 60° C. To the reaction mixture was added ice and water, and the resulting mixture was extracted with ethyl acetate. The extract was washed with water and brine, and dried over anhydrous magnesium sulfate. After concentration under reduced pressure, the residue was purified by column chromatography on silica gel (300 g of silica gel, ethyl acetate:n-hexane=1:5) and crystallized from n-hexane to obtain 8.25 g (52%) of desired compound XI-3 as crystals.

mp: 84°–85° C.

$^1$H-NMR: δ(CDCl$_3$) 2.33(3H,s) 3.81(3H,s) 3.84(3H,s) 3.92(3H,s) 4.00–4.08(2H,m) 4.19–4.25(2H,m) 6.35(1H,s) ppm.

Step-3 (2,3-Bis(methoxycarbonyl)-1-(3,4-dimethoxyphenyl)-4-hydroxy-5-methyl-6,7,8-trimethoxynaphthalene: XV-11)

i) Under nitrogen flow, 41.6 ml of 1.68M n-BuLi in n-hexane (69.8 mmol, 1.1 eq) was added dropwise to a solution of bromide XI-3 obtained above (21.2 g, 63.5 mmol) in 200 ml of dry THF at −78° C. After addition, the mixture was stirred at the same temperature for 1 hour and then a solution of 11.6 g (69.8 ml, 1.1 eq) of 3,4-dimethoxybenzaldehyde in 20 ml of dry THF was added thereto dropwise. After stirring for 1 hour, saturated aqueous ammonium chloride was added and the resulting mixture was extracted with ethyl acetate. The extract was washed with water and brine, dried over anhydrous magnesium sulfate and concentrated under reduced pressure to obtain desired acetalalcohol II-11 as a crude product, which was used in the next step without purification.

ii) To a solution of compound II-11 obtained above in 200 ml of dry benzene, 1.08 g (76.3 mmol, 1.2 eq) of dimethyl acetylenedicarboxylate (DMAD) and 15 mg of p-toluenenesulfonic acid were added, and the mixture was heated under reflux for 2 hours. After concentration under reduced pressure, the residue was crystallized from isopropyl ether, and then recrystallized from methanol to obtain 23.1 g (73%) of desired ester XV-11.

mp: 132°–133° C.

$^1$H-NMR: δ(CDCl$_3$) 2.87(3H,s) 3.20(3H,s) 3.46(3H,s) 3.84(3H,s) 3.86(3H,s) 3.90(6H,s) 3.92(3H,s) 6.78–6.85(3H, m) 13.03(1H,s) ppm. IR: ν(nujol) 1736,1654,1574,1028, 1013,989 cm$^{-1}$.

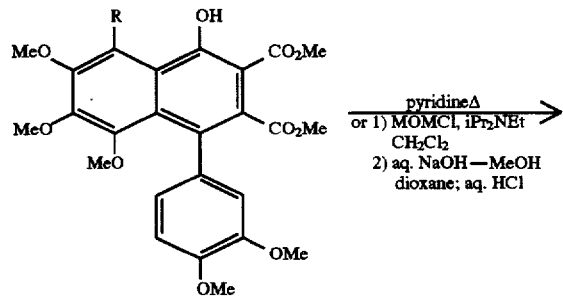

Compound (XV)

XV-11; R = Me
XV-12; R = OMe
XV-14; R = CH$_2$OMe
XV-13; R = CH$_2$OH ⎤ DHP, PPTS
XV-16; R = CH$_2$OTHP ⎦ CH$_2$Cl$_2$

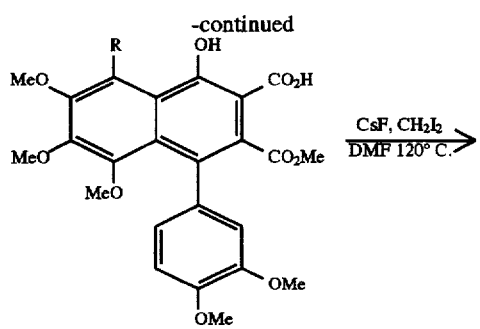

XVI-11; R = Me
XVI-12; R = OMe
XVI-14; R = CH$_2$OMe
XVI-16; R = CH$_2$OTHP

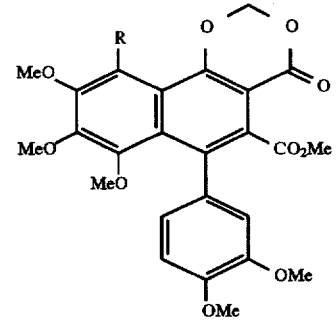

Compound (IV)

IV-11; R = Me
IV-12; R = OMe
IV-14; R = CH$_2$OMe
IV-16; R = CH$_2$OTHP

Step-4 (1-(3,4-Dimethoxyphenyl)-4-hydroxy-2-(methoxycarbonyl)-5-methyl-6,7,8-trimethoxy-3-naphthoic acid: XVI-11)

i) To a solution of ester XV-11 obtained above (6.53 g, 13.1 mmol) in 65 ml of dry methylene chloride, 5.56 g (43.1 mmol, 3.3 eq) of diisopropylethylamine and 3.16 g (39.2 mmol, 3.0 eq) of chloromethyl methy ether were added and the reaction mixture was stirred at room temperature for 4 hours. Ice water and 1N hydrochloric acid were added, and the resulting mixture was extracted with methylene chloride. The extract was washed with water and brine, dried over anhydrous magnesium sulfate, and concentrated under reduced pressure to obtain desired MOM ether, which was used in the next reaction without purification.

ii) The crude MOM ether obtained above was dissolved in 30 ml of dioxane, and to the resulting solution were added 6.58 g (11.7 mmol, 9 eq) of potassium hydroxide, 19.7 ml of water and 25 ml of methanol. The mixture was stirred for 40 hours at room temperature. To the reaction mixture was added 16 ml of concentrated hydrochloric acid, and the mixture was stirred at room temperature for 1.5 hours and then concentrated under reduced pressure. To the residue was added water and the mixture was extracted with methylene chloride. The extract was washed with water and brine and dried over anhydrous magnesium sulfate. After concentration under reduced pressure, the residue was crystallized from isopropyl ether to obtain 6.06 g (95%) of desired naphthoic acid XVI-11.

mp: 176°–178° C. (dec.)

$^1$H-NMR: δ(CDCl$_3$) 2.86(3H,s) 3.20(3H,s) 3.47(3H,s) 3.84(3H,s) 3.86(3H,s) 3.91(3H,s) 3.92(3H,s) 6.80–6.85(3H, m) 2.91(1H,s) ppm.

Step-5 (Synthesis of IV-11)

Under nitrogen flow, to a solution of compound XVI-11 (16.0 g, 32.9 mmol) in 128 ml of dry DMF, 15.0 g (98.7 mmol, 3.0 eq) of cesium fluoride and 13.2 g (49.3 mmol, 1.5 eq) of methylene iodide were added, and the mixture was stirred for 3 hours at 120° C. To the reaction mixture, ice and water were added, and the mixture was extracted with ethyl acetate. The extract was washed with water, aqueous sodium thiosulfate, and brine, and dried over anhydrous magnesium chloride. After concentration under reduced pressure, the residue was purified by column chromatography on silica gel (200 g of silica gel; ethyl acetate:n-hexane=1:2) and crystallized from ethyl acetate-isopropyl ether to obtain 7.50 g (46%) of desired lactone (IV-11) as crystals.

mp: 125°–126° C.

$^1$H-NMR: δ(CDCl$_3$) 2.76(3H,s) 3.22(3H,s) 3.57(3H,s) 3.84 (3H,s) 3.88(3H,s) 3.91(3H,s) 3.92(3H,s) 5.78(1H,d ABtype,J=7.2 Hz) 5.80(1H,d ABtype,J=7.2 Hz) 6.77–6.87 (3H,m) ppm.

Preparation 30

Synthesis of 6-(3,4-dimethoxyphenyl)-5-methoxycarbonyl-7,8,9,10-tetramethoxy-4H-naphtho[1,2-d][1,3]-dioxin-4-one: IV-12

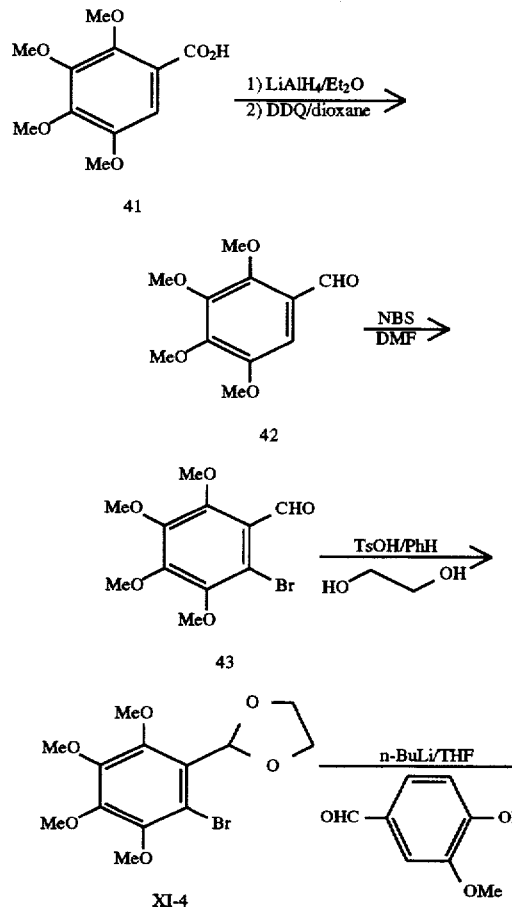

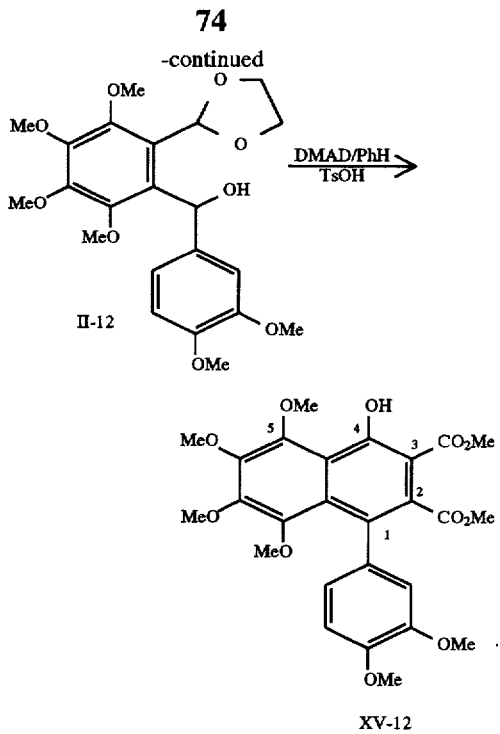

Step-1. (2,3,4,5-Tetramethoxybenzaldehyde: 42)

Under nitrogen flow, to a suspension of 2.12 g (55.8 mmol) of lithium aluminium hydride in 90 ml of dry THF, a solution of 9.00 g (37.2 mmol) of carboxylic acid 41 [A. I. Meyers, Joseph R. Flisak and R. Alan Aitken, J. Am. Chem. Soc. 109, 5446 (1987)] in 45 ml of dry THF was added dropwise under cooling in an ice-bath. After addition, the reaction mixture was stirred for 45 minutes at 60° C., cooled in an ice-bath, and then to the residue was added successively 2 ml of water 2 ml of 10% aqueous sodium hydroxide and 6 ml of water. The mixture was allowed to warm to room temperature while being stirred for 1 hour. The reaction mixture was filtered through Celite, and the filtrate was dried over anhydrous magnesium sulfate. After concentration under reduced pressure, the residue was dissolved in 45 ml of dry dioxane. To this solution 10.1 g (44.6 mmol, 1.2 eq) of DDQ was added, and the mixture was stirred overnight. The reaction mixture was filtered, and the filter cake was washed with n-hexane. The filtrate and the washing were combined and concentrated under reduced pressure. The residue was dissolved in ether, washed with 1N aqueous solution of sodium hydroxide, water and brine, and then dried over anhydrous magnesium sulfate. After concentration under reduced pressure, the residue was purified by column chromatography on silica gel (160 g of silica gel; ethyl acetate:n-hexane=1:5) to obtain 6.54 g (78%) of desired aldehyde 42 as an oil.

$^1$H-NMR: δ(CDCl$_3$) 3.88(3H,s) 3.94(3H,s) 3.98(3H,s) 4.00(3H,s) 7.11(1H,s) 10.30(1H,s) ppm.

Step-2 (2-Bromo-3,4,5,6-tetramethoxybenzaldehyde: 43)

The reaction was conducted similarly to that of the synthesis of compound XI-3 (Step-2 in Preparation 29), to obtain bromide 43 as an oil in 86% yield from aldehyde 42.

$^1$H-NMR: δ(CDCl$_3$) 3.86 (3H,s) 3.92(3H,s) 3.93(3H,s) 4.03(3H,s) 10.28(1H,s) ppm.

Step-3 (2-Bromo-3,4,5,6-tetramethoxybenzaldehyde ethylenedioxyacetal: XI-4)

To a solution of bromide 43 obtained above (2.00 g, 6.56 mmol) in 10 ml of benzene, 813 mg (13.1 mmol, 2.0 eq) of ethylene glycol and 25 mg (0.13 mmol) of p-toluenesulfonic acid were added, and the mixture was heated under reflux for 30 minutes to effect dehydration by using Dean Stark trap packed with molecular sieves 4A. To the reaction mixture was added saturated aqueous sodium bicarbonate, and the mixture was extracted with ethyl acetate. The extract was washed with water and brine, dried over anhydrous magnesium sulfate, and concentrated under reduced pressure to obtain 2.26 g of desired acetal XI-4 as a crude oily product.

$^1$H-NMR: δ(CDCl$_3$) 3.83(3H,s) 3.85(3H,s) 3.90(3H,s) 3.94(3H,s) 4.00–4.08(2H,m) 4.26–4.30(2H,m) 6.34(1H,s) ppm.

Step-4 (2,3-Bis(methoxycarbonyl)-1-(3,4-dimethoxyphenyl)-4-hydroxy-5,6,7,8-tetramethoxynaphthalene: XV-12)

The reactions were conducted similarly to those of the synthesis of compound XV-11 (Step-3 in Preparation 29), to obtain 9.60 g (66%) of ester XV-12 as crystals from bromide XI-4 obtained above (9.85 g).

mp: 115°–116° C. (ethyl acetate-isopropyl ether)

$^1$H-NMR: δ(CDCl$_3$) 3.19(3H,s) 3.46(3H,s) 3.83(3H,s) 3.90(3H,s) 3.92(3H,s) 3.94(3H,s) 4.02(6H,s) 6.78–6.83(3H, m) 12.31(1H,s) ppm.

IR: ν(nujol) 3226,1731,1596,1235,1205,1168,1096,1064, 1026 cm$^{-1}$.

Step-5 (1-(3,4-Dimethoxyphenyl)-4-hydroxy-2-(methoxycarbonyl)-5,6,7,8-tetramethoxy-3-naphthoic acid: XVI-12)

The reactions were conducted similarly to those of the synthesis of compound XVI-11 (Step-4 in Preparation 29), to obtain 6.24 g (94%) of naphthoic acid XVI-12 as crystals from ester XV-12 (6.83 g).

mp: 133°–135° C. (methanol)

$^1$H-NMR: δ(CDCl$_3$) 3.21(3H,s) 3.53(3H,s) 3.83(3H,s) 3.92(3H,s) 3.94(3H,s) 4.04(3H,s) 4.17(3H,s) 6.80–6.83(3H, m) 12.45(1H,s) ppm.

Step-6 (Synthesis of IV-12)

The reaction was conducted similarly to that of the synthesis of compound IV-11 (Step-5 in Preparation 29), to obtain 4.84 g (51%) of lactone IV-12 as crystals from naphthoic acid XVI-12 (9.36 g).

mp: 175°–176° C. (methylene chloride-isopropyl ether)

$^1$H-NMR: δ(CDCl$_3$) 3.21(3H,s) 3.58(3H,s) 3.84(3H,s) 3.93(3H,s) 3.94(3H,s) 3.96(3H,s) 4.04(3H,s) 5.83(1H,d ABtype,J=7.2 Hz) 5.85(1H,d AB type,J=7.2 Hz) 6.78–6.88 (3H,m) ppm.

Preparation 31

Synthesis of 6-(3,4-dimethoxyphenyl)-5-methoxycarbonyl-10-methoxymethyl-7,8,9-trimethoxy-4H-naphtho[1,2-d][1,3]dioxin-4-one: IV-14

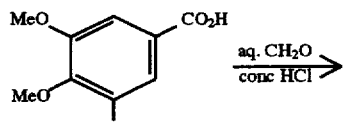

44

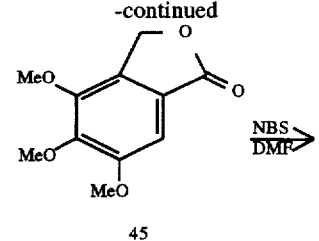

45

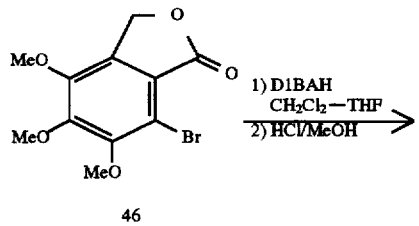

46

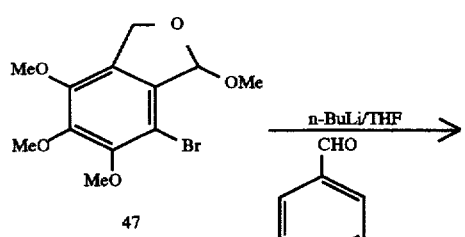

47

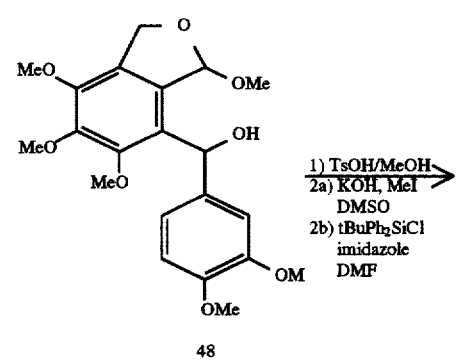

48

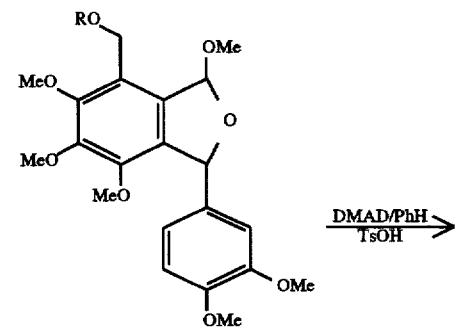

49; R = H
50; R = Me
51; R = SiPh$_2$Bu$^t$

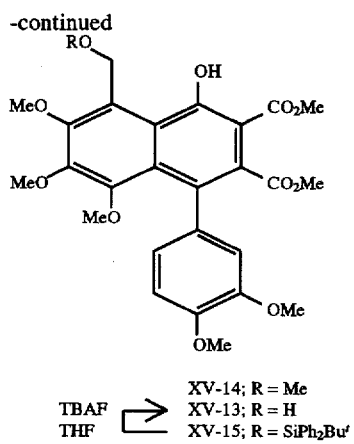

```
                 XV-14; R = Me
       TBAF      XV-13; R = H
       THF       XV-15; R = SiPh₂Buᵗ
```

Step-1 (4,5,6-Trimethoxyphthalide: 45)

According to the method disclosed in Japanese Patent Publication No. S62-000080, carboxylic acid 44 (60.0 g) was reacted to obtain 36.4 g (57%) of phthalide 45 as crystals.

mp: 136°–138° C.

Step-2 (7-Bromo-4,5,6-trimethoxyphthalide: 46)

The reaction was conducted similarly to that of Step-2 in Preparation 29 using compound 45 (21.6 g) as a starting material, to obtain 28.2 g (91%) of bromide 46 as crystals.

mp: 106°–108° C.

Step-3 (7-Bromo-1,3-dihydro-1,4,5,6-tetramethoxyisobenzofuran: 47)

i) Under nitrogen atmosphere, to a solution of bromide 46 obtained above (28.2 g, 93.0 mmol) in 232 ml of dry methylene chloride, 68 ml of 1.5M diisobutylaluminium hydride in toluene (102 mmol, 1.1 eq) was added dropwise over 30 minutes at −78° C., and the mixture was stirred at the same temperature for 1 hour. To the reaction mixture was added saturated aqueous ammonium chloride, and the resulting mixture was poured into aqueous acetic acid, and extracted with methylene chloride. The extract was washed with water, saturated aqueous sodium bicarbonate and brine, dried over anhydrous magnesium sulfate, and concentrated under reduced pressure to obtain desired hemiacetal as a crude product, which was used in the next step without purification.

ii) A solution of the crude hemiacetal obtained above in 30 ml of methanol was added dropwise to 100 ml of 0.37M hydrochloric acid in methanol under cooling in an ice-bath, and the mixture was stirred at room temperature for 30 minutes. To the reaction mixture was added saturated aqueous sodium bicarbonate, and the mixture was extracted with ether. The extract was washed with water and brine, dried over anhydrous magnesium sulfate, and concentrated under reduced pressure to obtain 28.6 g (97%, through 2 steps from compound 46) of desired acetal 47 as a crude product, which was used in the next step without purification.

$^{1}$H-NMR: $\delta$(CDCl$_3$) 3.52(3H,s) 3.89(3H,s) 3.90(3H,s) 3.90(3H,s) 5.09(1H,d ABtype,J=12.8 Hz) 5.28(1H,dd ABXtype,J=12.8 and 2.0 Hz) 6.01(1H,d ABtype) ppm.

Step-4 (2,3-Bis(methoxycarbonyl)-1-(3,4-dimethoxyphenyl)-4-hydroxy-5-methoxymethyl-6,7,8-trimethoxynaphthalene: XV-14)

i) The reaction was conducted similarly to that of Step-3 (i) in Preparation 29 using dihydroisobenzofuran 47 (5.09 g, 16.0 mmol) as a starting material, to obtain alcohol 48 as an oil, which was used in the next reaction without purification.

ii) To a solution of the crude alcohol 48 in 50 ml of methanol was added 25 mg of p-toluenesulfonic acid, and the mixture was stirred for 45 minutes at room temperature. To the reaction mixture was added saturated aqueous sodium bicarbonate and extracted with ether. The extract was washed with water and brine, dried over anhydrous magnesium sulfate, and concentrated under reduced pressure to obtain alcohol 49 as an oil, which was used in the next step without purification.

iii) To a solution of the crude alcohol 49 obtained above in 30 ml of DMSO, 3.70 g (65.7 mmol, 4.1 eq) of potassium hydroxide was added, and the reaction mixture was stirred for 5 minutes at room temperature. To this reaction mixture, 4.68 g (33.0 mmol, 2.1 eq) of methyl iodide was added, and the mixture was stirred for 30 minutes at room temperature. To the reaction mixture was added ice water, and the mixture was extracted with ethyl acetate. The extract was washed with water and brine, dried over anhydrous magnesium sulfate, and concentrated under reduced pressure to obtain desired ether 50 as an oil, which was used in the next step without purification.

iv) To a solution of the crude ether 50 obtained above in 50 ml of benzene, 2.81 g (19.8 mmol, 1.2 eq) of dimethyl acetylenedicarboxylate (DMAD) and 20 mg of p-toluenesulfonic acid were added, and the mixture was heated under reflux for 1 hour. The reaction mixture was washed with saturated aqueous sodium bicarbonate, water and brine, dried over anhydrous magnesium sulfate, and concentrated under reduced pressure. The residue was washed with methanol, and recrystallized from methanol to obtain 3.82 g (overall yield: 44%) of desired ester XV-14.

mp: 142°–144° C.

$^{1}$H-NMR: $\delta$(CDCl$_3$) 3.21(3H,s) 3.46(3H,s) 3.53(3H,s) 3.84(3H,s) 3.88(3H,s) 3.91(3H,s) 3.92(3H,s) 3.96(3H,s) 5.17(2H,s) 6.73–6.86(3H,m) 13.04(1H,s) ppm.

IR: $\nu$(nujol) 3270–2380, 1729, 1662 cm$^{-1}$.

Step-5 (1-(3,4-Dimethoxyphenyl)-4-hydroxy-2-methoxycarbonyl-5-methoxymethyl-6,7,8-trimethoxy-3-naphthoic acid: XVI-14)

A solution of ester XV-14 obtained above (7.80 g, 14.7 mmol) in 40 ml of pyridine was heated under reflux for 4 hours. To the reaction mixture was added ice water and 1N hydrochloric acid, and the mixture was extracted with ethyl acetate. The extract was washed with water and saturated brine, and dried over anhydrous magnesium sulfate. After concentration under reduced pressure, the residue was crystallized from isopropyl ether, and recrystallized from methylene chloride-isopropyl ether to obtain 5.80 g (76%) of desired naphthoic acid XVI-14.

mp: 147° C. (dec.)

Step-6 (Synthesis of IV-14)

The reaction was conducted similarly to that of Step-5 in Preparation 29 using naphthoic acid XVI-14 (5.80 g) as a starting material to obtain 3.58 g (60%) of lactone IV-14 as crystals.

mp: 120°–123° C.

Preparation 32

Synthesis of 6-(3,4-dimethoxyphenyl)-5-methoxycarbonyl-10-[(tetrahydropyranyl)oxy]methyl-7,8,9-trimethoxy-4H-naphtho[1,2-d][1,3]dioxin-4-one: IV-16

Step-1 (2,3-Bis(methoxycarbonyl)-5-(t-butyldiphenylsiloxy)methyl-1-(3,4-dimethoxyphenyl)-4-hydroxy-6,7,8-trimethoxynaphthalene: XV-15)

i) The reactions were conducted similarly to those of the synthesis of compound XV-14 (Step-4 in Preparation 31) using dihydroisobenzofuran 47 (15.4 g, 48.5 mmol) as a starting material, to obtain alcohol 49 as an oil, which was used in the next reaction without purification.

ii) To a solution of the crude alcohol 49 obtained above in 80 ml of DMF, 8.26 g (121 mmol, 2.5 eq) of imidazole and 16.0 g (58.2 mmol, 1.2 eq) of t-butylchlorodiphenylsilane were added, and the mixture was stirred for 20 minutes at room temperature. To the reaction mixture was added ice water, and the mixture was extracted with ether. The extract was washed with water and brine, dried over anhydrous magnesium sulfate, and concentrated under reduced pressure to obtain desired silylether 51 as an oil, which was used in the next step without purification.

iii) The reaction was conducted similarly to that of the synthesis of compound XV-14 (Step-4 in Preparation 31) using the crude silylether 51 obtained above as a starting material, to obtain 11.8 g (overall yield: 32%) of desired XV-15.

mp: 155°–156° C. (methanol)

$^1$H-NMR: δ(CDCl$_3$) 1.05(9H,s) 3.23(3H,s) 3.47(3H,s) 3.76(3H,s) 3.84(3H,s) 3.85(3H,s) 3.89(3H,s) 3.92(3H,s) 5.47(2H,s) 6.77–6.87(3H,m) 7.31–7.52(3H,m) 7.71–7.79 (3H,m) 12.72(1H,s) ppm.

Step-2 (2,3-Bis(methoxycarbonyl)-1-(3,4-dimethoxyphenyl)-4-hydroxy-5-hydroxymethyl-6,7,8-trimethoxynaphthalene: XV-13)

To a solution of silylether XV-15 obtained above (1.80 g, 2.35 mmol) in 15 ml of THF, 2.81 ml of 1M tetrabutylammonium fluoride in THF (2.81 mmol, 1.2 eq) was added, and the mixture was stirred at room temperature for 3 hours. To the reaction mixture was added ice water, and the mixture was extracted with ethyl acetate. The extract was washed with water and saturated brine, and dried over anhydrous magnesium sulfate. After concentration under reduced pressure, the residue was purified by column chromatography on silica gel (40 g of silica gel; methanol:methylene chloride=1:24) and crystallized from methanol to obtain 1.12 g (93%) of desired alcohol XV-13 as crystals.

mp: 157°–158.5° C.

$^1$H-NMR: δ(CDCl$_3$) 3.23(3H,s) 3.47(3H,s) 3.84(3H,s) 3.90(3H,s) 3.92(3H,s) 3.94(6H,s) 3.98(3H,s) 5.23(2H,s) 6.74–6.86(3H,m) 13.63(1H,s) ppm.

IR: ν(nujol) 3270–2370, 1730, 1660 cm$^{-1}$.

Step-3 (2,3-Bis(methoxycarbonyl)-1-(3,4-dimethoxyphenyl)-4-hydroxy-5-[(tetrahydropyranyl)oxy]methyl-6,7,8-trimethoxynaphthalene: XV-16)

To a solution of ester XV-13 obtained above (9.40 g, 18.2 mmol) in 50 ml of dry methylene chloride, 4.59 g (54.6 mmol, 3.0 eq) of dihydropyrane and 91 mg (0.36 mmol, 0.02 eq) of pyridinium p-toluenesulfonate were added, and the mixture was heated under reflux for 4 hours. The reaction mixture was washed with saturated aqueous sodium bicarbonate, water and brine, and dried over anhydrous magnesium sulfate. After concentration under reduced pressure, the residue was crystallized from 90% aqueous methanol to obtain 9.70 g (89%) of THP ether XV-16.

mp: 131°–133° C.

Step-4 (Synthesis of IV-16)

i) The reactions were conducted similarly those of the synthesis of compound XVI-14 (Step-5 in Preparation 31) using ester XV-16 obtained above (9.70 g, 16.1 mmol) as a starting material, to obtain naphtholic acid XVI-16 as a foamy material, which was used in the next reaction without purification.

ii) The reaction was conducted similar to that of the synthesis of compound IV-11 (Step-5 in Preparation 29) using the crude naphthoic acid XVI-16 obtained above was employed as a starting material, to obtain 5.27 g (overall yield: 55%) of lactone IV-16 as crystals.

mp: 157°–159° C.

$^1$H-NMR: δ(CDCl$_3$) 1.47–1.82(6H,s) 3.25(3H,s) 3.42–3.72(2H,m) 3.58(3H,s) 3.84(3H,s) 3.91(3H,s) 3.93 (3H,s) 3.98(3H,s) 4.73–4.86(1H,m) 5.05(1H,d ABtype,J= 10.2 Hz) 4.44(1H,dd ABXtype,J=10.2 and 2.4 Hz) 5.76–5.87(2H,m) 6.76–6.92(3H,m) ppm.

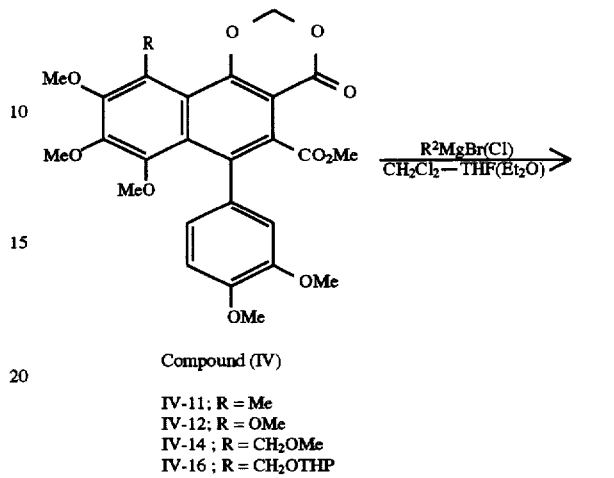

Compound (IV)

IV-11; R = Me
IV-12; R = OMe
IV-14 ; R = CH$_2$OMe
IV-16 ; R = CH$_2$OTHP

Compound I
R$^2$ = CH$_2$CHEt$_2$
I-68; R$^1$ = Me
I-69; R$^1$ = OMe
I-70; R$^1$ = CH$_2$OMe
; R$^1$ = CH$_2$OTHP
I-71; R$^1$ = CH$_2$OH AcOH
aq. THF Examples 68 to 79

Example 68:

Synthesis of 1-(3,4-dimethoxyphenyl)-3-(3-ethyl-1-oxopentyl)-4-hydroxy-2-methoxycarbonyl-5-methyl-6,7,8-trimethoxynaphthalene Using compound IV-11 (Preparation 29), the reaction was conducted similarly to that of Method B in Example 1 to obtain the title compound.

Example 69:

Synthesis of 1-(3,4-dimethoxyphenyl)-3-(3-ethyl-1-oxopentyl)-4-hydroxy-2-methoxycarbonyl-5,6,7,8-tetramethoxynaphthalene Using compound IV-12 (Preparation 30), the reaction was conducted similarly to that of Method B in Example 1 to obtain the title compound.

Example 70:

Synthesis of 1-(3,4-dimethoxyphenyl)-3-(3-ethyl-1-oxopentyl)-4-hydroxy-2-methoxycarbonyl-5-methoxymethyl-6,7,8-trimethoxynaphthalene Using compound IV-14 (Preparation 31), the reaction was conducted similarly to that of Method B in Example 1 to obtain the title compound.

Example 71:

Synthesis of 1-(3,4-dimethoxyphenyl)-3-(3-ethyl-1-oxopentyl)-4-hydroxy-5-hydroxymethyl-2-methoxycarbonyl-6,7,8-trimethoxynaphthalene Using compound IV-16 (Preparation 32), the reaction was conducted similarly to that of Method B in Example 1 to obtain a ketonic compound, whose THP protecting group was removed by treatment with acetic acid:THF:water (4:2:1) to obtain the title compound.

Example 72:

Synthesis of 1-(3,4-dimethoxyphenyl)-3-(1-oxopropyl)-4-hydroxy-2-methoxycarbonyl-5-methyl-6,7,8-trimethoxynaphthalene Using ethylmagnesium bromide, the reaction was conducted similarly to that of Example 68 to obtain the title compound.

Example 73:

Synthesis of 1-(3,4-dimethoxyphenyl)-3-(1-oxopropyl)-4-hydroxy-2-methoxycarbonyl-5,6,7,8-tetramethoxynaohthalene Using ethylmagnesiumbromide, the reaction was conducted similarly to that of Example 69 to obtain the title compound.

Example 74:

Synthesis of 1-(3,4-dimethoxyphenyl)-3-(1-oxopropyl)-4-hydroxy-2-methoxycarbonyl-5-methoxymethyl-6,7,8-trimethoxynaphthalene Using ethylmagnesium bromide, the reaction was conducted similarly to that of Example 70 to obtain the title compound.

Example 75:

Synthesis of 1-(3,4-dimethoxyphenyl)-3-(1-oxopropyl)-4-hydroxy-5-hydroxymethyl-2-methoxycarbonyl-6,7,8-trimethoxynaphthalene Using ethylmagnesium bromide, the reactions were conducted similarly to those of Example 71 to obtain the title compound.

Example 76:

Synthesis of 1-(3,4-dimethoxyphenyl)-3-(2-methyl-1-oxo-propyl)-4-hydroxy-2-methoxycarbonyl-5-methyl-6,7,8-trimethoxynaphthalene Using isopropylmagnesium bromide, the reaction was conducted similarly to that of Example 68 to obtain the title compound.

Example 77:

Synthesis of 1-(3,4-dimethoxyphenyl)-3-(2-methyl-1-oxopropyl)-4-hydroxy-2-methoxycarbonyl-5,6,7,8-tetramethoxynaphthalene Using isopropylmagnesium bromide, the reaction was conducted similarly to that of Example 69 to obtain the title compound.

Example 78:

Synthesis of 3-benzoyl-1-(3,4-dimethoxyphenyl)-4-hydroxy-2-methoxycarbonyl-5-methyl-6,7,8-trimethoxynaphthalene Using phenylmagnesium bromide, the reaction was conducted similarly to that of Example 68 to obtain the title compound.

Example 79:

Synthesis of 1-(3,4-dimethoxyphenyl)-3-(4-chlorobenzoyl)-4-hydroxy-5-hydroxymethyl-2-methoxycarbonyl-6,7,8-trimethoxynaphthalene Using 4-chlorophenylmagnesium bromide, the reactions were conducted similarly to those of Example 71 to obtain the title compound.

Table 24 shows the structures of the compounds listed above, and Table 25 and 26 show the physical properties thereof.

TABLE 24

[Structure: naphthalene core with substituents: R at position shown, HO, O, R¹, MeO, MeO, MeO, CO₂Me, and a phenyl ring with two OMe groups]

| R | R¹ | | | | |
|---|---|---|---|---|---|
|   | —Et | —CHMe₂ | —CH₂CHEt₂ | 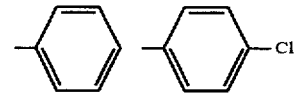 | |
| —Me | Exam No. 72 | Exam. No. 76 | Exam No. 68 | Exam No. 78 | |

TABLE 24-continued

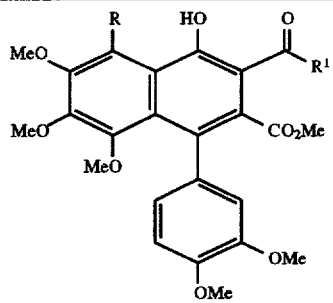

| R | —Et | —CHMe$_2$ | —CH$_2$CHEt$_2$ | 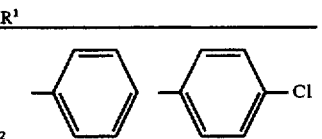 |
|---|---|---|---|---|
| —OMe | Exam No. 73 | Exam No. 77 | Exam No. 69 | |
| —CH$_2$OMe | Exam No. 74 | | Exam No. 70 | |
| —CH$_2$OH | Exam No. 75 | | Exam No. 71 | Exam No. 79 |

TABLE 25

| Exam. No. | mp (°C.) | $^1$H—NMR δ (CDCl$_3$) ppm | I R ν max (cm$^{-1}$) |
|---|---|---|---|
| 68 | oil | 0.82 (6H, t, J = 7 Hz) 1.25–1.40 (1H, m) 1.98–2.10 (1H, m) 2.70 (2H, d, J = 6 Hz) 2.86 (3H, s) 3.17 (3H, s) 3.43 (3H, s) 3.86 (6H, s) 3.90 (3H, s) 3.92 (3H, s) 6.75–6.85 (3H, m) 15.19 (1H, s) | (CHCl$_3$) 1725, 1605, 1255, 1237, 1219, 1082, 1009 |
| 69 | 103–104 (isopropyl ether-n-hexane) | 0.89 (6H, t, J = 7 Hz) 1.32–1.47 (4H, m), 1.94–2.08 (1H, m) 3.05 (2H, 1, J = 6 Hz) 3.19 (3H, s) 3.43 (3H, s) 3.82 (3H, s) 3.91 (3H, s) 3.92 (3H, s) 4.02 (3H, s) 4.13 (3H, s) 6.78–6.81 (3H, m), 10.90 (1H, s) | (nujol) 3234, 1714, 1697, 1595, 1295, 1237, 1075, 1054, 1628 |
| 70 | 130–132 | 0.87 (6H, t, J = 7.8 Hz), 1.28–1.46 (4H, m) 2.92 (2H, d ABtype, J = 6.6 Hz) 3.23 (3H, s) 3.43 (3H, s) 3.57 (3H, s) 3.84 (3H, s) 3.87 (3H, s) 3.91 (6H, s) 3.96 (3H, s) 5.07 (2H, s) 6.73–6.86 (3H, m) 11.93 (1H, s) | (nujol) 3360–2380, 1725 |
| 71 | 107–109 (methanol) | 0.83 (6H, dt, J = 7.3 Hz, 2.0 Hz) 1.22–1.41 (4H, m) 1.96–2.13 (1H, m) 2.75 (2H, d, J = 6.4 Hz) 3.21 (3H, s) 3.44 (3H, s) 3.86 (3H, s) 3.90 (3H, s) 3.92 (3H, s) 3.97 (6H, s) 5.21 (2H, s) 6.72–6.88 (3H, m) 15.74 (1H, s) | (nujol) 3558, 1727, 1616 |
| 72 | 117–118 (methylene chloride-n-hexane) | 1.17 (3H, t, J = 7 Hz) 2.77–2.81 (2H, m) 2.86 (3H, s) 3.18 (3H, s) 3.43 (3H, s) 3.85 (3H, s) 3.86 (3H, s) 3.90 (3H, s) 3.92 (3H, s) 6.75–6.85 (3H, m) 15.37 (1H, s) | (nujol) 1729, 1614, 1564, 1154, 1134, 1111, 1045, 1026, 1009 |

TABLE 26

| Exam. No. | mp (°C.) | $^1$H—NMR δ (CDCl$_3$) ppm | I R ν max (nujol) cm$^{-1}$ |
|---|---|---|---|
| 73 | 114–115 (methylene chloride-isopropyl ether) | 1.21 (3H, t, J = 7 Hz), 3.04–3.17 (2H, m) 3.19 (3H, s) 3.44 (3H, s) 3.83 (3H, s) 3.91 (3H, s) 3.93 (3H, s) 4.02 (3H, s) 4.1.3 (3H, s) 6.81–6.92 (3H, m) 10.90 (1H, s) | 3240, 1742, 1700, 1235, 1211, 1137, 1119, 1088, 1067, 1044 |
| 74 | 134.5–136.5 | 1.19 (3H, t, J = 7.2 Hz) 2.93–3.07 (2H, m) 3.24 (3H, s) 3.43 (3H, s) 3.57 (3H, s) 3.83 (3H, s) 3.87 (3H, s) 3.91 (6H, s) 3.95 (3H, s) 5.06 (2H, s) 6.73–6.86 (3H, m), 11.80 (1H, s) | 3350–2390, 1719 |
| 75 | 144–146 | 1.18 (3H, t, J = 7.1 Hz) 2.89 (2H, q, J = 7.1 Hz) 3.21 (3H, s) 3.45 (3H, s) 3.86 (3H, s) 3.90 (3H, s) 3.92 | 3560, 1725, 1618 |

TABLE 26-continued

| Exam. No. | mp (°C.) | $^1$H—NMR δ (CDCl$_3$) ppm | I R ν max (nujol) cm$^{-1}$ |
|---|---|---|---|
| | | (3H, s) 3.97 (6H, s) 5.21 (2H, s) 6.71–6.87 (3H, m) 15.88 (1H, s) | |
| 76 | 105–106 (methylene chloride-n-hexane) | 1.12 (3H, t, J = 7 Hz) 1.15 (3H, t, J = 7 Hz) 2.86 (3H, s) 3.06–3.22 (1H, m) 3.17 (3H, s) 3.42 (3H, s) 3.86 (6H, s) 3.89 (3H, s) 1.92 (3H, s) 6.75–6.87 (3H, m) 14.56 (1H, s) | 1716, 1613, 1569, 1239, 1137, 1046, 1028, 1009 |
| 77 | 171–172 (methylene chloride-isopropyl ether) | 1.22 (6H, t, J = 7 Hz) 3.20 (3H, s) 3.42 (3H, s) 3.56–3.70 (1H, m) 3.83 (3H, s) 3.91 (3H, s) 3.93 (3H, s) 4.03 (3H, s) 4.13 (3H, s) 6.75–6.85 (3H, m) 10.76 (1H, s) | 3276, 1743, 1677, 1592, 1236, 1209, 1072, 1048, 1022 |
| 78 | 140–141 (ethyl acetate-isopropyl ether) | 2.70 (3H, s) 2.90 (3H, s) 3.17 (3H, s) 3.82 (3H, s) 3.873 (3H, s) 3.89 (3H, s) 3.92 (3H, s) 6.75–6.85 (3H, m) 7.30–7.70 (5H, m) 13.41 (1H, s) | 1705, 1604, 1572, 1219, 1080, 1030, 1013 |
| 79 | 158–160 (ethyl acetate-isopropyl ether) | 2.87 (3H, s), 3.22 (3H, s), 3.83 (3H, s), 3.89 (3H, s), 3.81 (3H, s), 3.99 (3H, s), 5.25 (2H, s), 6.72–6.82 (3H, s), 7.39 (2H, d, J = 8.6 Hz), 7.63 (2H, d, J = 8.6 Hz), 13.19 (1H, s) | 3566, 3460–2400, 1735, 1715, 1665 |

An alternative method of preparation of the present compound is described below.

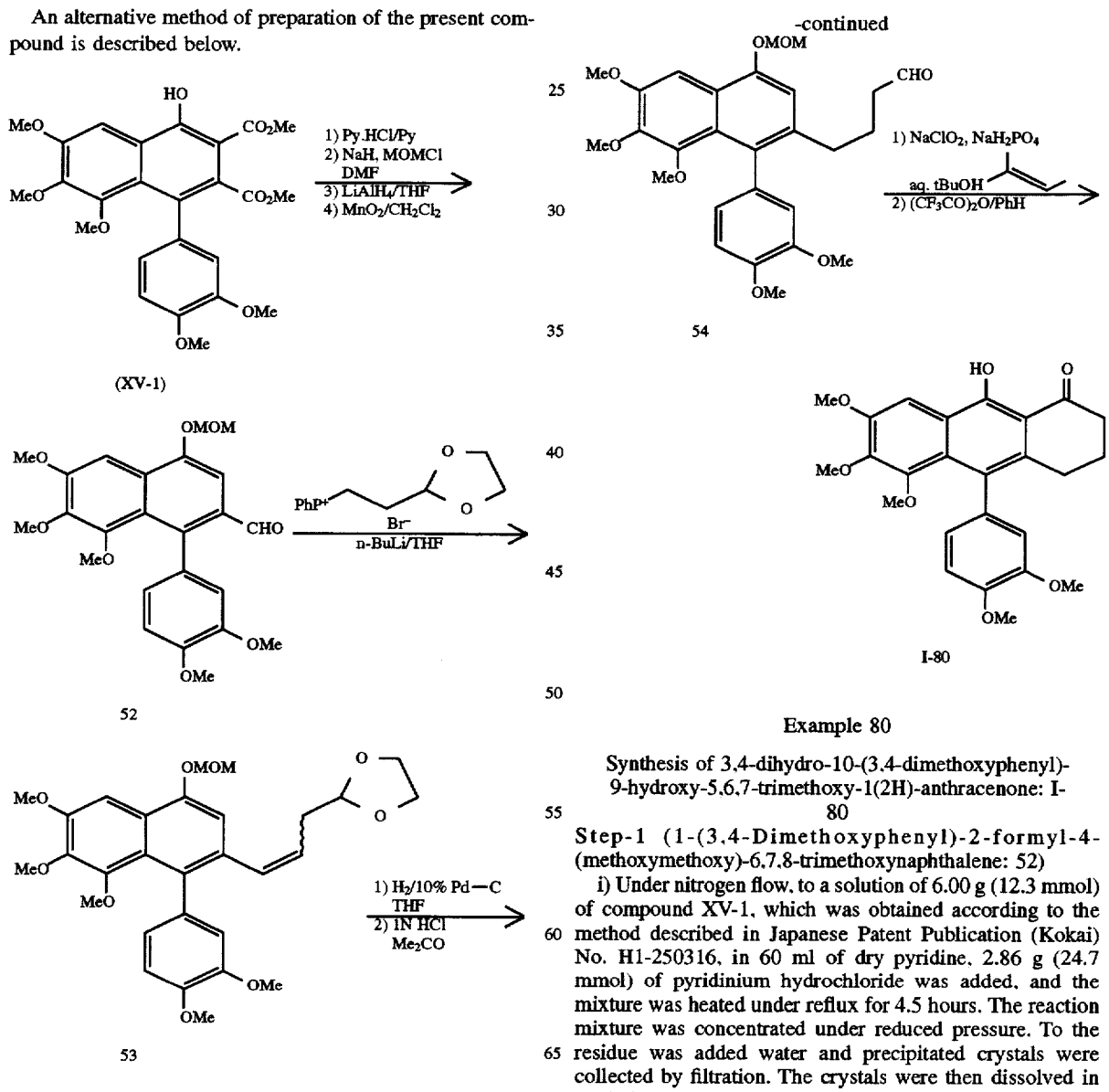

Example 80

Synthesis of 3,4-dihydro-10-(3,4-dimethoxyphenyl)-9-hydroxy-5,6,7-trimethoxy-1(2H)-anthracenone: I-80

Step-1 (1-(3,4-Dimethoxyphenyl)-2-formyl-4-(methoxymethoxy)-6,7,8-trimethoxynaphthalene: 52)

i) Under nitrogen flow, to a solution of 6.00 g (12.3 mmol) of compound XV-1, which was obtained according to the method described in Japanese Patent Publication (Kokai) No. H1-250316, in 60 ml of dry pyridine, 2.86 g (24.7 mmol) of pyridinium hydrochloride was added, and the mixture was heated under reflux for 4.5 hours. The reaction mixture was concentrated under reduced pressure. To the residue was added water and precipitated crystals were collected by filtration. The crystals were then dissolved in methylene chloride, and the solution was washed with water, dried over anhydrous magnesium sulfate. After concentration under reduced pressure, 5.20 g of crude crystal of desired de-methoxycarbonylated compound, which was used in the next step without purification.

mp: 223°–225° C.

$^1$H-NMR: δ(CDCl$_3$) 3.26(3H,s) 3.50(3H,s) 3.85(3H,s) 3.88(3H,s) 3.93(3H,s) 4.01(3H,s) 6.46(1H,s) 6.76–6.92(3H, m) 7.07(1H,s) 7.44(1H,s) ppm.

ii) The reaction was conducted similarly to that of Step-2 in Preparation 2 using 5.20 g of the crude crystal of phenol obtained above as a starting material, to obtain 5.90 g of crude crystals of MOM ether, which was used in the next step without purification.

mp: 128°–130° C.

$^1$H-NMR: δ(CDCl$_3$) 3.26(3H,s) 3.53(3H,s) 3.57(3H,s) 3.84(3H,s) 3.88(3H,s) 3.93(3H,s) 4.03(3H,s) 5.43(2H,s) 6.78–6.90(3H,m) 7.25(1H,s) 7.48(1H,s) ppm.

iii) The reaction was conducted similarly to reduction in Step-1 in Preparation 30 using 5.90 g of the crude crystals of methyl ester obtained above as a starting material, to obtain 5.82 g of alcohol as a crude foamy product, which was used in the next step without purification.

$^1$H-NMR: δ(CDCl$_3$) 3.29(3H,s) 3.58(3H,s) 3.84(3H,s) 3.86(3H,s) 3.95(3H,s) 4.01(3H,s) 4.40(2H,s) 5.44(2H,s) 6.77–6.95(3H,m) 7.24(1H,s) 7.47(1H,s) ppm.

iv) Under nitrogen flow, 55 g of manganese dioxide (679 mmol) was added in 5 portions at the interval of 10 minutes to a solution of 5.82 g of the crude alcohol obtained above in 120 ml of dry methylene chloride, and the reaction mixture was stirred for 40 minutes at room temperature. The reaction mixture was filtered through Celite, and the filter cake was washed with methylene chloride. The filtrate and the washing were combined and concentrated under reduced pressure. The residue was crystallized from ether-n-hexane to obtain 4.95 g (overall yield: 91%) of desired aldehyde 52 as crystals.

mp: 124.5°–126° C.

$^1$H-NMR: δ(CDCl$_3$) 3.33(3H,s) 3.58(3H,s) 3.85(3H,s) 3.88(3H,s) 3.96(3H,s) 4.05(3H,s) 4.47(2H,s) 6.83–6.97(3H, m) 7.53(1H,s) 7.54(1H,s) 9.64(1H,s) ppm.

Step-2 (1-(3,4-Diemthoxyphenyl)-4-(methoxymethoxy)-2-(4-oxobutyl)-6,7,8-trimethoxynaphthalene: 54)

i) Under nitrogen flow, 11.0 ml (18.5 mmol) of 1.67M n-butyllithium in n-hexane was added dropwise to a suspension of 8.20 g (18.5 mmol) of [2-(1,3-dioxolan-2-yl)ethyl]triphenylphosphonium bromide in 150 ml of dry THF at room temperature. After the addition, the mixture was stirred for 30 minutes, and then a solution of aldehyde 52 (5.00 g, 11.3 mmol) in 60 ml of dry THF was added dropwise thereto over 10 minutes. After stirring for 30 minutes, saturated aqueous ammonium chloride was added, and the mixture was extracted with ethyl acetate. The extract was washed with water and brine, and dried over anhydrous magnesium sulfate. After concentration under reduced pressure, the residue was purified by medium pressure column chromatography on silica gel (250 g of silica gel; ethyl acetate:toluene=1:4) to obtain 6.15 g of desired olefin 53 as an oil, which was used in the next step without purification.

ii) Under hydrogen atmosphere, 500 mg of 10% Pd—C was added to a solution of olefin 53 obtained above (6.15 g) in 20 ml of THF, and the mixture was stirred at room temperature for 2 hours. Pd—C was filtered off, and the reaction mixture was concentrated under reduced pressure to obtain 6.08 g of desired hydrogenated compound as an oil, which was used in the next step without purification.

$^1$H-NMR: δ(CDCl$_3$) 1.44–1.72(4H,m) 2.30–2.46(2H,m) 3.28(3H,s) 3.58(3H,s) 3.84(3H,s) 3.73–3.92(4H,m) 3.95 (3H,s) 4.00(3H,s) 4.69(1H,t,J=4.6 Hz) 5.41(2H,s) 6.72–6.81 (2H,m) 6.87–6.93(1H,m) 6.98(1H,s) 7.43(1H,s) ppm.

iii) To a solution of 6.08 g of the crude acetal obtained above in 120 ml of acetone was added 30 ml of 1N hydrochloric acid, and the mixture was stirred overnight at room temperature. The reaction mixture was neutralized with saturated aqueous sodium bicarbonate and extracted with ethyl acetate. The extract was washed with water and brine, and dried over anhydrous magnesium sulfate. After concentration under reduced pressure, the residue was purified by medium pressure column chromatography on silica gel (Merck, Lobar column, size C (2 columns); ethyl acetate:n-hexane=2:3) to obtain 3.65 g (overall yield: 67%) of desired aldehyde 54 as an oil.

$^1$H-NMR: δ(CDCl$_3$) 1.70–1.89(2H,m) 2.23–2.48(4H,m) 3.28(3H,s) 3.58(3H,s) 3.83(3H,s) 3.85(3H,s) 3.95(3H,s) 4.00(3H,s) 5.41(2H,s) 6.72–6.81(2H,m) 6.87–6.94(1H,m) 6.97(1H,s) 7.44(1H,s) 9.62(1H,t,J=1.8 Hz) ppm.

Step-3 (Compound I-80)

i) Aqueous solution (60 ml) of sodium chlorite (3.42 g, 37.8 mmol) and sodium dihydrogen phosphate dihydrate (4.47 g, 28.6 mmol) was added to a solution of aldehyde 54 (3.65 g, 7.54 mmol) and 2-methyl-2-butene (15.2 g, 217 mmol) in 50 ml of t-butyl alcohol at room temperature, and the mixture was stirred for 15 minutes. The reaction mixture was acidified with ice water and 1N hydrochloric acid, and then extracted with ethyl acetate. The extract was washed with water and brine, dried over anhydrous magnesium sulfate, and concentrated under reduced pressure to obtain 4.00 g crude produce of desired carboxylic acid as an oil, which was used in the next step without purification.

$^1$H-NMR: δ(CDCl$_3$) 1.71–1.90(2H,m) 2.16–2.28(2H,m) 2.33–2.50(2H,m) 3.28(3H,s) 3.58(3H,s) 3.83(3H,s) 3.84 (3H,s) 3.94(3H,s) 4.00(3H,s) 5.41(2H,s) 6.73–6.80(2H,m) 6.86–6.93(1H,m) 6.97(1H,s) 7.44(1H,s) ppm.

ii) Under nitrogen flow, 6.69 g (31.8 mmol) of trifluoroacetic anhydride was added to a solution of 4.00 g of the crude carboxylic acid obtained above in 80 ml of dry benzene, and the mixture was heated under reflux for 2.5 hours. After cooling, saturated aqueous sodium bicarbonate was added, and then the mixture was extracted with ethyl acetate. The extract was washed with water and brine, and dried over anhydrous magnesium sulfate. After concentration under reduced pressure, the residue was purified by medium pressure column chromatography on silica gel (Merck, Lobar column, size C; ethyl acetate:toluene=1:5) and crystallized from methanol to obtain 1.22 g (overall yield: 37%) of desired compound I-80 as crystals.

mp: 164°166° C.

$^1$H-NMR: δ(CDCl$_3$) 1.87–2.03(2H,m) 2.50–2.62(2H,m) 2.65–2.76(2H,m) 3.26(3H,s) 3.86(3H,s) 3.89(3H,s) 3.95 (3H,s) 4.02(3H,s) 6.70–6.78(2H,m) 6.90–6.96(1H,m) 7.86 (1H,s) 14.42(1H,s) ppm.

IR: ν(CHCl$_3$) 3010, 2945, 2840, 1615, 1592, 1516, 1490, 1465, 1413, 1383, 1138, 1130, 1075, 1032 cm$^{-1}$.

Examples of experiments are shown below.

Experiment 1

Inhibitory effect on oxidative modification of LDL (Methods of experiment and evaluation)

According to the method by Kita et al. (Proc. Natl. Acad. Sci., U.S.A., Vol. 84, 5928 (1987)), the experiment was proceeded as follows.

LDL was isolated from the blood of New Zealand albino rabbits fed with a diet containing 0.5% cholesterol for 3 weeks, and dissolved in phosphate-buffered physiological saline (final LDL concentration: 0.2 mg protein/ml). To this solution, each test compound in ethanol was added and then copper sulfate (final $Cu^{2+}$ concentration: 0.5 µM) was added thereto. The mixture was incubated at 37° C. for 24 hours.

After incubation, the content of lipid peroxides in each solution was determined as thiobarbituric acid reactive substances (TBA reactive substances). Concentration for 50% inhibition ($IC_{50}$) was obtained from a linear regression curve of concentration of a compound versus % inhibition of oxidative modification of LDL. To quantify TBA reactive substances, proteins were removed from the solution after incubation, and the supernatant was examined for the content of TBA reactive substances by TBA method.

The results are shown in Tables 29 and 30.

Any of the compounds exhibited an $IC_{50}$ value not higher than 10 µM, demonstrating that the present compounds have potent anti-oxidative effect on LDL.

Experiment 2

Hypocholesterolemic effect
(Methods of experiment and evaluation)

Male ICR mice weighing 30 to 40 g were allowed to access to a diet containing 1% cholesterol and 0.5% sodium cholate supplemented with 0.12% of a test compound (no test compound in control group) ad libitum for 7 days. Then, the blood was taken and total cholesterol in serum was determined by the method of Allain (Clin. Chem., Vol. 20, 470 (1974)).

Total amount of VLDL cholesterol and LDL cholesterol was obtained by subtracting HLD cholesterol from total cholesterol. HLD cholesterol was quantified by the method of Ash and Hentschel et al. (Clin. Chem., Vol. 24, 2180 (1978)).

Hypocholesterolemic effect of a test compound was evaluated based on % reduction in cholesterol calculated using the equation shown below.

% reduction in total cholesterol =   Equation 1

$$\left(1 - \frac{\text{(total cholesterol in treatment group)}}{\text{(total cholesterol in control group)}}\right) \times 100$$

% reduction in (VLDL + LDL) cholesterol =

$$\left(1 - \frac{\text{(VLDL + LDL cholesterol in treatment group)}}{\text{(VLDL + LDL cholesterol in control group)}}\right) \times 100$$

The results are shown in Table 27 and Table 28.

TABLE 27

| Exam. No. | Inhibition of LDL oxidation $IC_{50}$ (µM) | Total Chol. reduction (%) | (VLDL + LDL) Chol. reduction (%) |
|---|---|---|---|
| 1 | 0.40 | 35 | 72 |
| 2 | 1.24 | 22 | 59 |
| 3 | 0.12 | 21 | 57 |
| 4 | 0.65 | 28 | 78 |
| 5 | 0.46 | 22 | 61 |
| 6 | 0.18 | 16 | 55 |
| 7 | 2.58 | 23 | 59 |
| 8 | 4.67 | 17 | 50 |
| 15 | 7.90 | 23 | 43 |
| 16 | 1.85 | 26 | 56 |
| 18 | 1.00 | 13 | 66 |
| 19 | 1.05 | 11 | 58 |
| 20 | 2.50 | 14 | 63 |
| 22 | 0.82 | 12 | 60 |

TABLE 27-continued

| Exam. No. | Inhibition of LDL oxidation $IC_{50}$ (µM) | Total Chol. reduction (%) | (VLDL + LDL) Chol. reduction (%) |
|---|---|---|---|
| 23 | 1.42 | 28 | 74 |
| 24 | 0.98 | 11 | 54 |
| 25 | 2.07 | 16 | 59 |
| 26 | 0.79 | 10 | 54 |
| 28 | 1.52 | 22 | 61 |
| 29 | 1.38 | 20 | 42 |
| 30 | 2.00 | 7 | 44 |
| 31 | 0.85 | 15 | 41 |
| 33 | 3.39 | 19 | 50 |
| 34 | 1.75 | 23 | 53 |
| 36 | 2.21 | 21 | 49 |
| 38 | 2.10 | 26 | 61 |
| 40 | 4.29 | 23 | 56 |
| 41 | 17 | 11 | 41 |
| 42 | 1.68 | 5 | 26 |
| 43 | 2.12 | 15 | 59 |
| 46 | 6.20 | 5 | 47 |

TABLE 28

| Exam. No. | Inhibition of LDL oxidation $IC_{50}$ (µM) | Total Chol. reduction (%) | (VLDL + LDL) Chol. reduction (%) |
|---|---|---|---|
| 56 | 1.28 | 20 | 58 |
| 60 | 2.03 | 6 | 33 |
| 61 | 4.95 | 11 | 43 |
| 62 | 8.98 | 27 | 59 |
| 63 | 2.32 | 20 | 53 |
| 64 | 7.10 | 2 | 39 |
| 66 | 1.47 | 9 | 36 |
| 69 | 2.79 | 10 | 16 |
| 71 | 5.96 | 16 | 44 |
| 72 | 0.59 | 20 | 64 |
| 73 | 2.92 | 13 | 60 |
| 74 | 6.56 | 6 | 41 |
| 76 | 0.54 | 15 | 43 |
| 77 | 2.55 | 18 | 53 |
| 78 | 0.62 | 14 | 42 |

Any of the compounds exhibited excellent ability of reducing VLDL+LDL cholesterol without reducing HDL cholesterol, demonstrating that the present compounds have potent selective cholesterol-reducing effect.

Effects of invention

Since the present compounds have selective cholesterol-reducing effect for VLDL cholesterol and LDL cholesterol which promote arteriosclerosis while inhibiting the oxidative modification of LDL, they are very useful anti-hyperlipemic agents.

We claim:

1. A compound of the formula (VII'):

(VII')

in which $R^1$ is 2-ethylbutyl; and $R^{17}$ is methyl.

* * * * *